United States Patent
Morvan et al.

(10) Patent No.: US 10,105,380 B2
(45) Date of Patent: Oct. 23, 2018

(54) GLYCOCLUSTERS AND THEIR PHARMACEUTICAL USE AS ANTIBACTERIALS

(71) Applicants: CENTRE NATIONAL DE LA RECHERCHE SCIENTIFIQUE (CNRS), Paris (FR); UNIVERSITE MONTPELLIER, Montpellier (FR)

(72) Inventors: Francois Morvan, Castelnau le Lez (FR); Jean-Jacques Vasseur, Combaillaux (FR); Caroline Ligeour, Paris (FR); Yann Chevolot, Fleurieux sur l'Arbresle (FR); Eliane Souteyrand, Chambon sur Cisse (FR); Olivier Vidal, Perenchies (FR); Alice Goudot, Fontaine-les-Dijon (FR); Sebastien Vidal, Saint Maurice de Gourdans (FR)

(73) Assignees: CENTRE NATIONAL DE LA RECHERCHE SCIENTIFIQUE, Paris (FR); UNIVERSITE DE MONTPELLIER 1, Montpellier (FR)

( * ) Notice: Subject to any disclaimer, the term of this patent is extended or adjusted under 35 U.S.C. 154(b) by 251 days.

(21) Appl. No.: 15/023,470

(22) PCT Filed: Sep. 22, 2014

(86) PCT No.: PCT/EP2014/070110
§ 371 (c)(1),
(2) Date: Mar. 21, 2016

(87) PCT Pub. No.: WO2015/040209
PCT Pub. Date: Mar. 26, 2015

(65) Prior Publication Data
US 2016/0287620 A1 Oct. 6, 2016

(30) Foreign Application Priority Data

Sep. 23, 2013 (EP) .................................... 13306296
Mar. 21, 2014 (FR) .................................... 14 52355

(51) Int. Cl.
A61K 9/00 (2006.01)
A61K 31/7056 (2006.01)
A61K 45/06 (2006.01)
C07H 15/26 (2006.01)
A61K 31/70 (2006.01)
A61K 31/7052 (2006.01)

(52) U.S. Cl.
CPC ........ *A61K 31/7056* (2013.01); *A61K 9/0073* (2013.01); *A61K 31/70* (2013.01); *A61K 31/7052* (2013.01); *A61K 45/06* (2013.01); *C07H 15/26* (2013.01)

(58) Field of Classification Search
CPC ................ A61K 31/70; A61K 31/7052; A61K 31/7056; A61K 9/0073; A61K 45/06; A61K 2300/00; C07H 15/26

USPC ........................................................... 514/32
See application file for complete search history.

(56) References Cited

PUBLICATIONS

The Merck Manual, 1992, 16th Ed., pp. 100, 110 and 225.*
Philip S. Stewart et al., "Antibiotic resistance of bacteria in biofilms", Lancet 2001; vol. 358: 135-138, Jul. 14, 2001.
Joseph J. Lundquist et al., "The Cluster Glycoside Effect", Chem. Rev. 2002, 102, 555-578.
Jeffrey B. Lyczak et al., "Lung Infections Associated with Cystic Fibrosis", Clinical Microbiology Reviews, Apr. 2002, vol. 15, No. 2, p. 194-222.
Gianluca Cioci et al., "Structural basis of calcium and galactose recognition by the lectin PA-IL of Pseudomonas aeruginosa", FEBS Letters 555 (2003) 297-301.
Anne Imberty et al., "Structures of the lectins from Pseudomonas aeruginosa: insights into the molecular basis for host glycan recognition", Microbes and Infection 6 (2004) 221-228.
Rebecca M. Landry et al., "Mucin—Pseudomonas aeruginosa interactions promote biofilm formation and antibotic resistance", Molecular Microbiology (2006) 59 (1), 142-151.
Isabelle Deguise et al., "Synthesis of glycodendrimers containing both fucoside and galactoside residues and their binding properties to Pa-IL and PA-IIL lectins from Pseudomonas aeruginosa", New Journal of Chemistry, 2007, 31, 1321-1331.
Anne Imberty et al., "Glycomimetics and Glycodendrimers as High Affinity Microbial Anti-adhesins", Chem. Eur. J. 2008, 14, 7490-7499.
Samy Cecioni et al., "Achieving High Affinity towards a Bacterial Lectin through Multivalent Topological Isomers of Calix[4]arene Glycoconjugates", Chem. Eur. J. 2009, 15, 13232-13240.

(Continued)

Primary Examiner — Ganapathy Krishnan
(74) Attorney, Agent, or Firm — Young & Thompson

(57) ABSTRACT

A molecule responding to formula (I) of the glycocluster type with galactose residues at their extremities. Simple and efficient methods for the preparation of these compounds. Medical use of compounds (I) as inhibitors of infections by *Pseudomonas aeruginosa*, more specifically as inhibitors of *Pseudomonas aeruginosa*'s virulence.

(I)

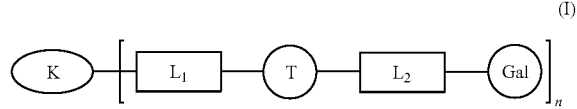

19 Claims, 22 Drawing Sheets

Specification includes a Sequence Listing.

(56) References Cited

PUBLICATIONS

N. Floret et al., "Nosocomial infections caused by Pseudomonas aeruginosa: Exogenous or endogenous origin of this bacterium?", Pathologie Biologie 57 (2009) 9-12.

Rameshwar U. Kadam et al., "A Glycopeptide Dendrimer Inhibitor of the Galactose-Specific Lectin LecA and of Pseudomonas aeruginosa Biofilms", Angew. Chem. Int. Ed. 2011, 50, 10631-10635.

Francesca Pertici et al., Potent divalent inhibitors with rigid glucose click spacers for Pseudomonas aeruginosa lectin LecA, Chem. Commun., 2012, 48, 4008-4010.

Beatrice Gerland et al., "Structure Binding Relationship of Galactosylated Glycoclusters toward Pseudomonas aeruginosa Lectin LecA Using a DNA-Based Carbohydrate Microarray", Bioconjugate Chem. 2014, 25, 379-392.

Jing Zhang et al., "DNA-directed immobilisation of glycomimetics for glycoarrays application: Comparison with covalent immobilisation, and development of an on-chip IC50 measurement assay", Biosensors and Bioelectronics, vol. 24, No. 8, Apr. 15, 2009, pp. 2515-2521, XP026031396.

Gwladys Pourceau et al., "Combinatorial and Automated Synthesis of Phosphodiester Galactosyl Cluster on Solid Support by Click Chemistry Assisted by Microwaves", The Journal of Organic Chemistry, vol. 73, No. 15, Aug. 1, 2008, pp. 6014-6017, XP055107803.

Michael Dubber et al., "Solid-phase synthesis of multivalent glycoconjugates on a DNA synthesizer", Bioconjugate Chemistry, ACS, Washington, DC, US, vol. 14, No. 1, Jan. 1, 2003, pp. 239-246, XP002519660.

Francois Morvan et al., "Oligonucleotide glyco-centered galactosyl cluster conjugates synthesized by multi-click and phosphoramidite chemistries and their affinity for pseudomonas aeruginosa lectin 1" Collection Symposium Series, 12 (Chemistry of Nucleic Acid Components), pp. 148-151, 2011, XP002722124.

Nachman Garber et al., "On the specificity of the D-galactose-binding lectin (PA-I) of Pseudomonas aeruginosa and its strong binding to hydrophobic derivatives of D-galactose and thiogalactose", Biochimica et Biophysica, 1116 (1992) 331-333.

Yuan C. Lee et al., "Carbohydrate-Protein Interactions: Basis of Glycobiology", Accounts of Chemical Research, vol. 28, No. 8, Aug. 1995, pp. 321-327.

Halina Lis et al., "Lectins: Carbohydrate-Specific Proteins That Mediate Cellular Recognition", Chem. Rev. 1998, 98, 637-674.

Chie-Pein Chen et al., "Studies on the binding site of the galactose-specific agglutinin PA-IL from Pseudomonas aeruginosa", Glycobiology, vol. 8, No. 1, pp. 7-16, 1998.

\* cited by examiner

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
     /note="DNA sequence 5'->3' used for DNA anchoring platform"
     /organism="Artificial Sequence"

<400> SEQUENCE: 1
gtgagcccag aggcaggg                                                  18

```
<210> SEQ ID NO 2
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="DNA sequence 5'->3' used for DNA anchoring platform"
      /organism="Artificial Sequence"

<400> SEQUENCE: 2
gtggaggcac caagcttt                                                 18

<210> SEQ ID NO 3
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="DNA sequence used for DNA anchoring platform"
      /organism="Artificial Sequence"

<400> SEQUENCE: 3
ccaagcgagg tggcattt                                                 18

<210> SEQ ID NO 4
<211> LENGTH: 18
<212> TYPE: DNA
<213> ORGANISM: Artificial Sequence
<220> FEATURE:
<221> NAME/KEY: source
<222> LOCATION: 1..18
<223> OTHER INFORMATION: /mol_type="unassigned DNA"
      /note="DNA sequence used for DNA anchoring platform"
      /organism="Artificial Sequence"

<400> SEQUENCE: 4
gcagagagcg tgccattt                                                 18
```

US 10,105,380 B2

GLYCOCLUSTERS AND THEIR PHARMACEUTICAL USE AS ANTIBACTERIALS

FIELD OF THE INVENTION

The invention relates to novel compounds (I) or (II) of the glycocluster type with galactose residues at their extremities. Such compounds have demonstrated good affinity with *Pseudomonas aeruginosa*'s lectin 1, which is a virulence factor of this bacterium. The invention provides simple and efficient methods for the preparation of these compounds. It is also directed to the medical use of compounds (I) or (II) as inhibitors of infections by *Pseudomonas aeruginosa*, more specifically as inhibitors of *Pseudomonas aeruginosa*'s virulence.

BACKGROUND OF THE INVENTION

*Pseudomonas aeruginosa* (PA) is a major public health issue due to its impact on nosocomial infections as well as its impact on cystic fibrosis patient mortality. *Pseudomonas aeruginosa* (PA) is a Gram-negative, aerobic, glucose non-fermenting bacterium and mobile through polar monotrichous flagellum. It is a clinically important opportunistic pathogen often related to hospital infections, because of its ability to survive for long periods, with minimum nutritional requirements and with high tolerance to environmental variations. PA is responsible for 10-30% of hospital-acquired infections (Floret, N. et al., (2009), *Pathol. Biol.* 57, 9-12). It is also the most frequent pathogen, progressively leading to chronic inflammation and to the degradation of the respiratory tract of Cystic Fibrosis patients (Lyczak, J. B. et al., (2002) *Clinical Microbiology Reviews* 15, 194-222). Currently, the use of antibiotics is the only way that can be effective against PA infection. However, in this regard, bacterial multiplication in a biofilm structure seems to give a selective advantage to the pathogen (Stewart, P. S., and Costerton, J. W. (2001) Lancet 358, 135-138. Landry, R. M. et al., (2006) *Mol. Microbiol.* 59, 142-151).

Consequently, regarding the emergence of resistance of most pathogenic bacteria, especially PA, to antibiotics, the development of new antibacterial agents able to escape the mechanisms of resistance or of new modes of action had become imperative and is a major research challenge to treat or prevent infectious diseases. Therefore, inhibition of PA virulence has been proposed as an alternative strategy to tackle PA based infections.

PA-IL, a galactose binding lectin from PA, is involved in its virulence. *Pseudomonas aeruginosa* lectin 1 (PA-IL, Lec A) is a tetravalent lectin with nearly a rectangular shape with binding sites distant of 71 Å on the long side, and 32 Å on the short side (Cioci, G. et al., (2003) *FEBS Lett.* 555, 297-301; Imberty, A., et al., (2004) *Microb. Infect.* 6, 221-228). The binding of PA-IL for monovalent galactosides span in the micromolar range (with the highest affinity for Phenyl-β-Gal) and is influenced by the structure of the aglycon (Garber, N. et al., (1992) *Biochim. Biophys. Acta* 1116, 331-333; Chen, C. P. et al., (1998) *Glycobiology* 8, 7-16).

The binding of PA-IL can reach the nanomolar range when taking advantage of the so-called cluster effect (Lis, H., and Sharon, N. (1998) *Chem. Rev.* 98, 637-674; Lundquist, J. J., and Toone, E. J. (2002) *Chem. Rev.* 102, 555-578; Lee, Y. C., and Lee, R. T. (1995) *Acc. Chem. Res.* 28, 321-327). Multivalent carbohydrate ligands can present enhanced binding to the target lectin per carbohydrate residues as compared to the monovalent ligand. The extent of the enhancement is among others a function of the topology as the residues should fit in the multiple sites of the lectins.

S. Cecioni et al., *Chem. Eur. J.* 2009, 15, 13232-13240 discloses Calix[4]arene Glycoconjugates targeting PA-IL. However, calixarene conjugates are difficult to prepare, with potential formation of diastereoisomers and potential toxicity of calixarene. F. Pertici et al., *Chem. Commun.*, 2012, 48, 4008-4010 discloses di-galactose derivatives as potent divalent inhibitors of *Pseudomonas aeruginosa* lectin LecA. The preparation method of these compounds is long and complicated. A. Imberti et al., *Chem. Eur. J.* 2008, 14, 7490-7499 discloses glycoclusters and their affinity for *E. Coli*'s FimH or *Pseudomonas aeruginosea*'s PA-IIL. I. Deguise et al., *New J. Chem.*, 2007, 31, 1321-1331 discloses the synthesis of glycodendrimers containing both fucoside and galactoside residues and their binding properties to PA-IL and PA-IIL lectins from *Pseudomonas aeruginosa*. Angew. Chem. Int. Ed. 2011, 50, 10631-10635 discloses a glycopeptide dendrimer inhibitor of biofilms of lectin LecA and of *P. aeruginosa*. It does not mention the inhibition of PA-IL adhesion.

To compete efficiently with cell surface glycoconjugates, glycomimetics have to present a strong affinity with their target. Low affinity of lectin-carbohydrate interactions is a barrier in the development of biologically active glycomimetic compounds, and multivalency has permitted to overcome partly this difficulty. However, if prior art results confirm the strong potential of glycomimetics for preventing *Pseudomonas aeruginosa* adhesion, and for use in prevention and treatment of bacterial infection, there remains the need of molecules with a high affinity with PA-IL.

The design and synthesis of such compounds is not easy: the affinity of a glycomimectic for lectin depends not only on the number of carbohydrate groups displayed by the molecule and capable of interacting with lectin PA-IL. It also depends on their arrangement in the molecule: the nature, length and flexibility of linker arms binding the carbohydrate groups to the rest of the molecule. Moreover, on account of complicated synthesis, many prior art glycomimetics are accessible in small quantities only.

There remains the need for molecules presenting a strong affinity for pathogen lectins, notably for PA-IL. Notably, there remains the need for molecules capable of inhibiting the adhesion of *P. aeruginosa*, thereby inhibiting the formation of a biofilm of *P. aeruginosa*. Such molecules should be capable of being produced by simple and efficient methods to give access to a medicament.

SUMMARY OF THE INVENTION

The object of the present invention is to alleviate at least partly the above mentioned drawbacks.

The invention provides molecules presenting a strong affinity for pathogen lectins, notably for PA-IL. More particularly, the invention is directed to synthetic ligands toward PA-IL for its inhibition. More specifically, the invention is directed at compounds targeting the inhibition of PA adhesion. Monosaccharide centered clusters and comb-like clusters were synthesized with different linkers bearing an aryl group separating the core and the galactosyl residues. Simple and efficient methods for the preparation of these compounds are disclosed. Such methods could be easily extrapolated to industrial scale.

This object is achieved with a molecule responding to formula (I):

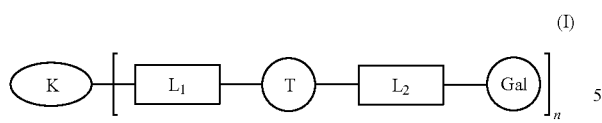
(I)

Wherein n is an integer selected from 3, 4, 5, 6, 7, 8, 9, 10,

Gal represents a radical selected from: galactopyranosyl, 1-thiogalactopyranosyl, 1-methylenegalactopyranosyl, 1-N-acetyl-galactopyranosyl:

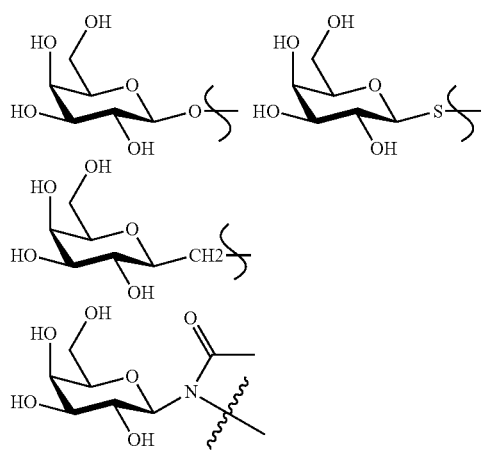

K represents a molecule of formula (KI) or (KII) comprising from 3 to 6 phosphate or thiophosphate or phosphoramidate groups (Pho) selected from:

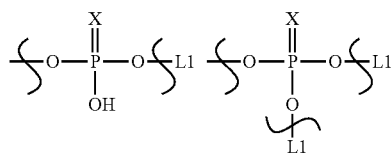

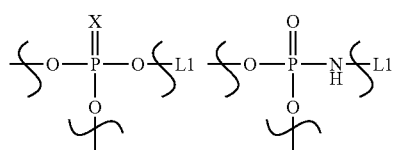

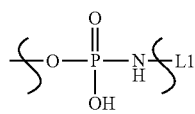

Wherein X represents O or S,

One or two oxygen atoms of the phosphate group being linked by a covalent link to a L1 linker arm, the phosphate or thiophosphate or phosphoramidate groups Pho being either all linked to a same K' center as represented in the formula (KI) here-under:

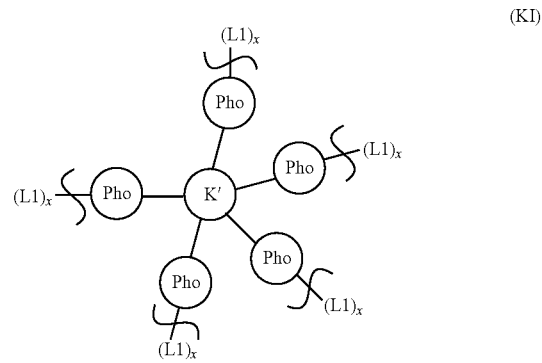
(KI)

with K' representing a molecule comprising from 4 to 24 carbon atoms, from 0 to 12 oxygen atoms, and the corresponding number of hydrogen atoms, one oxygen atom of Pho being linked by a covalent link to K', x=1 or 2 or the phosphate or thiophosphate or phosphoramidate groups form a chain as represented in the formula (KII) here-under:

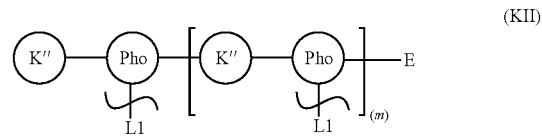
(KII)

wherein K" represents a molecule comprising from 4 to 12 carbon atoms, from 0 to 6 oxygen atoms, from 0 to 6 nitrogen atoms, and the corresponding number of hydrogen atoms, E represents an end group comprising from 0 to 12 carbon atoms, from 0 to 6 oxygen atoms, from 0 to 6 nitrogen atoms, and the corresponding number of hydrogen atoms, m represents an integer selected from 2, 3, 4, 5, two oxygen atoms of Pho being linked by a covalent link to K" groups or to E, L1 represents a linker arm selected from:
a linear, branched or cyclic C1-C18 alkyl di radical, possibly comprising one or several ether bridges —O—,
a poly(ethylene glycol) di radical comprising 2 to 6 ethylene glycol units,
a polypyleneglycol) di radical comprising 2 to 6 propylene glycol units, T represents a connecting group selected from:
a triazole di-radical

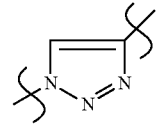

a thio bridge —S—

L2 represents a linker arm responding to the formula $-L_{21}-Ar-L_{22}-$ represented here-under:

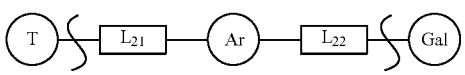

Wherein

L$_{21}$ represents a linear, branched or cyclic C1-C12 alkyl di radical, possibly comprising one or several groups selected from: an amide bridge —CO—NH—, an ether bridge —O—, a thio bridge —S—, an amine bridge —NH—, Ar represents a C6-C18 aromatic di-radical optionally including one to 6 heteroatoms, L$_{22}$ represents a covalent link or when Gal represents a radical selected from: galactopyranosyl, 1-thiogalactopyranosyl, L$_{22}$ can be a —CH2- radical.

Preferred embodiments comprise one or more of the following features:

A molecule responding to formula (I), wherein one or several of the following conditions are verified:
- Gal represents a β-D-galactopyranosyl radical, or a β-D-thio-1-galactopyranosyl radical, preferably a β-D-galactopyranosyl,
- T represents a triazole di radical
- L1 represents a linker arm selected from: a linear C2-C6 alkyl chain, 1,1,1-(trishydroxymethyl)ethane, a poly(ethylene glycol) di radical comprising 2 to 4 ethylene glycol units,
- L$_{21}$ represents a C1-C12 linear alkyl chain comprising one amide function —CO—NH— at its extremity connected to the Ar group,
- Ar represents a C6-C12 aromatic di-radical, preferably Ar represents a group selected from: phenyl, naphtalenyl, 1,4-biphenyl, even more preferably Ar is phenyl,
- L$_{22}$ represents a covalent link.

A molecule responding to formula (I), wherein K is represented by formula (KI), x=1 K comprises from 3 to 5 Pho pending groups:

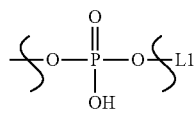

and K' represents a carbohydrate selected from: a pyranose and a furanose.

A molecule responding to formula (I), wherein K' represents a carbohydrate selected from: mannose, galactose, glucose, arabinose, xylose, ribose and lactose.

A molecule responding to formula (I), wherein K is represented by formula (KII), K" represents a linear, branched or cyclic alcane di-yl group comprising from 4 to 10 carbon atoms and Pho is:

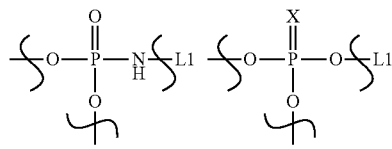

Wherein X=O, S.

A molecule responding to formula (I), wherein K" represents a group selected from 1,4-dimethylcyclohexyl, 1,4-diethylcyclohexyl.

A molecule responding to formula (I), selected from:
(DMCH-PNMTzAcNPhe-O-Gal)$_3$
(DMCH-PNMTzAcNPhe-O-Gal)$_4$
(DMCH-PNMTzAcNPhe-O-Gal)$_5$
Man(POProTzAcNPhe-O-Gal)$_4$
Gal(POProTzAcNPhe-O-Gal)$_4$
Glc(POProTzAcNPhe-O-Gal)$_4$
Man(POEG$_2$MTzAcNPhe-O-Gal)$_4$
Man(POProTzAcNPhe-O-Gal)$_8$
Man[POTHME(MTzAcNPhe-O-Gal)$_2$]$_4$ Wherein DMCH represents dimethylcyclohexane, Man represents mannose, Gal represents galactose, Glc represents glucose;

Pro represents 1,3-n-propyl, Hex represents 1,6-n-hexyl, EG2M represents diethylene glycol methylene, THME represents tris-(hydroxymethyl)ethane;

Tz represents triazole

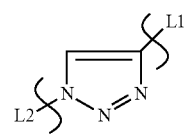

EG2 represents diethylene glycol,
AcNPhe represents acetamidophenyl:

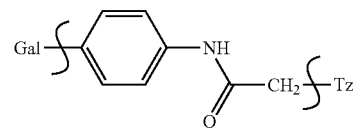

M represents methylene,
Gal represents galactopyranosyl,
PN represents phosphoramidate linkage
PO represents phosphate linkage.

The invention is also directed to a pharmaceutical composition comprising at least one compound of the general formula (I) or (II) or a pharmaceutically acceptable salt thereof, and a pharmaceutically acceptable carrier and/or excipient.

According to a favorite embodiment, the pharmaceutical composition is formulated to be inhaled or instilled in the respiratory tract.

According to a favorite embodiment, the pharmaceutical composition further comprises at least one or more other antibacterial agent(s) or one or more other antivirulence agent(s) or one or more drug(s) reinforcing the host innate immunity The invention is also directed to a compound responding to formula (I) or (II), for use for the prevention, delaying, attenuating and therapeutical treatment of infections due to microbial pathogens, particularly bacterial pathogens.

According to a favorite embodiment, the compound is for treating, delaying, attenuating or preventing infections from *Pseudomonas aeruginosa.*

According to a favorite embodiment, the compound is for administration to patients with cystic fibrosis, or patients under respiratory assistance.

Another object of the invention is a molecule responding to formula (II):

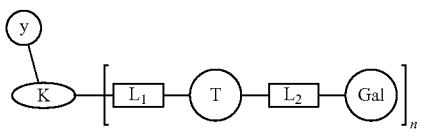

(II)

Wherein
K, n, Gal, T, L1, L2 have the same definition as in claims 1 and wherein y represents a marker, like a DNA sequence or a fluorescent dye.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 7a illustrates the building of phosphoramidate linkages, FIG. 7b illustrates the building of phosphotriester or thionophosphotriester linkages

DETAILED DESCRIPTION OF THE INVENTION

Figure 1:
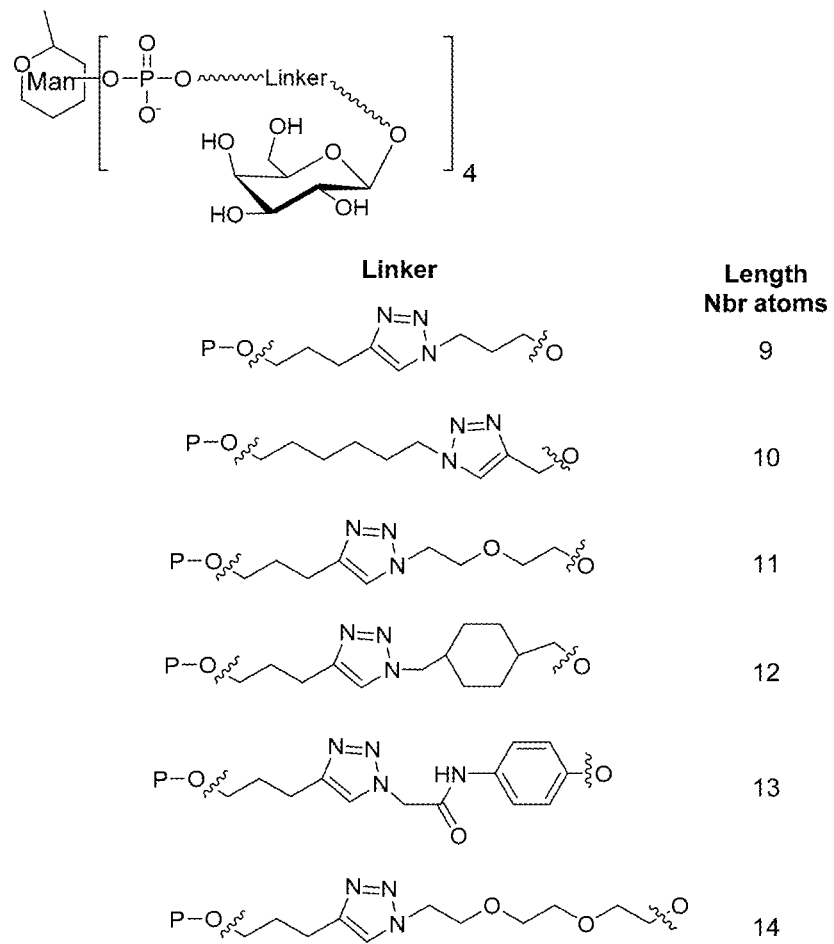
FIG. 1 shows the general structure of some mannose-centered galactoclusters with the nature and length of their linkers. On the left hand side, the linkers are linked to the scaffold. On the right hand side, they are linked to the galactosyl residue

The invention provides molecules responding to formula (I):

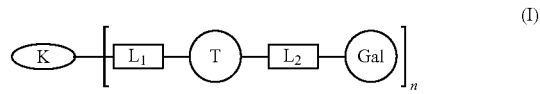

(I)

Wherein n is an integer selected from 3, 4, 5, 6, 7, 8, 9, 10,

Gal represents a radical selected from: galactopyranosyl, 1-thiogalactopyranosyl, 1-methylenegalactopyranosyl, 1-N-acetyl-galactopyranosyl:

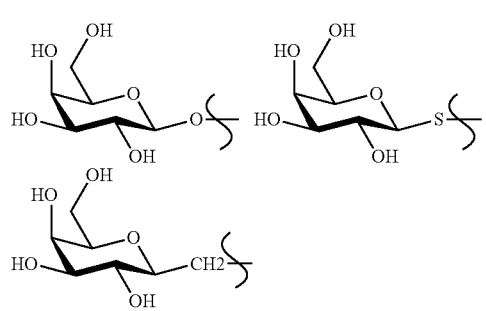

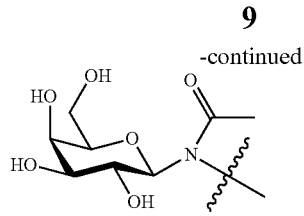

K represents a molecule of formula (KI) or (KII) comprising from 3 to 6 phosphate or thiophosphate or phosphoramidate groups (Pho) selected from:

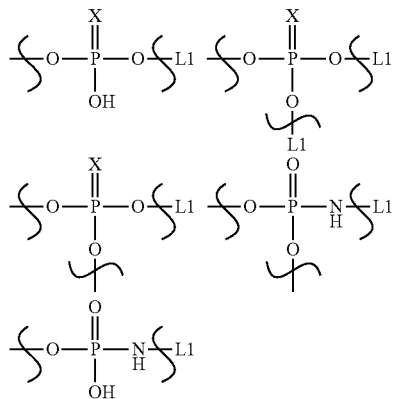

Wherein X represents O or S,

One or two oxygen atoms of the phosphate group being linked by a covalent link to a L1 linker arm, according to a first embodiment, the molecule of formula (I) is a core-centered cluster:

the phosphate or thiophosphate or phosphoramidate groups Pho being either all linked to a same K' center as represented in the formula (KI) here-under:

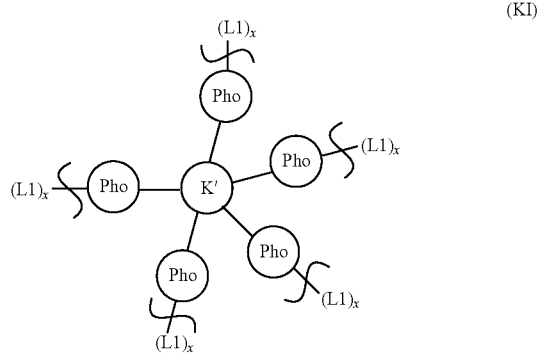

with K' representing a molecule comprising from 4 to 24 carbon atoms, from 0 to 12 oxygen atoms, and the corresponding number of hydrogen atoms, one oxygen atom of Pho being linked by a covalent link to K', The number of Pho groups linked to K' can vary from 1 to 9. For the purpose of illustration only, 5 Pho groups have been represented on figure (KI).

In (KI) Pho groups are connected to the core K' through one phosphate or thio phosphate bond and are selected from:

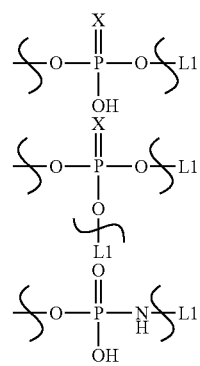

In (KI), x=1 or 2, since phosphate and thiophosphate groups can be linked to one or two Gal groups through linker arms -L1-T-L2-.

according to a second embodiment, the molecule of formula (I) is a comb-like cluster:

the phosphate or thiophosphate or phosphoramidate groups form a chain as represented in the formula (KII) here-under:

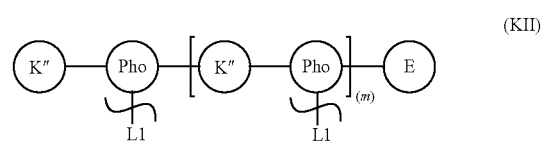

wherein K″ represents a molecule comprising from 4 to 12 carbon atoms, from 0 to 6 oxygen atoms, from 0 to 6 nitrogen atoms, and the corresponding number of hydrogen atoms, E represents an end group comprising from 0 to 12 carbon atoms, from 0 to 6 oxygen atoms, from 0 to 6 nitrogen atoms, and the corresponding number of hydrogen atoms, According to this embodiment, K″ and E can for example be an alcane or cyclo-alcane di-radical, an alkylene glycol di-radical, a carbohydrate di-radical or a nucleotide di-radical, an aralkyl di-radical including at least two —CH2- groups between the aromatic ring and —O— from Pho, E can also be H, m represents an integer selected from 2, 3, 4, 5, 6, 7, 8, 9, two oxygen atoms of Pho are linked by a covalent link to K″ groups or to E, Pho is selected from:

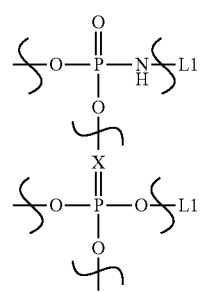

And X is O or S,

L1 represents a linker arm selected from:

a linear, branched or cyclic C1-C18 alkyl di radical, possibly comprising one or several ether bridges —O—, a poly(ethylene glycol) di radical comprising 2 to 6 ethylene glycol units, a poly(propyleneglycol) di radical comprising 2 to 6 propylene glycol units, T represents a connecting group selected from:

a triazole di-radical

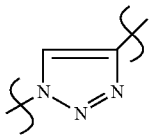

a thio bridge —S—

L2 represents a linker arm responding to the formula -$L_{21}$-Ar-$L_{22}$- represented here-under:

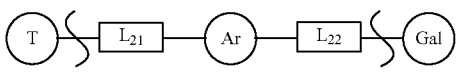

Wherein $L_{21}$ represents a linear, branched or cyclic C1-C12 alkyl di radical, possibly comprising one or several groups selected from: an amide bridge —CO—NH—, an ether bridge —O—, a thio bridge —S—, an amine bridge —NH—, Ar represents a C6-C18 aromatic di-radical optionally including one to 6 heteroatoms, $L_{22}$ represents a covalent link or when Gal represents a radical selected from: galactopyranosyl, 1-thiogalactopyranosyl, $L_{22}$ can be a —CH2- radical.

According to a favorite variant, Gal represents a β-D-galactopyranosyl radical, or a β-D-thio-1-galactopyranosyl radical. Preferably, in formula (I), Gal represents a β-D-galactopyranosyl, According to a favorite variant, T represents a triazole di radical The triazole radical is non symmetric. In formula (I), the nitrogen atom of the triazole ring can be linked to L1 and the carbon atom is linked to L2 or the nitrogen atom can be linked to L2 and the carbon atom is linked to L1.

Preferably, as illustrated in molecules disclosed in the experimental part, the connection is:

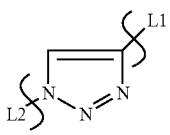

According to a favorite variant, L1 represents a linker arm selected from: a linear C2-C6 alkyl chain, 2,2-bis(methyloxymethyl)ethyl, a poly(ethylene glycol) di radical comprising 2 to 4 ethylene glycol units.

According to a favorite variant, $L_{21}$ represents a C1-C12 linear alkyl chain comprising one amide function —CO—NH— at its extremity connected to the Ar group. The connection through the amide bond can be alkyl-CO—NH—Ar or Ar—CO—NH-alkyl. Preferably, as illustrated in the experimental part, the connection is alkyl-CO—NH—Ar.

According to a favorite variant, Ar represents a C6-C12 aromatic di-radical, preferably Ar represents a group selected from: phenyl, naphtalenyl, 1,4-biphenyl, even more preferably Ar is phenyl and is substituted in positions 1,4.

According to a favorite variant, $L_{22}$ represents a covalent link.

According to a first embodiment K is represented by formula (KI). Preferably, according to this variant, K comprises 3, 4 or 5 Pho pending groups:

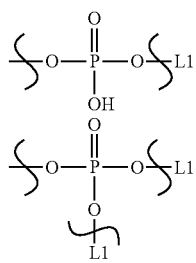

Even more preferably, according to this variant, x=1, K comprises 3, 4 or 5 Pho pending groups:

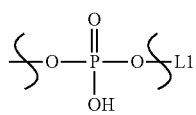

K' can represent a linear, branched or cyclic alcane poly-radical. K' can represent a linear, branched or cyclic alcanol poly-radical. K' can also represent a linear, branched or cyclic carbohydrate poly-radical.

Advantageously, according to this variant, K' represents a carbohydrate selected from: a pyranose and a furanose. Even more preferably, according to this variant, K' represents a carbohydrate selected from: mannose, galactose, glucose, arabinose, xylose, ribose and lactose.

According to another embodiment K is represented by formula (KII). Preferably, according to this variant, K" represents a linear, branched or cyclic alcane di-yl group comprising from 4 to 10 carbon atoms and Pho is:

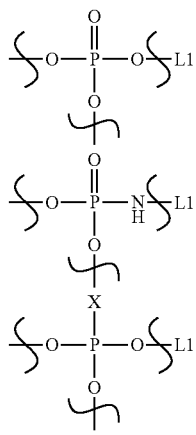

Even more preferably, according to this variant, K" represents a group selected from 1,4-dimethylcyclohexyl, 1,4-diethylcyclohexyl.

The object of the present invention is also achieved with a molecule responding to the formula (II):

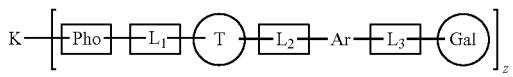

Wherein

K represents a carbohydrate selected from the group consisting of mannose, galactose, glucose, arabinose, xylose, ribose and lactose Pho represents a phosphorous group selected from the group consisting of:

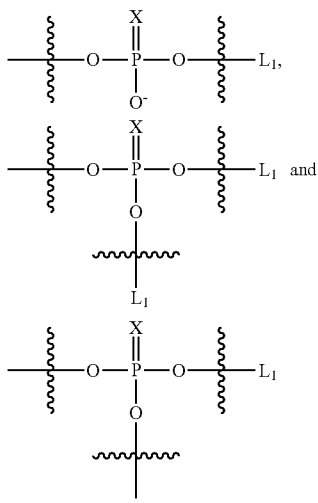

Wherein X represents O or S,

One or two oxygen atoms of the phosphate group being linked by a covalent link to a L1 linker arm, L1 represents a linker arm selected from the group consisting of:

a linear or branched $C_1$-$C_3$ alkyl di radical, a linear, branched or cyclic $C_4$-$C_6$ alkyl di radical, a linear, branched or cyclic $C_7$-$C_{12}$ alkyl di radical possibly comprising one or several ether bridges —O—, a poly(ethylene glycol) di radical comprising 2, 3, 4, 5 or 6 ethylene glycol units, a polypyleneglycol) di radical comprising 2, 3, 4, 5 or 6 propylene glycol units, T represents a connecting group selected from:

a triazole di-radical

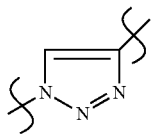

L2 represents a linker arm selected from the group consisting of

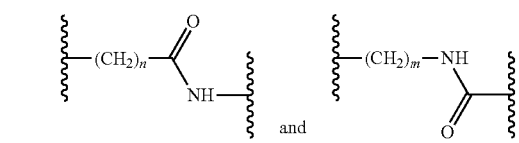

n and m represent an integer selected from 1, 2, 3, 4, or 5

Ar is selected from the group consisting of phenyl, naphtalenyl and 1,4-biphenyl

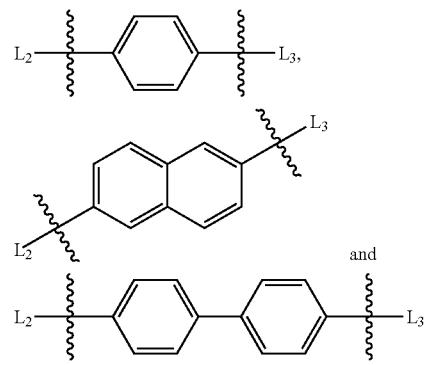

L3 represents O, S or —CH2

Gal represents the radical β-D-galactopyranosyl:

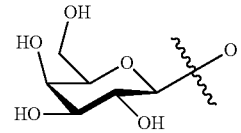

It is noted that the —O— group corresponds to L3.

z is an integer selected from 1, 2 3, 4, 5, 6, 7, 8, 9 or 10

According to a favorite variant, K represents the mannose under the form D-mannopyranosyl.

According to a favorite variant L1 represents a group Pro (1,3-n-propyl), EG2M (diethylene glycol methylene), EG3M (triethylene glycol methylene), EG4M (tetraethylene glycol methylene).

According to a favorite variant Ar is the phenyl group.

According to a favorite variant z is 3 or 4.

Favorite molecules responding to formula (I) or (II) are listed here-under:

(DMCH-PNMTzAcNPhe-O-Gal)$_3$
(DMCH-PNMTzAcNPhe-O-Gal)$_4$
(DMCH-PNMTzAcNPhe-O-Gal)$_5$
Man(POProTzAcNPhe-O-Gal)$_4$
Gal(POProTzAcNPhe-O-Gal)$_4$
Glc(POProTzAcNPhe-O-Gal)$_4$
Man(POEG$_2$MTzAcNPhe-O-Gal)$_4$
Man(POEG$_3$MTzAcNPhe-O-Gal)$_4$
Man(POEG$_4$MTzAcNPhe-O-Gal)$_4$
Man(POProTzAcNPhe-O-Gal)$_8$
Man(POEG$_2$MTzAcNPhe-O-Gal)$_8$
Man(POEG$_3$MTzAcNPhe-O-Gal)$_8$
Man[POTHME(MTzAcNPhe-O-Gal)$_2$]$_4$
Man(POProTzAcNPhe-S-Gal)$_4$
Man(POEG$_2$MTzAcNPhe-S-Gal)$_4$
Man(POEG$_3$MTzAcNPhe-S-Gal)$_4$

Man(POEG₄MTzAcNPhe-S-Gal)₄
Man(POProTzAcNPhe-CH₂—O-Gal)₄
Man(POEG₂MTzAcNPhe-CH₂—O-Gal)₄
Man(POEG₃MTzAcNPhe-CH₂—O-Gal)₄
Man(POEG₄MTzAcNPhe-CH₂—O-Gal)₄
Man(POProTzAcNPhe-CH₂—S-Gal)₄
Man(POEG₂MTzAcNPhe-CH₂—S-Gal)₄
Man(POEG₃MTzAcNPhe-CH₂—S-Gal)₄
Man(POEG₄MTzAcNPhe-CH₂—S-Gal)₄
Man(PSProTzAcNPhe-O-Gal)₄
Man(PSEG₂MTzAcNPhe-O-Gal)₄
Man(PSEG₃MTzAcNPhe-O-Gal)₄
Man(PSEG₄MTzAcNPhe-O-Gal)₄
Man(PSProTzAcNPhe-S-Gal)₄
Man(PSEG₂MTzAcNPhe-S-Gal)₄
Man(PSEG₃MTzAcNPhe-S-Gal)₄
Man(PSEG₄MTzAcNPhe-S-Gal)₄
Man(PSProTzAcNPhe-CH₂—O-Gal)₄
Man(PSEG₂MTzAcNPhe-CH₂—O-Gal)₄
Man(PSEG₃MTzAcNPhe-CH₂—O-Gal)₄
Man(PSEG₄MTzAcNPhe-CH₂—O-Gal)₄
Man(PSProTzAcNPhe-CH₂—S-Gal)₄
Man(PSEG₂MTzAcNPhe-CH₂—S-Gal)₄
Man(PSEG₃MTzAcNPhe-CH₂—S-Gal)₄
Man(PSEG₄MTzAcNPhe-CH₂—S-Gal)₄
(DMCH-POMTzAcNPhe-O-Gal)₃
(DMCH-POMTzAcNPhe-O-Gal)₄
(DMCH-POMTzAcNPhe-O-Gal)₅
(DMCH-POMTzAcNPhe-S-Gal)₃
(DMCH-POMTzAcNPhe-S-Gal)₄
(DMCH-POMTzAcNPhe-S-Gal)₅
(DMCH-POMTzAcNPhe-CH₂—O-Gal)₃
(DMCH-POMTzAcNPhe-CH₂—O-Gal)₄
(DMCH-POMTzAcNPhe-CH₂—O-Gal)₅
(DMCH-POMTzAcNPhe-CH₂—S-Gal)₃
(DMCH-POMTzAcNPhe-CH₂—S-Gal)₄
(DMCH-POMTzAcNPhe-CH₂—S-Gal)₅
(DMCH-PSMTzAcNPhe-O-Gal)₃
(DMCH-PSMTzAcNPhe-O-Gal)₄
(DMCH-PSMTzAcNPhe-O-Gal)₅
(DMCH-PSMTzAcNPhe-S-Gal)₃
(DMCH-PSMTzAcNPhe-S-Gal)₄
(DMCH-PSMTzAcNPhe-S-Gal)₅
(DMCH-PSMTzAcNPhe-CH₂—O-Gal)₃
(DMCH-PSMTzAcNPhe-CH₂—O-Gal)₄
(DMCH-PSMTzAcNPhe-CH₂—O-Gal)₅
(DMCH-PSMTzAcNPhe-CH₂—S-Gal)₃
(DMCH-PSMTzAcNPhe-CH₂—S-Gal)₄
(DMCH-PSMTzAcNPhe-CH₂—S-Gal)₅
Man(PSEG2MTzAcNPhe-CH2-Gal)₄
Man(PSEG3MTzAcNPhe-CH2-Gal)₄
Man(EG2MTzAcNPhe-CH2-Gal)₄
Man(EG3MTzAcNPhe-CH2-Gal)₄
Man(EG2MTzAcNPhe-CH2-SGal)₄
Man(EG3MTzAcNPhe-CH2-SGal)₄
Man(PSEG3MTzAcNPh-Gal)₄
Man(PSEG3MTzAcNPhe-CH2-SGal)₄
Man(PSEG2MTzAcNPhe-CH2-SGal)₄
Man(PSEG3MTzAcNPh-SGal)₄
Man(PSEG2MTzAcNPh-Gal)₄
Man(PSEG2MTzAcNPh-SGal)₄
Man(EG2MTzAcNPh-SGal)₄
Man(EG3MTzAcNPh-SGal)₄
Man(EG3MTzproNCONaphT-OGal)₄
Man(EG3MTzproNCOBisphe-OGal)₄
Man(PSEG3MTzproNCOBisphe-OGal)₄
Man(PSEG2MTzproNCOBisphe-OGal)₄
Man(EG2MTz AcNPh-Gal)₄
Man(PSEG3MTzproNCONapht-OGal)₄
Man(EG3MTzAcNPh-Gal)₄
Man(PSEG2MTzproNCONapht-OGal)₄
Man(EG2MTzproNCOBisphe-OGal)₄
Man(EG2MTzproNCONapht-OGal)₄
(DMCH-POProTzAcNPhe-OGal)₄
(DMCH-PSProTzAcNPhe-OGal)₄
(DMCH-PODMCHMTzAcNPhe-OGal)₄
(DMCH-PSDMCHMTzAcNPhe-OGal)₄
(DMCH-POProTzAcNPhe-SGal)₄
(DMCH-PSProTzAcNPhe-SGal)₄
(DMCH-PODMCHMTzAcNPhe-SGal)₄
(DMCH-PSDMCHMTzAcNPhe-SGal)₄
(DMCH-POProTzProNCOBisphe-OGal)₄
(DMCH-PSProTzProNCOBisphe-OGal)₄
(DMCH-PODMCHMTzProNCOBisphe-OGal)₄
(DMCH-PSDMCHMTzProNCOBisphe-OGal)₄
(DMCH-POProTzProNCOBisphe-SGal)₄
(DMCH-PSProTzProNCOBisphe-SGal)₄
(DMCH-PODMCHMTzProNCOBisphe-SGal)₄
(DMCH-PSDMCHMTzProNCOBisphe-SGal)₄
(DMCH-POProTzProNCONapht-OGal)₄
(DMCH-PSProTzProNCONapht-OGal)₄
(DMCH-PODMCHMTzProNCONapht-OGal)₄
(DMCH-PSDMCHMTzProNCONapht-OGal)₄
(DMCH-POProTzProNCONapht-SGal)₄
(DMCH-PSProTzProNCONapht-SGal)₄
(DMCH-PODMCHMTzProNCONapht-SGal)₄
(DMCH-PSDMCHMTzProNCONapht-SGal)₄

Wherein DMCH represents 1,4-dimethylcyclohexyl, Man represents mannose, Glc represents glucose;

Pro represents 1,3-n-propyl, Hex represents 1,6-n-hexyl, THME represents tris-(hydroxymethyl)ethane;

Tz represents triazole

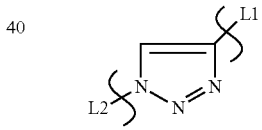

PN represents phosphoramidate linkage
PO represents phosphate linkage
PS represents phosphorothioate linkage
EG2 represents diethylene glycol,
EG3 represents triethylene glycol
EG4 represents tetraethylene glycol
AcNPhe represents acetamidophenyl:

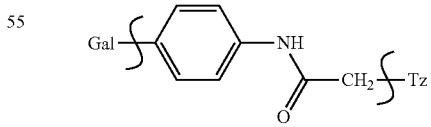

M represents methylene,
—O-Gal represents galactopyranosyl,
S-Gal represents 1-thiogalactopyranosyl
—CH2-O-Gal represents 1-methylenegalactopyranosyl
—CH2-S-Gal represents 1-methylenethiogalactopyranosyl
-NAc-Gal represents 1-N-acetylgalactopyranosyl Linear (DMCH) glycoclusters have phosphoramidate linkages (PN), phosphotriester linkages (PO) or thionophosphotriester linkages (PS) and hexose-centered ones (Man, Gal, Glc) have phosphate linkages (PO) or thionophosphate linkages (PS).

The preparation of these molecules is disclosed in a detailed manner in the experimental part here-under.

Figure 6:
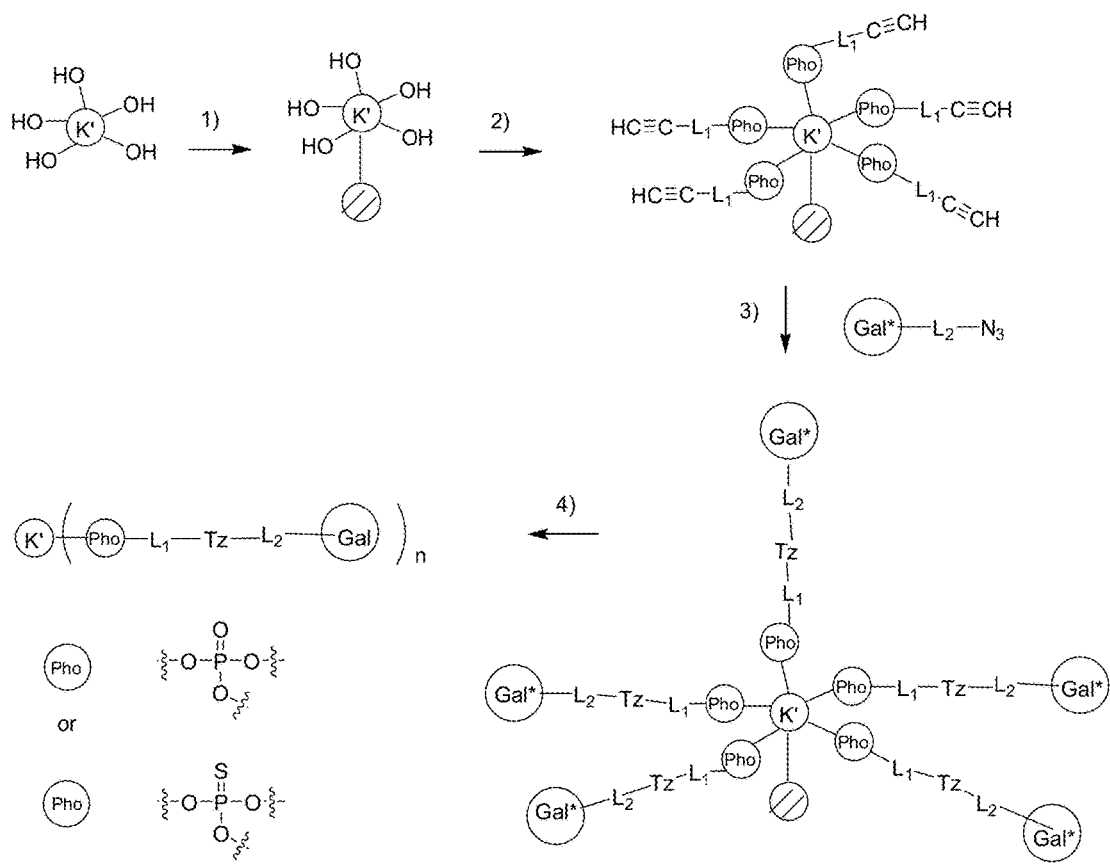
FIG. 6 is a scheme illustrating a synthetic path to structure (I) with K responding to formula (KI)

FIG. 6 illustrates a scheme of preparation of molecules responding to formula (I) wherein K is a core structure represented by formula (KI). Schematically, the OH-functionalized core K' is grafted onto a solid support ⌀ in step 1). However, this step is not compulsory and the synthesis can be achieved in solution. Then in step 2) HC≡C-functionalized linker L1 Pho groups are grafted to hydroxyl functions born by K'. Only one graft per Pho group is illustrated in FIG. 6, but one or two grafts can be operated on Pho. In step 3) a click chemistry reaction is achieved with

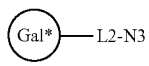

Wherein Gal* represents a Gal residue with protective groups on OH functionalities. Detailed operating modes are illustrated in FIG. 1 and in the experimental part. Alternatively a Gal residue without protective group could be used. The triazole Tz is formed through this reaction with the following substitution:

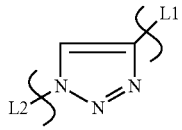

The opposite substitution can be obtained by inversion of N3 and alcyne residues.

A thio ether bond can be obtained in replacement of Tz in a known manner by reacting a thiol with a halogen, notably with a bromine.

In step 5), protective groups are removed from Gal if present and where necessary the bond with the solid support is cleaved.

Figure 7A:
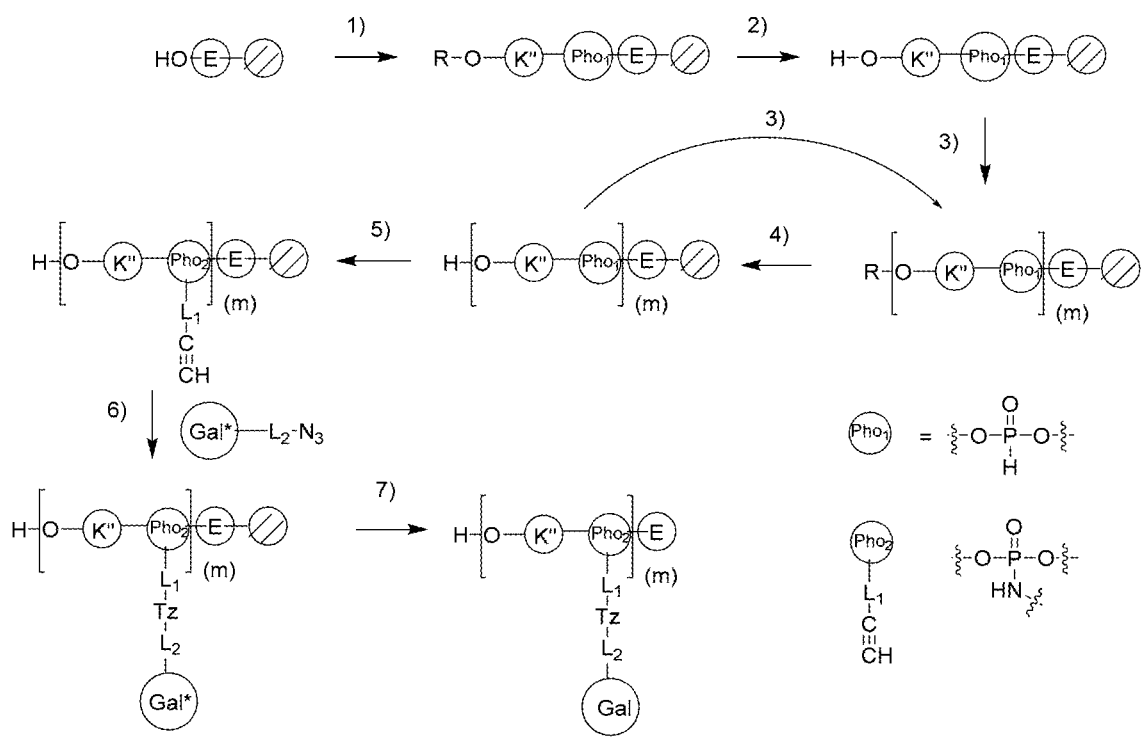
FIGS. 7a and 7b are schemes illustrating a synthetic path to structure (I) with K responding to formula (KII).
Figure 7B:
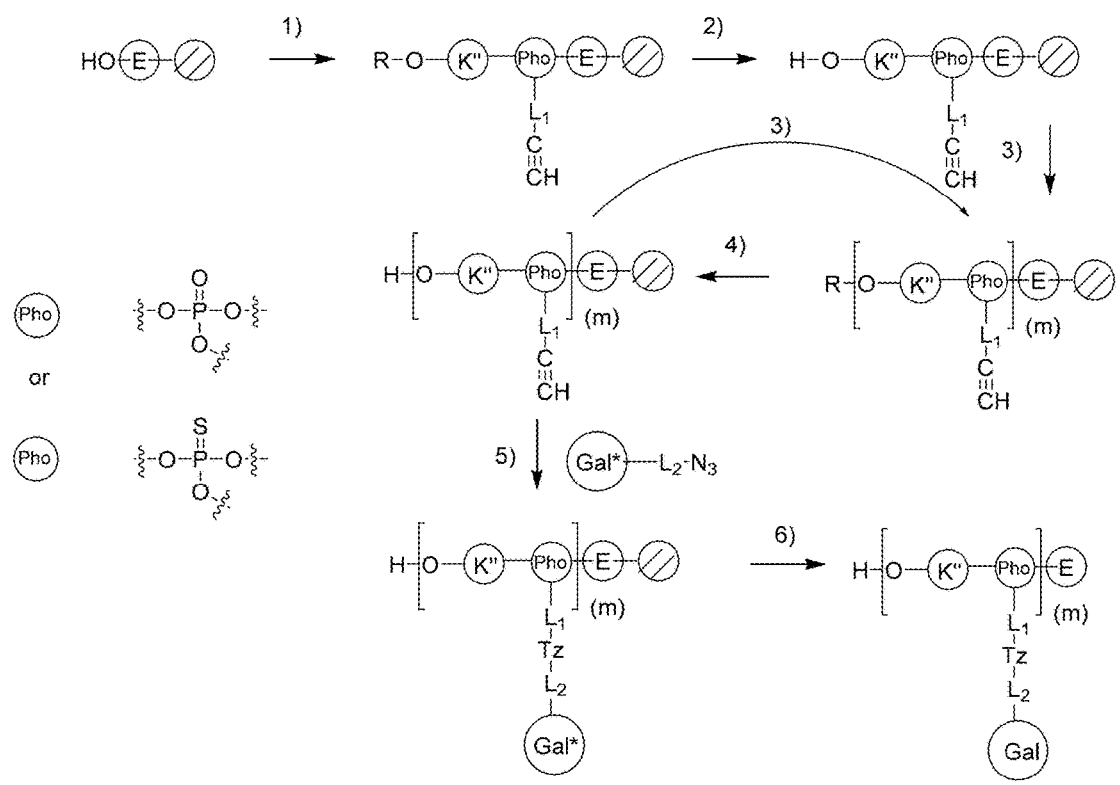

FIGS. 7a and 7b illustrate a scheme of preparation of molecules responding to formula (I) wherein K is a comb structure represented by formula (KII).

On FIG. 7a, schematically, the H-phosphonate fragment K" is reacted with solid-supported ⌀ end group E in step 1). Then in step 2) protection group R (dimethoxytrityl) of K" is removed. In step 3) a second H-phosphonate fragment K" is reacted and in step 4) R group is removed. Steps 3) an 4) are repeated to obtain the desired (m) value. In step 5) the HC≡C-functionalized linker L1 is grafted onto the Pho groups, and the phosphate is transformed into a phosphoramidate. In step 6) a click chemistry reaction is achieved with

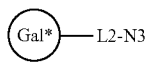

Wherein Gal* represents a Gal residue with protective groups on OH functionalities. Alternatively a Gal residue without protective group could be used. The triazole Tz is formed through this reaction with the following substitution:

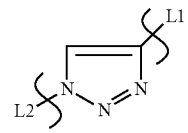

The opposite substitution can be obtained by inversion of N3 and alcyne residues.

Alternately, a thio ether bond can be obtained in replacement of Tz in a known manner by reacting a thiol with a halogen, notably with a bromine.

In step 7), protective groups are removed from Gal if present and the linkage to the solid support is hydrolyzed.

According to a variant, the synthesis can be achieved on a solid support using K" alkyne-L1 functionalized phosphoramidite as described in FIG. 7b. In step 1) a K" alkyne derivative is reacted with end group solid support and oxidized to a phosphatetriester or a thionophosphatetriester. In step 2) R protective group is removed and in step 3) a second K" alkyne derivative is added and oxidized, after R removing in step 4), steps 3) and 4) are repeated to obtain the desired (m) value. In step 5) a click chemistry reaction is achieved with

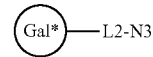

Wherein Gal* represents a Gal residue with protective groups on OH functionalities. Alternatively a Gal residue without protective group could be used. The triazole Tz is formed through this reaction with the following substitution:

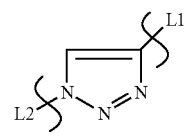

The opposite substitution can be obtained by inversion of N3 and alcyne residues. In this case a bromo phosphoramidite or a tosyl phosphoramidite is first prepared and then converted to an azido phosphoramidite by substitution by an azide reactant.

Alternately, a thio ether bond can be obtained in replacement of Tz in a known manner by reacting a thiol with a halogen, notably with a bromine.

In step 6), protective groups are removed from Gal (if any) and the linkage to the solid support is hydrolyzed.

According to a favorite variant, the synthesis is achieved on a solid support by prior grafting of the first K" group of the chain on a solid support.

The invention also provides molecules responding to formula (II):

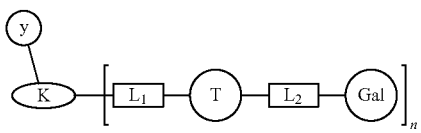

(III)

Wherein

K, n, Gal, T, L1, L2 have the same meaning as above and wherein y represents a marker. A marker can be for example a DNA sequence or a fluorescent dye.

Such a molecule can be used for testing purposes, notably for diagnostic purposes.

Another object of the invention is a pharmaceutical composition comprising at least one compound of the general formula (I) or (II) or a pharmaceutically acceptable salt thereof, and a pharmaceutically acceptable carrier and/or excipient.

Such an excipient is well known to the skilled professional and is adapted, among other parameters, according to the mode of administration.

Said pharmaceutical compositions are advantageously formulated to be administered under oral, topical, transdermal, sublingual, rectal, parenteral routes including intravenous, intramuscular, intraperitoneal and subcutaneous routes, with individual doses appropriate for the patient to be treated. Preferably, the drug is administered by the respiratory or pulmonary way.

These compounds (I) or (II), and pharmaceutical compositions comprising them, are formulated to be inhaled or instilled in the respiratory tract for treating or preventing infections from Pseudomonas aeruginosa, in particular in patients with cystic fibrosis, or patients under respiratory assistance who are often victims of nosocomial infections.

Alternately, compounds (I) or (II) and pharmaceutical compositions comprising them can be used topically, in or under a dressing or a bandage for preventing or treating infections from Pseudomonas aeruginosa, in particular for burns or bedsores.

The compositions according to the invention can be solid, liquid including solutions, emulsions or suspensions, or in the form of a gel/cream and be presented in the pharmaceutical forms commonly used in human medicine, such as for example, solutions, emulsions, plain or sugar-coated tablets, gelatin capsules, granules, suppositories, injectable preparations, ointments, creams, gels; they are prepared according to the customary methods. The active ingredients can be incorporated using excipients which are customarily used in these pharmaceutical compositions, such as talc, gum arabic, lactose, starch, magnesium stearate, aqueous or non-aqueous vehicles, fatty substances of animal or vegetable origin, paraffin derivatives, glycols, various wetting agents, dispersants or emulsifiers, preservatives.

The total daily dose of the compounds for use in accordance with this invention, administered in single or divided doses, may be in amounts of, for example, from 0.001 to approximately 100 mg/kg body weight daily.

The specific dose level for any particular patient will depend on a variety of factors, including body weight, general health, sex, diet, duration and route of administration, levels of intestinal absorption and resorption and of excretion, combination with other medicaments and the severity of the particular condition being treated.

The compounds (I) or (II), and pharmaceutical compositions comprising them, are useful as antibacterial agents for the prevention, delaying, attenuating and therapeutical treatment of infections due to microbial pathogens, in particular infections by pathogens which use lectins in the first steps of the infection, and more particularly infections by a bacterium Pseudomonas aeruginosa.

The invention is directed to a compound of formula (I) or (II) or a pharmaceutical composition comprising it, for its use for the prevention, delaying, attenuating and/or inhibition of the virulence of Pseudomonas aeruginosa.

More specifically, the invention is directed to a compound of formula (I) or (II) or a pharmaceutical composition comprising it, for its use for the prevention, delaying, attenuating and/or inhibition of the formation of a biofilm produced by a bacterium Pseudomonas aeruginosa.

The invention is further directed to a pharmaceutical composition comprising at least one compound of the general formula (I) or (II) or a pharmaceutically acceptable salt thereof, and a pharmaceutically acceptable carrier and/or excipient and at least one or more other antibacterial agent(s) or with one or more other antivirulence agent(s) or with one or more drug(s) reinforcing the host innate immunity.

More specifically, the invention is further directed to a pharmaceutical composition comprising at least one compound of the general formula (I) or (II) or a pharmaceutically acceptable salt thereof, and a pharmaceutically acceptable carrier and/or excipient and at least one antibiotic.

Another object of the invention is the use of the compounds (I) in preventing delaying, attenuating and treating human or animal bacterial infections, in association with one or more drug(s) and more specifically with one or more antibacterial agent(s) or with one or more antivirulence agent(s) or with one or more drug(s) reinforcing the host innate immunity.

A composition comprising at least one compound of the general formula (I) or (II) can be used for material able to capture Pseudomonas aeruginosa.

EXPERIMENTAL

Nomenclature:

Nomenclature used for the glycoclusters illustrated in the experimental part: Each glycocluster is constituted of a scaffold (K), a first linker (L1) a connecting group (T), a second linker (L2) and a galactose derivative (Gal): K-(-L1-T-L2-Gal)n.

Scaffolds used are DMCH (dimethylcyclohexane), Man (mannose), Gal (galactose), Glc (glucose) or dT (thymidine);

PN represents phosphoramidate linkage

PO represents phosphate linkage

PS represents phosphorothioate linkage

L1: Pro (1,3-n-propyl), Hex (1,6-hexyl), EG2M (diethylene glycol methylene), EG3M (triethylene glycol methylene), EG4M (tetraethylene glycol methylene), THME tris-(hydroxymethyl)ethane;

T: triazole Tz;

L2: Pro (1,3-n-propyl), EG2 (diethylene glycol), EG3 (triethylene glycol), DMCH (1,4-Dimethylcyclohexan), AcNPhe (acetamidephenyl), M (methylene), BuT (N3-butyl-thymine).

—O-Gal represents galactopyranosyl

—S-Gal represents 1-thiogalactopyranosyl

—CH2-O-Gal represents 1-methylenegalactopyranosyl

—CH2-S-Gal represents 1-methylenethiogalactopyranosyl

-NAc-Gal represents 1-N-acetylgalactopyranosyl

Linear (DMCH) glycoclusters have phosphoramidate linkages (PN), phosphotriester linkages (PO) or thionophosphotriester linkages (PS) and hexose-centered ones (Man, Gal, Glc) have phosphate linkages (PO) or thionophosphate linkages (PS).

I—Experimental—General Proceeding

The syntheses of phosphoramidites 1 (Meyer, A. et al., (2010) *J. Org. Chem.* 75, 6689-6692), 2 (Lietard, J. et al., (2008) *J. Org. Chem.* 73, 191-200; Lietard, J. et al., Meyer, A., Vasseur, J. J., and Morvan, F. (2007) *Tetrahedron Lett.* 48, 8795-8798), 1a and 1d (Gerland, B. et al., (2012) *Bioconjugate Chem.* 23, 1534-1547) and 1e (Ligeour, C. et al., (2012) *Eur. J. Org. Chem.*, 1851-1856) and azide solid support 5 (Pourceau, G. et al., (2009) *J. Org. Chem.* 74, 6837-6842) were previously reported. Carbohydrate derivatives 3 (Hasegawa, T. et al., (2007) *Org. Biomol. Chem.* 5 (15), 2404-2412), 4a (Joosten, J. A. F. et al., (2004) *J. Med. Chem.* 47, 6499-6508), 4b (Szurmai, Z. et al., (1989) *Acta Chimica Hungarica-Models in Chemistry* 126, 259-269), 4c, (Pourceau, G. et al., (2009) *J. Org. Chem.* 74, 1218-1222), 4d (Cecioni, S. et al., (2012) *Chem. Eur. J.* 18, 6250-6263), 4e (Szurmai, Z. et al., (1989)), 6 (Hasegawa, T., et al. (2007)), 1-propagyl-O-galactopyranose and -glucopyranose (Mereyala, H. B., and Gurrala, S. R. (1998) *Carbohydr. Res.* 307, 351-354) were prepared according literature.

3,6,9,12-Tetraoxa-pentadecan-14-yn-1-yl 2-cyanoethyl N,N-diisopropyl phosphoramidite 1c: 2-Cyanoethyl-N,N-diisopropylchlorophosphoramidite (720 mg, 3.0 mmol) was added to a solution of 3,6,9,12-tetraoxa-pentadecan-14-yn-1-ol (600 mg, 2.6 mmol), 3 Å molecular sieves and N,N'-diisopropylethylamine (DIEA) (1.3 mL, 7.4 mmol) in anhydrous dichloromethane (40 mL). The resulting mixture was stirred at room temperature for 2 h, 2 mL of $H_2O$ was added then the solution was evaporated. The dry residue was purified via silica gel column chromatography (80% EtOAc in cyclohexane containing 3% triethylamine) to give the title compound 1c (901 mg, 81%) as a clear oil. Rf: 0.9 (EtOAc). $^1H$ NMR $^{13}C$ NMR $^{31}P$ NMR and HR-ESI-QToF MS are in conformity with the structure.

(2',3',4',6'-Tetra-O-acetyl-β-D-galactopyranosyl)-thymine 20:

N,O-Bis(trimethylsilyl) acetamide (BSA) (1.5 mL, 6.1 mmol) was added to a suspension of thymine (327 mg, 2.6 mmol) and galactose penta-O-acetate (1.09 g, 2.56 mmol) in dichloroethane (25 mL). The mixture was stirred under argon at ambient temperature for 20 min. After addition of TMSOTf (2.2 mL, 12.1 mmol) the reaction mixture was heated under reflux for 2 h30. The resultant mixture was cooled to ambient temperature and the solvents were evaporated in vacuum to give an oil, which was diluted in ethyl acetate (100 mL) and washed with an aqueous saturated solution of $NaHCO_3$ (100 mL) and brine (2×100 mL). After drying with $Na_2SO_4$, filtered and concentrated, the resultant oil was purified by silica gel column chromatography (EtOAc/cyclohexane, 8:2, v/v) to afford the desired compound 20 (782 mg, 67%) as a white foam. $^1H$ NMR $^{13}C$ NMR and HR-ESI-QToF MS are in conformity with the structure.

1-(2',3',4',6'-Tetra-O-acetyl-β-D-galactopyranosyl)-3-(4-bromobutyl)thymine 21

A solution of (2',3',4',6'-tetra-O-acetyl-β-D-galactopyranosyl)-thymine 20 (350 mg, 0.77 mmol) in anhydrous dimethylformamide (4 mL) was stirred for 5 minutes with potassium carbonate (318 mg, 2.30 mmol). Then, was added 1,4-dibromobutane (919 μL, 7.70 mmol) and the mixture was boiled under reflux for 4 h and at 70° C. overnight. The reaction mixture was then concentrated to give an oil, which was diluted in dichloromethane (20 mL) and washed with an aqueous saturated solution of $NaHCO_3$ (20 mL) and brine (2×20 mL). The organic layer was dried ($Na_2SO_4$), filtered and concentrated. The crude product was purified by silica gel column chromatography (EtOAc/cyclohexane, 4:6) to afford the desired compound 21 (270 mg, 59%) as a pale yellow foam. $^1H$ NMR $^{13}C$ NMR and HR-ESI-QToF MS are conform to the structure.

1-(2',3',4',6'-Tetra-O-acetyl-β-D-galactopyranosyl)-3-(4-azidobutyl)thymine 4f

A solution of 21 (231 mg, 0.39 mmol) in anhydrous dimethylformamide (3 mL) was stirred at 100° C. for 24 h with sodium azide (203 mg, 3.12 mmol). After addition of dichloromethane (10 mL), the reaction was washed with brine (3×20 mL). The organic layer was dried ($Na_2SO_4$), filtered and concentrated to afford the desired product (214 mg, 99%) as a colorless oil. $^1H$ NMR $^{13}C$ NMR and HR-ESI-QToF MS are conform to the structure.

Immobilization on Azide Solid Support 5 of 1-O-Propargyl Hexoses by Cu(I)-Catalyzed Alkyne Azide 1,3-Dipolar Cycloaddition. An aqueous solution of 1-O-propargyl hexose (α-mannose 6, β-galactose, β-glucose) (100 mM, 175 μL), freshly prepared aqueous solutions of $CuSO_4$ (100 mM, 14 μL) and sodium ascorbate (500 mM, 14 μL), water (147 μL) and MeOH (350 μL) were added to 3.5 μmol of azide solid support 5. The resulting mixture was treated in a sealed tube with a microwave synthesizer at 60° C. for 45 min (premixing time: 30 s). The temperature was monitored with an internal infrared probe. The solution was removed, and CPG beads were washed with $H_2O$ (3×2 mL), MeOH (3×2 mL) and $CH_3CN$ (3×2 mL), and dried affording solid-supported hexose.

General Procedure for Introduction of Alkynyl or Bromohexyl Phosphoramidites on Hexose Hydroxyls. Solid-supported hexose derivatives (1 μmol scale) were treated by phosphoramidite chemistry, on a DNA synthesizer, with alkynyl phosphoramidites or 6-bromohexyl phosphoramidite 2. Only coupling and oxidation steps were performed. For the coupling step, benzylmercaptotetrazole was used as activator (0.3 M in anhydrous $CH_3CN$) and phosphoramidite 1, 2 or 1a-e (0.2 M in anhydrous $CH_3CN$), was introduced three times (120 μmol) with a 180 s coupling time. Oxidation was performed with commercial solution of iodide (0.1 M $I_2$, THF/pyridine/water 90:5:5) for 15 s.

General Procedure for Azidation. The solid-supported oligonucleotides bearing the tetrabromohexyl hexoses (1 μmol) were treated with a solution of TMG-$N_3$ (31.6 mg, 200 equiv) and NaI (30 mg, 200 equiv) in DMF (1 mL) for 1 h at 65° C. The beads were washed with DMF (3×2 mL), $H_2O$ (3×2 mL) and $CH_3CN$ (3×2 mL) and then dried by flushing with argon.

General Procedure for Elongation of DNA Sequences and Labeling with Cy3. The DNA sequences were synthesized on the solid-supported scaffolds at the 1 μmol-scale on a DNA synthesizer (ABI 394) by standard phosphoramidite chemistry. For the coupling step, benzylmercaptotetrazole was used as activator (0.3 M in anhydrous $CH_3CN$), commercially available nucleosides phosphoramidites (0.09 M in anhydrous $CH_3CN$) were introduced with a 20 s coupling time and Cy3 amidite (0.06 M in anhydrous $CH_3CN$) with a 180 s coupling time. The capping step was performed with acetic anhydride using commercial solution (Cap A: $Ac_2O$/pyridine/THF, 10:10:80 and Cap B: 10% N-methylimidazole in THF) for 15 s. Each oxidation was performed for 15 s. Detritylation was performed with 2.5% DCA in CH$_2$Cl$_2$ for 35 s.

General Procedure for Deprotection of Solid-supported Oligonucleotides.

The CPG beads bearing modified oligonucleotides were transferred to a 4 mL screw top vial and treated with 2 mL of concentrated aqueous ammonia for 15 h at room temperature and warmed to 55° C. for 2 h. For each compound, the supernatants were withdrawn and evaporated to dryness. Residues were dissolved in water.

General Procedure for the Elongation by Hydrogenophosphonate Chemistry

Elongation was performed on a DNA synthesizer (ABI 394) using a H-phosphonate chemistry cycle starting from a 1,3-propanediol solid support (1 μmol). The detritylation step was performed with 2.5% DCA in CH$_2$Cl$_2$ for 35 s. Then DiMethanolCycloHexane (DMCH) H-phosphonate monoester 9 (Bouillon et al. (2006), J. Org. Chem. 71, 4700-4702) or commercially available thymidine H-phosphonate monoester (60 mM in anhydrous CH$_3$CN/C$_5$H$_5$N 1:1 v/v) and pivaloyl chloride as activator (200 mM in anhydrous CH$_3$CN/C$_5$H$_5$N 1:1 v/v) were passed 6 times through the column alternatively for 5 s, (30 molar excess). The cycle was repeated as required to afford the desired scaffolds with 2 to 5 DMCH motifs or 4 dT motifs.

General Procedure for Amidative Oxidation

The solid-supported H-phosphonate diesters scaffolds (1 μmol) were treated back and forth using two syringes, with 2 mL of a solution of 10% of propargylamine in CCl$_4$/C$_5$H$_5$N (1:1 v/v) for 30 min. The CPG beads were washed with C$_5$H$_5$N (2×2 mL) and CH$_3$CN (3×2 mL) and then dried by flushing with argon. Then the elongation of the oligonucleotides and labeling with Cy3 was performed by phosphoramidite chemistry as described above.

General Procedure for CuAAC Reaction

Procedure for Introduction of Azide D-Galactose Derivatives 4a-f: To a solution of 5'-fluorescent-3'-alkyne oligonucleotide (100 nmol in 100 μL of H$_2$O) were added azid galacoses 4a-f (3 equiv. per alkyne function, 100 mM in MeOH), 1 mg of Cu(0) nanopowder, triethylammonium acetate buffer 0.1 M, pH 7.7 (25 μL), water and MeOH to obtain a final volume of 250 μL (water MeOH, 1:1, v/v). The tube containing the resulting preparation was sealed and placed in a microwave synthesizer Initiator from Biotage with a 30 s premixing time at 60° C. for 60 min.

Procedure for Introduction of
1-O-propargyl-D-Galactose 3

To a solution of 5'-fluorescent-3'-hexose-centered tetra azidohexyl oligonucleotide (100 nmol in 100 μL of H$_2$O) were added 1-O-propargyl 2,3,4-tri-O-acetyl-D-Galactose 3 (5 equiv. per azide function, 100 mM in MeOH), 1 mg of Cu(0) nanopowder, triethylammonium acetate buffer 0.1 M, pH 7.7 (25 μL), water and MeOH to obtain a final volume of 250 μL (water MeOH, 1:1, v/v). The tube containing the resulting preparation was sealed and placed in an oil bath with magnetic stirring at 60° C. for 60 min.

1-(4-Nitro-benzyl)-2,3,4,6-tetra-O-acetyl-β-D-galactopyranoside 8: Under nitrogen atmosphere, at 0° C. boron trifluoride diethyl etherate (1.5 mL, 12 mmol) was added dropwise into a solution of β-D-galactose pentaacetate (1.561 g, 4 mmol) and p-nitrobenzyl alcohol (1.225 g, 8 mmol) in 20 mL of CH2Cl2. After a few minutes, the mixture was heated to reflux and was kept stirring for 7 h. The reaction was then quenched with water and extracted with CH2Cl2. The CH2Cl2 layer was collected, dried with Na2SO4, and concentrated under vacuum. The resulting residue was purified by silica gel column chromatography (0 to 15% AcOEt in cyclohexane) to give the product as a white solid (1.148 g, 59%). Rf=0.36 (AcOEt/cyclohexane, 1:1, v/v). 1H NMR (600 MHz, CDCl3) δ ppm: 8.21 (d, J=8.9 Hz, 2H, H-10, H-12), 7.47 (d, J=8.9 Hz, 2H, H-9, H-13), 5.42 (dd, J=3.4 and 0.8 Hz, 1H, H-4), 5.32 (dd, J=10.5 and 7.9 Hz, 1H, H-2), 5.04 (dd, J=10.5 and 3.4 Hz, 1H, H-3), 5.02-4.72 (2×d, J=13.2 Hz, 2H, H-7), 4.60 (d, J=7.9 Hz, 1H, H-1), 4.21 (dd, J=11.2 and 6.5 Hz, 1H, H-6), 4.15 (dd, J=11.2 and 6.5 Hz, 1H, H-6), 3.94 (dt, J=0.8 and 6.5 Hz, 1H, H-5), 2.17 (s, 3H, CH3CO), 2.06 (s, 6H, 2×CH3CO), 1.99 (s, 3H, CH3CO). 13C NMR (151 MHz, CDCl3) δ ppm: 170.5, 170.3, 170.2, 169.5 (4×CO-Ac), 147.7 (C-11), 144.6 (C-8), 127.7 (C-9), 123.8 (C-10), 100.8 (C-1), 71.1 (C-5), 70.9 (C-3), 69.6 (C-7), 68.9 (C-2), 67.1 (C-4), 61.4 (C-6), 20.9, 20.8, 20.8, 20.7 (4×CH3-Ac). HRMS (ESI+): calculated for C21H25NO12Na [M+Na]+ 506.1274, found 506.1282. [α]D20=−19.1° (c 0.9, MeOH).

General procedure for the hydrogenolysis (Method A). Compound 8 or 91, 2 or 103, 4 was dissolved in distilled CH2Cl2 to which was added 10% palladium on charcoal (10% w/w). Hydrogen gas was bubbled into the reaction mixture until starting materials disappeared as judged by tlc. The reaction mixture was filtered over a celite pad and washed with CH2Cl2. The crude products were purified by silica gel flash column chromatography to afford the desired product.

General procedure for the synthesis of 4-bromoacetamido-aryl-2,3,4,6-tetra-O-acetyl-β-D-galactopyranoside (Method B). A solution of 11 or 12 (1 eq.) in distilled CH2Cl2 was flushed with argon, cooled to 0° C., and Et3N (1.4 eq.) was added. Bromoacetyl bromide (1.3 eq.) was added dropwise and the mixture was stirred for 1 h at 0° C. The mixture was allowed to warm up at rt for 1 h. The crude mixture in CH2Cl2 was washed with HCl 1N (2×25 mL), water (2×25 mL) and brine (25 mL). After drying (Na2SO4), concentration and total removal of CH2Cl2 under vacuum, the residue was purified by silica gel column chromatography to afford the desired product.

General procedure for the synthesis of 4-azidooacetamido-aryl-2,3,4,6-tetra-O-acetyl-β-D-galactopyranoside (Method C). A solution of 14 or 15 or 16 (1 eq.) and TMGN3 (3 eq.) in anhydrous CH3CN was stirred at 80° C. for 15 minutes under microwave assistance. After concentration under vacuum, the residue was purified by silica gel column chromatography to afford the desired product.

General procedure for deacetylation of carbohydrates (method D). The acetylated glycoside (4-(azidoacetamide) phenyl-β-D-galactoside, 5 17-19 and 28-29) was suspended in MeOH or 1,4-dioxane and ammonia solution 30% was added (1:1, v/v). The mixture was stirred under Argon at room temperature for 6 hours to 1 day. Solvent was evaporated under vacuum to afford the desired product.

General procedure for glycosidation (Method E). To a solution of 7 (1 eq.), 22 or 23 (2 eq.), and tetrabutylammoniumhydrogensulfate (1 eq.) in CH2Cl2 at 0° C. a 1 M aq. solution of NaOH was added. The biphasic mixture was stirred at rt for 36 h, then diluted with CH2Cl2, washed with NaOH 1M (2×30 mL) and dried over Na2SO4. The solvent was removed under reduced pressure and the crude product was purified by silica gel column chromatography to afford the desired product.

General procedure for azidation of biarylgalactopyranosides (Method F).): 26 or 27 (1 eq.) was dissolved in anhydrous DMF, followed by the addition of 1-ethyl-3-(3'- dimethylaminopropyl)carbodiimide (1.6 eq.) and hydroxybenzotriazole (1.1 eq.). 3-Azidopropylamine (2 eq.) was added and the reaction was stirred at room temperature for 12 h. The reaction was concentrated then quenched with water and extracted with DCM. The organic layer was dried with sodium sulfate, concentrated and purified by silica gel column chromatography to afford the desired product.

1-(4-Amino-benzyl)-2,3,4,6-tetra-O-acetyl-β-D-galactopyranoside 11

Obtained as a white solid (412 mg, 45%) following Method A: 8 (968 mg, 2.00 mmol), Pd/C 10% (96.8 mg), in distilled CH2Cl2 (30 mL). The mixture was worked up, aqueous layer was extracted with CH2Cl2 and the crude product was purified on silica gel (0 to 5% MeOH in CH2Cl2) to afford the pure product. Rf=0.43 (AcOEt/cyclohexane, 6:4, v/v). 1H NMR (600 MHz, CDCl3) δ ppm: 7.02 (d, J=8.1 Hz, 2H, H-10, H-12), 6.60 (d, J=8.1 Hz, 2H, H-9, H-13), 5.32 (d, J=3.3 Hz, 1H, H-4), 5.18 (dd, J=10.4 and 8.3 Hz, 1H, H-2), 4.91 (dd, J=10.4, 3.3, 1H, H-3), 4.71-4.46 (2×d, J=11.9, 2H, H-7), 4.42 (d, J=7.9 Hz, 2H, H-1), 4.15 (dd, J=11.2 and 6.5 Hz, 1H, H-6), 4.10 (dd, J=11.2 and 6.5 Hz, 1H, H-6), 3.81 (t, J=6.5, 1H, H-5), 2.09 (s, 3H, CH3CO), 2.01 (s, 3H, CH3CO), 1.94 (s, 3H, CH3CO), 1.91 (s, 3H, CH3CO). 13C NMR (151 MHz, CDCl3) δ ppm: 170.5, 170.4, 170.2, 169.5 (4 CO Ac), 146.6 (C-11), 129.8 (C-8), 126.3 (C-9), 115.0 (C-10), 99.2 (C-1), 71.1 (C-5), 70.8 (C-3), 70.7 (C-7), 69.0 (C-2), 67.3 (C-4), 61.5 (C-6), 20.8, 20.8, 20.7, 20.6 (4 CH3CO). HRMS (ESI+): calculated for C21H28NO10 [M+H]+454.1713, found 454.1718. [α]D20=−25.0° (c 0.4, MeOH).

4-Amino-benzyl-1-thio-2,3,4,6-tetra-O-acetyl-β-D-galactopyranoside 12

Obtained as a colorless oil (314 mg, 79%) following Method A: 9 (425 mg, 0.851 mmol), Pd/C 10% (42.5 mg), in distilled CH2Cl2 (15 mL). The mixture was worked up, aqueous layer was extracted with CH2Cl2 and the crude product was purified on silica gel (0 to 5% MeOH in CH2Cl2) to afford the pure product. Rf=0.26 (AcOEt/cyclohexane, 6:4, v/v). 1H NMR (600 MHz, CDCl3) δ ppm: 7.08 (d, J=8.1 Hz, 2H, H-9, H-13), 6.63 (d, J=8.1 Hz, 2H, H-10, H-12), 5.40 (d, J=3.3 Hz, 1H, H-4), 5.26 (t, J=9.9 Hz, 1H, H2), 4.96 (dd, J=9.9 and 3.3 Hz, 1H, H-3), 4.27 (d, J=9.9 Hz, 1H, H-1), 4.17 (dd, J=11.3 and 6.6 Hz, 1H, H-6), 4.11 (dd, J=11.3 and 6.6 Hz, 1H, H-6), 3.86 (d, J=12.9 Hz, 1H, H-7), 3.81 (t, J=6.6 Hz, 1H, H-5), 3.75 (d, J=12.9 Hz, 1H, H-7), 2.14 (s, 3H, CH3CO), 2.06 (s, 3H, CH3CO), 2.01 (s, 3H, CH3CO), 1.96 (s, 3H, CH3CO). 13C NMR (151 MHz, CDCl3) δ ppm: 170.5, 170.4, 170.2, 169.7 (4 CO Ac), 145.8 (C-11), 130.3 (C-9), 126.5 (C-8), 115.3 (C-10), 82.5 (C-1), 74.5 (C-5), 72.0 (C-3), 67.5 (C-4), 67.3 (C-2), 61.8 (C-6), 33.7 (7), 20.9, 20.8, 20.8, 20.7 (4 CH3CO). HRMS (ESI+): calculated for C21H28NO9S [M+H]+ 470.1485, found 470.1489. [α]D20=−73.8° (c 1.0, MeOH).

4-Bromoacetamidobenzyl-2,3,4,6-tetra-O-acetyl-β-D-galactopyranoside 14

Obtained as a pale yellow oil (238 mg, 79%) following Method B: 11 (239 mg, 0.527 mmol), Et3N (0.103 mL, 0.738 mmol), bromoacetyl bromide (0.059 mL, 0.685 mmol) in distilled CH2Cl2 (30 mL). The mixture was worked up, and the crude product was purified on silica gel (0 to 60% AcOEt in cyclohexane) to afford the desired product. Rf=0.31 (AcOEt/cyclohexane, 6:4, v/v). 1H NMR (600 MHz, CDCl3) δ ppm: 8.23 (s, 1H, H-14), 7.51 (d, J=8.4 Hz, 2H, H-10, H-12), 7.26 (d, J=8.4 Hz, 2H, H-9, H-13), 5.37 (dd, J=3.4 and 0.9 Hz, 1H, H-4), 5.25 (dd, J=10.4 and 7.9 Hz, 1H, H-2), 4.97 (dd, J=10.4 and 3.4 Hz, 1H, H-3), 4.85-4.59 (2×d, J=12.2 Hz, 2H, H-7), 4.50 (d, J=7.9 Hz, 1H, H-1), 4.19 (dd, J=11.2 and 6.5 Hz, 1H, H-6), 4.13 (dd, J=11.2 and 6.5 Hz, 1H, H-6), 3.99 (s, 2H, H-16), 3.88 (dt, J=0.9 and 6.5 Hz, 1H, H-5), 2.13 (s, 3H, CH3CO), 2.04 (s, 3H, CH3CO), 2.00 (s, 3H, CH3CO), 1.96 (s, 3H, CH3CO). 13C NMR (151 MHz, CDCl3) δ ppm: 170.6, 170.4, 170.3, 169.6 (4×CO-Ac), 163.8 (C-15), 137.0 (C-11), 133.7 (C-8), 128.7 (C-9), 120.2 (C-10), 100.0 (C-1), 71.1 (C-3), 71.0 (C-5), 70.4 (C-7), 69.0 (C-2), 67.3 (C-4), 61.5 (C-6), 29.6 (C-16), 20.9, 20.8, 20.8, 20.7 (4×CH3-Ac). HRMS (ESI+): calculated for C23H29BrNO11 [M+H]+ 574.0924, found 574.0933. [α]D20=−13.1° (c 2.6, MeOH).

4-Bromoacetamidobenzyl-1-thio-2,3,4,6-tetra-O-acetyl-β-D-galactopyranoside 15

Obtained as a yellow oil (367 mg, 93%) following Method B: 12 (314 mg, 0.669 mmol), Et3N (0.130 mL, 0.937 mmol), bromoacetyl bromide (0.075 mL, 0.869 mmol) in distilled CH2Cl2 (10 mL). The mixture was worked up, and the crude product was purified on silica (0 to 40% AcOEt in cyclohexane) to afford the desired product. Rf=0.28 (AcOEt/cyclohexane, 1:1, v/v). 1H NMR (600 MHz, CDCl3) δ ppm: 8.23 (s, 1H, H-14), 7.47 (d, J=8.5 Hz, 2H, H-10, H-12), 7.26 (d, J=8.5 Hz, 2H, H-9, H-13), 5.37 (dd, J=3.3 and 0.8 Hz, 1H, H-4), 5.23 (t, J=10.0 Hz, 1H, H-2), 4.94 (dd, J=10.0 and 3.4 Hz, 1H, H-3), 4.25 (d, J=10.0 Hz, 1H, H-1), 4.12 (dd, J=11.4 and 6.7 Hz, 1H, H-6), 4.05 (dd, J=11.4 and 6.4 Hz, 1H, H-6), 3.98 (s, 2H, H-16), 3.90, 3.81 (2×d, J=13.0 Hz, each 1H, H-7), 3.78 (m, 1H, H-5), 2.12 (s, 3H, CH3CO), 2.03 (s, 3H, CH3CO), 1.99 (s, 3H, CH3CO), 1.93 (s, 3H, CH3CO). 13C NMR (151 MHz, CDCl3) δ ppm: 170.6, 170.4, 170.2, 169.8 (4 CO Ac), 163.74 (C-15), 136.4 (C-11), 133.9 (C-8), 130.0 (C-9), 120.3 (C-10), 82.6 (C-1), 74.6 (C-5), 72.0 (C-3), 67.5 (C-4), 67.3 (C-2), 61.7 (C-6), 33.4 (C-7), 29.6 (C-16), 20.9, 20.8, 20.8, 20.7 (4 CH3CO). HRMS (ESI+): calculated for C23H29NO10BrS [M+H]+ 590.0696, found 590.0688. [α]D20=−56.7° (c 2.0, MeOH).

4-Bromoacetamidophenyl-1-thio-2,3,4,6-tetra-O-acetyl-β-D-galactopyranoside 16

A solution of 10 (497 mg, 1.02 mmol) in anhydrous CH2Cl2 (20 mL) was degassed then Pd/C 10% (49.7 mg) was added. The solution was subjected to hydrogen atmosphere and stirred at rt for 3 days. After total disappearance of starting material, the mixture of 13 was flushed with argon, cooled to 0° C., and Et3N (0.043 mL, 0.308 mmol) was added. Bromoacetyl bromide (0.025 mL, 0.286 mmol) was added dropwise and the mixture was stirred for 1 h at 0° C. The mixture was allowed to warm up at rt for 1 h then was filtered through a plug of celite and washed with CH2Cl2. The crude mixture in CH2Cl2 was washed with HCl 1N (2×25 mL), water (2×25 mL) and brine (25 mL). After drying (Na2SO4), concentration and total removal of CH2Cl2 with vacuum, the residue was purified by silica gel column chromatography (0 to 30% AcOEt in cyclohexane) to give the product as a yellow oil (505.6 mg, 86% total). Rf=0.33 (AcOEt/cyclohexane, 6:4, v/v). 1H NMR (600 MHz, CDCl3) δ ppm: 8.15 (s, 1H, H-13), 7.52 (m, 2H, H-9, H-11), 7.51 (m, 2H, H-8, H-12), 5.40 (dd, J=3.3 and 0.8 Hz, 1H, H-4), 5.19 (t, J=9.9 Hz, 1H, H-2), 5.04 (dd, J=9.9 and 3.3 Hz, 1H, H-3), 4.65 (d, J=9.9 Hz, 1H, H-1), 4.17 (dd, J=11.4 and 6.9 Hz, 1H, H-6), 4.11 (dd, J=11.4 and 6.9 Hz, 1H, H-6), 4.01 (s, 2H, H-15), 3.91 (dt, J=0.8 and 6.9 Hz 1H, H-5), 2.11 (s, 3H, CH3CO), 2.09 (s, 3H, CH3CO), 2.05 (s, 3H, CH3CO), 1.96 (s, 3H, CH3CO). 13C NMR (151 MHz, CDCl3) δ ppm: 170.5, 170.3, 170.2, 169.5 (4 CO Ac), 163.5 (C-14), 137.4 (C-10), 134.3 (C-8), 128.2 (C-7), 120.3 (C-9), 86.7 (C-1), 74.7 (C-5), 72.1 (C-3), 67.4 (C-4), 61.7 (C-6), 29.5 (C-15), 21.0, 20.8, 20.8, 20.7 (4 CH3CO). HRMS (ESI+): calculated forC22H26NO10NaSBr [M+Na]+ 598.0358, found 598.0360. [α]D20=−13.0° (c 2.2, MeOH).

4-Azidoacetamidobenzyl-2,3,4,6-tetra-O-acetyl-β-D-galactopyranoside 17

Obtained as a white solid (148 mg, 94%) following Method C: 14 (168 mg, 0.292 mmol), TMGN3 (138.6 mg, 0.876 mmol) in anhydrous CH3CN (4 mL). The mixture was worked up and the crude product was purified on silica gel (0 to 40% AcOEt in cyclohexane) to afford the desired product. Rf=0.28 (AcOEt/cyclohexane, 1:1, v/v). 1H NMR (600 MHz, CDCl3) δ ppm: 8.05 (s, 1H, H-14), 7.50 (d, J=8.8 Hz, 2H, H-10, H-12), 7.24 (d, J=8.8 Hz, 2H, H-9, H-13), 5.35 (d, J=3.4 Hz, 1H, H-4), 5.23 (dd, J=10.4 and 7.9 Hz, 1H, H-2), 4.95 (dd, J=10.4 and 3.4 Hz, 1H, H-3), 4.83 (d, J=12.2 Hz, 1H, H-7), 4.57 (d, J=12.2 Hz, 1H, H-7), 4.48 (d, J=7.9 Hz, 1H, H-1), 4.17 (dd, J=11.2 and 6.4 Hz, 1H, H-6), 4.13 (dd, J=11.2 and 6.4 Hz, 1H, H-6), 4.10 (s, 2H, H-16), 3.85 (t, J=6.4 Hz, 1H, H-5), 2.12 (s, 3H, CH3CO), 2.03 (s, 3H, CH3CO), 1.98 (s, 3H, CH3CO), 1.94 (s, 3H, CH3CO). 13C NMR (151 MHz, CDCl3) δ ppm: 170.4, 170.3, 170.1, 169.4 (4 CO Ac), 164.6 (C-15), 136.6 (C-11), 133.4 (C-8), 128.6 (C-9), 120.0 (C-10), 99.8 (C-1)), 70.9 (C-3), 70.8 (C-5), 70.2 (C-7), 68.9 (C-2), 67.1 (C-4), 61.3 (C-6), 53.0 (C-16), 20.8, 20.7, 20.7, 20.6 (4 CH3CO). HRMS (ESI+): calculated for C23H29N4O11 [M+H]+ 537.1833, found 537.1840. [α]D20=−18.0° (c 1.0, MeOH).

4-Azidoacetamidobenzyl-β-D-galactopyranoside 3

HRMS (ESI+): calculated for C15H21N4O7 [M+H]+ 369.1410, found 369.1411.

4-Azidoacetamidobenzyl-1-thio-2,3,4,6-tetra-O-acetyl-β-D-galactopyranoside 18. Obtained as light brown crystals (99 mg 94%) following Method C: starting for 15 (112 mg, 0.190 mmol), TMGN3 (90.2 mg, 0.570 mmol) in anhydrous CH3CN (5 mL). The mixture was worked up and the crude product was purified on silica gel (0 to 40% AcOEt in cyclohexane) to afford the desired product Rf=0.26 (AcOEt/cyclohexane, 1:1, v/v). 1H NMR (600 MHz, CDCl3) δ ppm: 8.20 (s, 1H, H-14), 7.50 (d, J=8.4 Hz, 2H, H-10, H-12), 7.27 (d, J=8.4 Hz, 2H, H-9, H-13), 5.39 (d, J=3.3 Hz, 1H, H-4), 5.25 (t, J=10.0 Hz, 1H, H2), 4.96 (dd, J=10.0 and 3.3 Hz, 1H, H-3), 4.28 (d, J=10.0 Hz, 1H, H-1), 4.13 (dd, J=11.4 and 6.7 Hz, 1H, H-6), 4.10 (s, 2H, H-16), 4.07 (dd, J=11.4 and 6.7 Hz, 1H, H-6), 3.92, 3.81 (2×d, J=13.0 Hz, each 1H, H-7), 3.80 (d, J=6.7 Hz, 1H, H-5), 2.14 (s, 3H, CH3CO), 2.05 (s, 3H, CH3CO), 2.01 (s, 3H, CH3CO), 1.95 (s, 3H, CH3CO). 13C NMR (101 MHz, CDCl3) δ ppm: 170.4, 170.3, 170.1, 169.7 (4CO Ac), 164.9 (C-15), 136.1 (C-11), 133.6 (C-8), 129.8 (C-9), 120.2 (C-10), 82.4 (C-1), 74.4 (C-5), 71.2 (C-3), 67.4 (C-4), 67.09 (C-2), 61.6 (C-6), 52.90 (C-16), 33.3 (C-7), 20.8, 20.7, 20.7, 20.6 (4 CH3CO). HRMS (ESI+): calculated for C23H29N4O10S [M+H]+ 553.1604, found 553.1621. [α]D20=−53.4° (c 1.0, MeOH).

4-Azidoacetamidobenzyl-1-thio-β-D-galactopyranoside 4

HRMS (ESI+): calculated for C15H21N4O6S [M+H]+ 385.1182, found 385.1185.

4-Azidoacetamidophenyl-1-thio-2,3,4,6-tetra-O-acetyl-β-D-galactopyranoside (19)

Obtained as colorless oil (56 mg 55%) following Method C: 16 (109 mg, 0.189 mmol), TMGN3 (89.7 mg, 0.567 mmol) in anhydrous CH3CN (4 mL). The mixture was worked up and the crude product was purified on silica gel (0 to 40% AcOEt in cyclohexane) to afford the desired product Rf=0.28 (AcOEt/cyclohexane, 6:4, v/v). 1H NMR (600 MHz, CDCl3) δ ppm: 8.08 (s, 1H, H-13), 7.51 (m, 2H, H-9, H-11), 7.49 (m, 2H, H-8, H-12), 5.39 (dd, J=3.3 and 0.9 Hz, 1H, H-4), 5.18 (t, J=9.9 Hz, 1H, H-2), 5.03 (dd, J=9.9 and 3.3 Hz, 1H, H-3), 4.64 (d, J=9.9 Hz, 1H, H-1), 4.16 (dd, J=11.4 and 6.9 Hz, 1H, H-6), 4.13 (s, 2H, H-15), 4.09 (dd, J=11.4 and 6.9 Hz, 1H, H-6), 3.90 (dt, J=0.8 and 6.69 Hz, 1H, H-5), 2.10 (s, 3H, CH3CO), 2.08 (s, 3H, CH3CO), 2.03 (s, 3H, CH3CO), 1.95 (s, 3H, CH3CO). 13C NMR (151 MHz, CDCl3) δ ppm: 170.5, 170.3, 170.1, 169.5 (4 CO Ac), 164.7 (C-14), 137.3 (C-10), 134.2 (C-8), 128.0 (C-7), 120.4 (C-9), 86.7 (C-1), 74.6 (C-5), 72.1 (C-3), 67.4 (C-4), 61.7 (C-6), 53.08 (C-15), 20.9, 20.8, 20.7, 20.7 (4 CH3CO). HRMS (ESI+): calculated for C22H27N4O10S [M+H]+ 539.1448, found 539.1450. [α]D20=−12.3° (c 1.3, MeOH).

4-Azidoacetamidophenyl-1-thio-β-D-galactopyranoside 2

HRMS (ESI+): calculated for C14H19N4O6S [M+H]+ 371.1025, found 371.1031.

Benzyl 4'-(2,3,4,6-tetra-O-acetyl-β-D-galactopyranosyloxy)-biphenyl-4-carboxylate 24

Obtained as a white solid (2.189 g, 99%) following Method E: 7 (1.439 g, 3.5 mmol), benzyl 4'-hydroxy-biphenyl-4-carboxylate 226 (2.464 g, 7.05 mmol), tetrabutylammoniumhydrogensulfate (1.188 g, 3.5 mmol) in distilled CH2Cl2 (15 mL), a 1 M aq. solution of NaOH (5 mL). The mixture was worked up and the crude product was purified on silica gel (0 to 30% AcOEt in cyclohexane) to afford the desired product Rf=0.39 (AcOEt/cyclohexane, 1:1, v/v). 1H NMR (600 MHz, CDCl3) δ ppm: 8.13 (d, J=8.5 Hz, 2H, H-13, H-15), 7.60 (d, J=8.5 Hz, 2H, H-12, H-16), 7.56 (d, J=8.8 Hz, 2H, H-9, H-17), 7.46 (d, J=7.2 Hz, 2H, H-22, H-26), 7.40 (t, J=7.2 Hz, 2H, H-23, H-25), 7.34 (t, J=7.2 Hz, 1H, H-24), 7.10 (d, J=8.8 Hz, 2H, H-8, H-18), 5.52 (dd, J=10.4 and 8.0 Hz, 1H, H-2), 5.48 (dd, J=3.4 and 0.8 Hz, 1H, H-4), 5.39 (s, 2H, H-20), 5.14 (dd, J=10.4 and 3.4 Hz, 1H, H-3), 5.11 (d, J=8.0 Hz, 1H, H-1), 4.25 (dd, J=11.2 and 7.0 Hz, 1H, H-6), 4.18 (dd, J=11.2 and 6.4 Hz, 1H, H-6), 4.09 (ddd, J=7.0 and 6.4 and 0.8 Hz, 1H, H-5), 2.19 (s, 3H, COCH3), 2.08 (s, 3H, COCH3), 2.07 (s, 3H, COCH3), 2.02 (s, 3H, COCH3). 13C NMR (151 MHz, CDCl3) δ ppm: 170.4, 170.3, 170.2, 169.5 (4 CO Ac), 166.4 (C-19), 157.2 (C-7), 145.1 (C-11), 136.3 (C-21), 135.3 (C-10), 130.4 (C-13), 128.9 (C-14), 128.7 (C-23), 128.6 (C-9), 128.4 (C-24), 128.3 (C-22), 126.9 (C-12), 117.5 (C-8), 99.7 (C-1), 71.3 (C-5), 71.0 (C-3), 68.8 (C-2), 67.0 (C-4), 66.8 (C-20), 61.5 (C-6), 20.9, 20.8, 20.7, 20.6 (4

4'-(2,3,4,6-tetra-O-acetyl-β-D-galactopyranosyloxy)-biphenyl-4-carboxylic acid 26

Obtained as a white solid (691 mg, 37%) following Method A: 24 (2.189 g, 3.45 mmol), Pd/C 10% (219 mg), in distilled CH2Cl2 (30 mL). The mixture was worked up, aqueous layer was extracted with CH2Cl2 and the crude product was purified on silica gel (0 to 50% AcOEt in cyclohexane) to afford the desired product. Rf=0.44 (MeOH/CH2Cl2, 1:9, v/v). 1H NMR (600 MHz, CDCl3) δ ppm: 8.17 (d, J=8.4 Hz, 2H, H-13, H-15), 7.65 (d, J=8.4 Hz, 2H, H-12, H-16), 7.58 (d, J=8.7 Hz, 2H, H-9, H-17), 7.11 (d, J=8.7 Hz, 2H, H-8, H-18), 5.53 (dd, J=10.4 and 7.9 Hz, 1H, H-2), 5.48 (d, J=3.4 Hz, 1H, H-4), 5.15 (dd, J=10.4 and 3.4 Hz, 1H, H-3), 5.12 (d, J=7.9 Hz, 1H, H-1), 4.26 (dd, J=11.4 and 7.0 Hz, 1H, H-6), 4.19 (dd, J=11.4 and 6.4 Hz, 1H, H-6), 4.11 (m, 1H, H-5), 2.20 (s, 3H, COCH3), 2.09 (s, 3H, COCH3), 2.08 (s, 3H, COCH3), 2.03 (s, 3H, COCH3). 13C NMR (151 MHz, CDCl3) δ ppm: 171.3 (C-19), 170.5, 170.4, 170.3, 169.5 (4 CO Ac), 157.3 (C-7), 145.8 (C-11), 135.2 (C-10), 131.0 (C-13), 128.7 (C-9), 127.9 (C-14), 127.0 (C-12), 117.5 (C-8), 99.7 (C-1), 71.3 (C-5), 71.0 (C-3), 68.8 (C-2), 67.0 (C-4), 61.5 (C-6), 20.9, 20.8, 20.7, 20.7 (4 CH3CO). HRMS (ESI+): calculated for C27H28O12Na [M+Na]+ 567.1478, found 567.1489. [α]D20=+6.6° (c 1.1, 1,4-dioxane).

Benzyl 4'-(2,3,4,6-tetra-O-acetyl-β-D-galactopyranosyloxy)-biphenyl-4-carboxylic acid 3-azido-propyl-amide 28

Obtained as a white solid (47 mg, 74%) following Method F: 26 (131 mg, 0.102 mmol), 1-ethyl-3-(3'-dimethylaminopropyl)carbodiimide (25.3 mg, 0.163 mmol), hydroxybenzotriazole (15.1 mg, 0.112 mmol), 3-azidopropylamine (20.4 mg, 0.204 mmol) in anhydrous DMF (5 mL). The mixture was worked up and the crude product was purified on silica gel (0 to 50% AcOEt in cyclohexane) to afford the desired product. Rf=0.34 (MeOH/CH2Cl2, 2:98, v/v). 1H NMR (600 MHz, CDCl3) δ ppm: 7.81 (d, J=8.2 Hz, 2H, H-13, H-15), 7.58 (d, J=8.2 Hz, 2H, H-12, H-16), 7.52 (d, J=8.6 Hz, 2H, H-9, H-17), 7.06 (d, J=8.7 Hz, 2H, H-8, H-18), 6.46 (t, J=5.7 Hz, 1H, H-20), 5.49 (dd, J=10.4 and 8.0 Hz, 1H, H-2), 5.45 (d, J=3.4 Hz, 1H, H-4), 5.11 (dd, J=10.4 and 3.4 Hz, 1H, H-3), 5.08 (d, J=8.0 Hz, 1H, H-1), 4.22 (dd, J=11.3 and 6.7 Hz, 1H, H-6), 4.15 (dd, J=11.3 and 6.7 Hz, 1H, H-6), 4.08 (t, J=6.7 Hz, 1H, H-5), 3.56 (q, J=6.4 Hz, 2H, H-21), 3.44 (t, J=6.4 Hz, 2H, H-23), 2.17 (s, 3H, COCH3), 2.06 (s, 3H, COCH3), 2.04 (s, 3H, COCH3), 2.00 (s, 3H, COCH3), 1.91 (p, J=6.4 Hz, 2H, H-22). 13C NMR (151 MHz, CDCl3) δ ppm: 170.5, 170.3, 170.2, 169.5 (4 CO Ac), 167.4 (C-19), 157.1 (C-7), 143.6 (C-11), 135.3 (C-10), 133.0 (C-14), 128.5 (C-9), 127.6 (C-13), 127.1 (C-12), 117.4 (C-8), 99.7 (C-1), 71.2 (C-5), 70.9 (C-3), 68.8 (C-2), 67.0 (C-4), 61.5 (C-6), 49.8 (C-23), 38.0 (C-21), 28.9 (C-22), 20.9, 20.8, 20.8, 20.7 (4 CH3CO). HRMS (ESI+): calculated for C30H35N4O11 [M+H]+ 627.2302, found 627.2304. [α]D20=+3.8° (c 3.2, 1,4-dioxane).

Benzyl 4'-(β-D-galactopyranosyloxy)-biphenyl-4-carboxylic acid 3-azido-propyl-amide 5

HRMS (ESI+): calculated for C22H27N4O7 [M+H]+ 459.1880, found 459.1884.

Benzyl-6-hydroxy-2-naphthoate 23

To a solution of 6-hydroxy-2-naphthoic acid (1.882 g, 10 mmol), in aqueous methanol 90% (20 mL), Cs2CO3 (1.629 g, 5 mmol) was added. The solution was stirred at room temperature for 30 min. The solvent was evaporated at reduced pressure and then co-evaporated with toluene (2×10 mL). The resulting cesium salt was suspended in anhydrous DMF (10 mL), cooled to 0° C. and benzyl bromide (1.19 mL, 10 mmol) was added. After 1 h stirring, the solution was allowed to warm up to room temperature and stirring was continued for a further 10 h before the solvent was removed under reduced pressure. The residue was taken up into water (2×20 mL) and then extracted with AcOEt (200 mL) and the combined organic layers were dried over Na2SO4 and the solvent removed under reduced pressure. The crude product was purified by silica gel column chromatography (0 to 30% AcOEt in cyclohexane) to give the product as a white solid (2.095 g, 75%). Rf=0.47 (cyclohexane/AcOEt, 1:1, v/v). 1H NMR (600 MHz, CDCl3) δ ppm: 8.57 (d, J=1.7 Hz, 1H, H-5), 8.05 (dd, J=8.6 and 1.7 Hz, 1H, H-7), 7.85 (d, J=8.8 Hz, 1H, H-4), 7.69 (d, J=8.6 Hz, 1H, H-8), 7.50 (d, J=7.3 Hz, 1H, H-14), 7.42 (t, J=7.3 Hz, 1H, H-15), 7.36 (t, J=7.3 Hz, 1H, H-16), 7.18 (d, J=2.4 Hz, 1H), 7.16 (dd, J=8.8 and 2.4 Hz, 1H, H-3), 5.63 (s, 1H, OH), 5.43 (s, 2H, H-12). 13C NMR (151 MHz, CDCl3) δ ppm: 167.1 (C-11), 155.9 (C-2), 137.4 (C-9), 136.3 (C-13), 131.7 (C-4), 131.4 (C-5), 128.8 (C-15), 128.4 (C-16), 128.4 (C-14), 128.0 (C-11), 126.7 (C-8), 126.2 (C-7), 125.2 (C-16), 118.9 (C-3), 109.7 (C-1), 67.1 (C-12). HRMS (ESI+): calcd. for C18H15O3 [M+H]+ 279.1021; found 279.1024.

Benzyl-6-(2,3,4,6-tetra-O-acetyl-β-D-galactopyranosyloxy)-2-naphthoate 25

Obtained as a white solid (1.239 mg, 77%) following Method E: 7 (1.082 g, 2.63 mmol), 23 (1.464 g, 5.26 mmol), tetrabutylammoniumhydrogensulfate (0.823 g, 2.63 mmol) in distilled CH2Cl2 (15 mL), a 1 M aq. solution of NaOH (5 mL). The mixture was worked up and the crude product was purified on silica gel (0 to 30% AcOEt in cyclohexane) to afford the desired product Rf=0.38 (AcOEt/cyclohexane, 1:1, v/v). 1H NMR (600 MHz, CDCl3) δ ppm: 8.59 (d, J=1.6 Hz, 1H, H-12), 8.09 (dd, J=8.7 and 1.6 Hz, 1H, H-10), 7.89 (d, J=8.8 Hz, 1H, H-13), 7.76 (d, J=8.7 Hz, 1H, H-9), 7.49 (d, J=7.2 Hz, 2H, H-20, H-24), 7.41 (t, J=7.2 Hz, 2H, H-21, H-23), 7.37 (d, J=2.4, 1H, H-8), 7.36 (m, 1H, H-22), 7.24 (dd, J=8.8 and 2.4 Hz, 1H, H-14), 5.56 (dd, J=10.4 and 7.9, 1H, H-2), 5.50 (dd, J=3.4 and 0.8 Hz, 1H, H-4), 5.42 (s, 2H, H-18), 5.24 (d, J=7.9 Hz, 1H, H-1), 5.17 (dd, J=10.4 and 3.4 Hz, 1H, H-3), 4.27 (dd, J=11.1 and 6.8 Hz, 2H, H-6), 4.18-4.15 (m, 1H, H-5), 2.20 (s, 3H, COCH3), 2.08 (s, 3H, COCH3), 2.07 (s, 3H, COCH3), 2.03 (s, 3H, COCH3). 13C NMR (151 MHz, CDCl3) δ ppm: 170.5, 170.4, 170.3, 169.6 (4 CO Ac), 166.70 (C-17), 156.7 (C-7), 136.9 (C-15), 136.3 (C-19), 131.5 (C-13), 131.2 (C-12), 129.3 (C-16), 128.9 (C-21), 128.50 (C-20), 127.5 (C-9), 126.6 (C-10), 126.5 (C-11), 119.8 (C-14), 111.2 (C-8), 99.5 (C-1), 71.5 (C-5), 71.0 (C-3), 68.9 (C-2), 67.1 (C-4), 67.1 (C-18), 61.8 (C-6), 20.9, 20.9, 20.9, 20.8 (4 CH3 CO). HRMS (ESI+): calculated for C32H32O12Na [M+Na]+ 631.1791, found 631.1788. [α]D20=−11.2° (c 1.1, MeOH).

6-(2,3,4,6-tetra-O-acetyl-β-D-galactopyranosyloxy)-2-naphthoic acid 27

Obtained as a white solid (806 mg, 76%) following Method A: 25 (1.239 g, 2.04 mmol), Pd/C 10% (124 mg), in distilled CH2Cl2 (15 mL). The mixture was worked up, aqueous layer was extracted with CH2Cl2 and the crude product was purified on silica gel (0 to 50% AcOEt in cyclohexane) to afford the desired product. Rf=0.44 (MeOH/CH2Cl2, 6:94, v/v). 1H NMR (600 MHz, CDCl3) δ ppm: 8.66 (d, J=1.6 Hz, 1H, H-12), 8.11 (dd, J=8.6 and 1.6 Hz, 1H, H-10), 7.93 (d, J=9.0 Hz, 1H, H-13), 7.80 (d, J=8.6 Hz, 1H, H-9), 7.39 (d, J=2.4 Hz, 1H, H-8), 7.27 (dd, J=9.0 and 2.4 Hz, 1H, H-14), 5.57 (dd, J=10.4 and 7.9 Hz, 1H, H-2), 5.51 (d, J=3.5 Hz, 1H, H-4), 5.26 (d, J=7.8 Hz, 1H, H-1), 5.18 (dd, J=10.4 and 3.5 Hz, 1H, H-3), 4.30-4.19 (m, 2H, H-6), 4.19-4.17 (m, 1H, H-5), 2.20 (s, 3H, COCH3), 2.09 (s, 3H, COCH3), 2.08 (s, 3H, COCH3), 2.04 (s, 3H, COCH3). 13C NMR (151 MHz, CDCl3) δ ppm: 171.6 (C-17), 170.6, 170.4, 170.3, 169.6 (4 CO Ac), 157.0 (C-7), 137.3 (C-15), 132.14 (C-12), 131.7 (C-13), 129.3 (C-16), 127.6 (C-9), 126.6 (C-10), 125.6 (C-11), 119.9 (C-14), 111.2 (C-8), 99.5 (C-1), 71.6 (C-5), 71.1 (C-3), 68.9 (C-2), 67.2 (C-4), 61.8 (C-6), 21.0, 20.9, 20.9, 20.8 (4 CH3CO). HRMS (ESI−): calculated for C25H25O12 [M−H]− 517.1346, found 517.1344. [α]D20=−6.4° (c 1.1, MeOH).

6-(2,3,4,6-tetra-O-acetyl-β-D-galactopyranosyloxy)-2-naphthoic acid 3-azido-propyl-amide 29

Obtained as a white solid (182 mg, 79%) following Method F: 27 (200 mg, 0.386 mmol), 1-ethyl-3-(3'-dimethylaminopropyl)carbodiimide (96 mg, 0.618 mmol), hydroxybenzotriazole (57.4 mg, 0.425 mmol), 3-azidopropylamine (77.3 mg, 0.772 mmol) in anhydrous DMF (5 mL). The mixture was worked up and the crude product was purified on silica gel (0 to 50% AcOEt in cyclohexane) to afford the desired product. Rf=0.32 (MeOH/CH2Cl2, 2:98, v/v). 1H NMR (600 MHz, CDCl3) δ ppm: 7.83 (d, J=9.0 Hz, 1H, H-13), 7.80 (dd, J=8.5 and 1.5 Hz, 1H, H-10), 7.76 (d, J=8.5 Hz, 1H, H-9), 7.33 (d, J=2.4 Hz, 1H, H-8), 7.22 (dd, J=9.0 and 2.4 Hz, 1H, H-14), 6.52 (t, J=5.7 Hz, 1H, NH), 5.53 (dd, J=10.4 and 7.9 Hz, 1H, H-2), 5.47 (dd, J=3.4 and 0.8 Hz, 1H, H-4), 5.19 (d, J=7.9 Hz, 1H, H-1), 5.13 (dd, J=10.4 and 3.4 Hz, 1H, H-3), 4.24 (dd, J=11.2 and 7.1 Hz, 1H, H-6), 4.16 (dd, J=11.2 and 6.0 Hz, 1H, H-6), 4.14 (dd, J=6.0 and 0.8 Hz, 1H, H-5), 3.59 (quad, J=6.1 Hz, 2H, H-19), 3.46 (t, J=6.1 Hz, 2H, H-21), 2.17 (s, 3H, COCH3), 2.05 (s, 3H, COCH3), 2.05 (s, 3H, COCH3), 2.01 (s, 3H, COCH3), 1.93 (p, J=6.1 Hz, 2H, H-20). 13C NMR (151 MHz, CDCl3) δ ppm: 170.5, 170.4, 170.3, 169.5 (5 CO ester), 167.6 (C-17), 156.1 (C-7), 135.9 (C-15), 130.9 (C-13), 130.7 (C-11), 129.4 (C-16), 127.7 (C-9), 127.4 (C-12), 124.5 (C-10), 119.9 (C-14), 111.1 (C-8), 99.5 (C-1), 71.4 (C-5), 71.0 (C-3), 68.8 (C-2), 67.0 (C-4), 61.6 (C-6), 49.8 (C-21), 38.1 (C-19), 29.0 (C-20), 20.9, 20.8, 20.8, 20.7 (4 CH3CO). HRMS (ESI+): calculated for C28H33N4O11 [M+H]+ 601.2146, found 601.2150. [α]D20=−7.0° (c 1.1, MeOH).

6-(β-D-galactopyranosyloxy)-2-naphthoic acid 3-azido-propyl-amide 6

HRMS (ESI+): calculated for C20H25N4O7 [M+H]+ 433.1723, found 433.1722.

O-2-Cyanoethyl-O'-(3,6,9-trioxadodecan-11-ynyl)-N,N-diisopropyl-phosphoramidite 33

To a solution of 3,6,9-trioxadodecan-11-yn-1-ol 31 (376 mg, 2 mmol) in dry dichloromethane (20 mL) in presence of 4 Å molecular sieve and under argon, diisopropylethylamine (520 μl, 3 mmol) was added and then O-(2-cyanoethyl)-N,N-diisopropyl-chlorophosphoramidite (480 μl, 2 mmol) was added dropwise. After 2 h stirring at room temperature, 1 mL of water was added. After 10 min, the solution was diluted with dichloromethane (40 mL) and then washed with a saturated aqueous NaHCO3 (75 mL). The organic layer was extracted with dichloromethane (2×100 mL), dried over Na2SO4 and evaporated to dryness under reduced pressure. The crude was chromatographied on silica gel, 0 to 50% of ethyl acetate in cyclohexane containing 4% Et3N, affording 33 as colorless syrup 563 mg, 73%. TLC: Rf=0.55 Cyclo/AcOEt/Et3N 5:4:1, v/v/v. 1H-NMR (CDCl3, 300 MHz): δ 1.14 (dd, 12H, J=6.8 Hz, Isopropyl), 2.36 (t, 1H, J=2.4 Hz, —CCH), 2.59 (t, 2H, J=6.5 Hz, —CH2-CN), 3.5-3.81 (m, 16H, —CH—, —O—CH2-CH2-O—, —O—CH2-P), 4.14 (d, 2H, J=2.5 Hz, HCC—CH2). 13C-NMR (CDCl3, 100 MHz): δ 18.17, 18.26, 22.4, 22.4, 22.5, 22.6, 40.9, 41, 56.3, 56.5, 60.4, 60.6, 67, 68.3, 68.5, 68.6, 69, 69.2, 72.4, 77.5, 115.6. 31P-NMR (CDCl3, 121 MHz): δ 148.67 ppm. HRMS TOF-ES positive mode calculated for C18H36N2O6P [M+H2O+H]+ 407.2311 found 407.2270.

Synthesis of Mannose-Centered Aromatic Galactoside Oligonucleotide Conjugates

Immobilization on Azide Solid Support 35 of Propargyl mannoside by Cu(I)-Catalyzed Alkyne Azide 1,3-Dipolar Cycloaddition. An aqueous solution of propargyl α-mannopyranoside 347 (100 mM, 175 μL), freshly prepared aqueous solutions of CuSO4 (100 mM, 14 μL) and sodium ascorbate (500 mM, 14 μL), water (147 μL) and MeOH (350 μL) were added to 3.5 μmol of azide solid support 35.8 The resulting mixture in a sealed tube was heated at 60° C. for 45 min using a microwave synthesizer (monowave 300, Anton Paar). The temperature was monitored with an internal infrared probe. The solution was removed, and CPG beads were washed with H2O (3×2 mL), MeOH (3×2 mL) and CH3CN (3×2 mL), and dried affording the solid-supported mannoside 36.

General Procedure for Introduction of Alkynyl Phosphoramidites on Mannose Hydroxyls. Solid-supported mannoside 36 (1 μmol scale) was treated with alkynyl phosphoramidites 329 or 33, on a DNA synthesizer (ABI 394) according to by phosphoramidite chemistry. Only coupling and oxidation steps were performed. For the coupling step, benzylmercaptotetrazole (BMT) was used as activator (0.3 M in anhydrous CH3CN) and phosphoramidite x1, or x2 (0.2 M in anhydrous CH3CN), was introduced three times (3×40 μmol) with a 180 s coupling time (3×180 s). Oxidation was performed with commercial solution of iodide (0.1 M I2, THF/pyridine/water 90:5:5) for 15 s to form phophostriesters or with 3H-1,2-Benzodithiole-3-one-1,1,-dioxide with (Beaucage reagent, 0.05M in dry acetonitrile) for 60 sec to form thionophosphotriesters.

General Procedure for Elongation of DNA Sequences and Labeling with Cy3. The DNA sequences were synthesized on the solid-supported tetraalkynyl scaffolds at the 1 μmol-scale on a DNA synthesizer (ABI 394) by standard phosphoramidite chemistry. For the coupling step, BMT was used as activator (0.3 M in anhydrous CH3CN), commercially available nucleosides phosphoramidites (0.075 M in anhydrous CH3CN) were introduced with a 20 s coupling time and Cy3 amidite (0.067 M in anhydrous CH3CN) with a 180 s coupling time. The capping step was performed with acetic anhydride using commercial solution (Cap A: Ac2O/pyridine/THF, 10:10:80 and Cap B: 10% N-methylimidazole in THF) for 15 s. Oxidation was performed for 15 s using 0.1 M I2, THF/pyridine/water 90:5:5. Detritylation was performed with 2.5% DCA in CH2Cl2 for 35 s.

General Procedure for Deprotection of Solid-supported Oligonucleotides.

The CPG beads bearing modified oligonucleotides were transferred to a 4 mL screw top vial and treated with 2 mL of concentrated aqueous ammonia for 15 h at room temperature and warmed to 55° C. for 2 h. For each compound, the supernatant was withdrawn and evaporated to dryness. The residue was dissolved in water for subsequent analysis and characterization.

General Procedure for CuAAC Reaction

Procedure for introduction of azido-functionalized D-galactoside derivatives 1-6: To a solution of 5'-fluorescent-3'-alkyne oligonucleotide (100 nmol in 100 μL of H2O) were added azido-functionalized galactosides 1-6 (3 equiv. per alkyne function, 100 mM in MeOH), ~0.1 mg of Cu(0) nanopowder, triethylammonium acetate buffer 0.1 M, pH 7.7 (25 μL), water and MeOH to obtain a final volume of 250 μL (water MeOH, 1:1, v/v). The tube containing the resulting preparation was sealed and placed in a microwave synthesizer Monowave 300 from Anton Paar at 60° C. for 60 min.

Work-up of CuAAC Reactions and HPLC Purifications

EDTA (400 μL) was added to the mixtures and after centrifugation, the supernatants were withdrawn to eliminate Cu(0) and were desalted by size-exclusion chromatography on NAP10. After evaporation the 5'-fluorescent 3'-acetyl-glycomimetic oligonucleotides were dissolved in water and purified by reversed-phase preparative HPLC. Pure compounds were treated with concentrated aqueous ammonia (3 mL) for 2 h at room temperature to remove acetyl groups, and evaporated to dryness (purity >97%). Final compounds were purified again by reversed-phase preparative HPLC using a linear gradient from 8% to 32% of acetonitrile in TEAAc buffer pH 7 over 20 min. Residues were dissolved in water for subsequent analyses.

Fabrication of DDI-Microarrays

Fabrication of microstructured slides: Microstructured slides are featured with 40 square wells (3 mm width, 60±1 μm depth, with a 4.5 mm spacing between each microreactor). Microreactors were fabricated by photolithography and wet etching process onto flat glass slides. These methods are detailed elsewhere (Mazurczyk, R. et al., (2008) *Sens. Actuators, B* 128, 552-559; Vieillard, J. et al., (2007) *J. Chromatogr. B* 845, 218-225).

Silanization of the Glass Slides:

According to the protocol developed by Dugas et al. ((2003) *J. Colloid Interface Sci.* 264, 354-36; (2004) *Sens. Actuators, B* 101, 112-121; (2004) *Sens. Actuators, B* 101, 112-121), slides were functionalized as follow: after piranha treatment, the slides were heated under dry nitrogen at 150° C. for 2 h. Next, dry pentane and tert-butyl-11-(dimethylamino)silylundecanoate were added at room temperature. After 2 h of incubation, the pentane was evaporated and the slides were heated at 150° C. overnight. Functionalized slides were obtained after washing in THF and rinsing in water. The ester function was converted into the corresponding acid using formic acid for 7 h at room temperature. Acid group bearing slides were activated for amine coupling with N-hydroxysuccinimide (0.1M) and di(isopropyl)carbodiimide (0.1M) in dry THF, overnight at room temperature. Finally, the slides were rinsed in THF and dichloromethane, 10 min under ultrasound.

Immobilization of Amino-Modified Oligonucleotides:

Four amino modified oligonucleotides were purchased from Eurogentec. Spotting of 0.3 nL of the corresponding oligonucleotides at 25 μM in $PBS_{10x}$ (pH 8.5) at the bottom of each reactor (64 spots per well) with the spotting robot: Scienion sciFLEX ARRAYER s3. The substitution reaction was performed overnight at room temperature in a water saturated atmosphere, and then, water was allowed slowly to evaporate. Washing of the slides was performed with $SDS_{0.1\%}$ at 70° C. for 30 min and deionized water briefly.

TABLE 1

Main characters of DNA sequences used for DNA anchoring platform fabrication. % GC and Tm were calculated by on-line software DINAMelt Web Server (http://mfold.rna.albany.edu/?q=DINAMelt/Two-state-melting) with [Na⁺] = 137 mM in $PBS_{1x}$, [CZiP] = 1 μM et T = 37° C.

| Reference | DNA sequence 5' → 3' | % GC | Tm |
|---|---|---|---|
| Zip 1.1.1 | 5'-GTG AGC CCA GAG GCA GGG-(CH$_2$)$_7$-NH$_2$ | 72.0 | 58.3 |
| Zip 1.3.1 | 5'-GTG GAG GCA CCA AGC TTT-(CH$_2$)$_7$-NH$_2$ | 56.0 | 58.6 |
| Zip 1.4.1 | 5'-CCA AGC GAG GTG GCA TTT-(CH2)7-NH$_2$ | 56.0 | 59.6 |
| Zip 1.6.1 | 5'-GCA GAG AGC GTG CCA TTT-(CH2)7-NH$_2$ | 56.0 | 59.7 |

$$Tm = \frac{\Delta H}{\Delta H + R\ln\left(\left[\frac{[CZip]}{2}\right]\right)} \times 1000$$

Blocking Step:

To prevent non specific adsorption during the hybridization step, all slides were blocked with bovine serum albumin (BSA). Blocking was performed with BSA 4% solution in $PBS_{1x}$ (pH 7.4), at 37° C. for 2 h. The washing steps were: 3×3 min in PBS-Tween$_{0.5\%}$ followed by 3×3 min in $PBS_{1x}$ and finally the glasses were rinsed with deionized water before being dried by centrifugation.

Hybridization of Glycomimetics

Hybridization Step:

2 μL of a solution of each glycoconjugate bearing a DNA tag, at 1 μM in $PBS_{1x}$ (pH 7.4), were placed at the bottom of the corresponding well and allowed to hybridize overnight at room temperature in a water vapour saturated chamber. The samples were washed in saline-sodium citrate 2× ($SSC_{2x}$), $SDS_{0.1\%}$ at 51° C. for 1 min, followed by $SSC_{2x}$ at room temperature for an additional 5 min and finally rinsed with deionized water before being dried by centrifugation.

Blocking Step:

After hybridization, all slides were blocked again with bovine serum albumin (BSA). Blocking was performed with BSA 4% solution in $PBS_{1x}$ (pH 7.4), at 37° C. for 1 h. The washing steps: 3×3 min in PBS-Tween$_{0.5\%}$ followed by 3×3 min in $PBS_{1x}$, briefly rinsed with deionized water before dried by centrifugation.

Lectin Labeling

Alexa647 Labeling of PA-IL Lectin:

PA-IL lectin was labeled with Alexa Fluor® 647 Microscale Protein Labeling Kit (A30009) from Invitrogen. In brief, 100 μl of a 1 mg/ml solution of PA-IL (MW: 51 kDa, PA-IL was kindly provided by Dr Anne Imberty, CERMAV, Grenoble) diluted in $PBS_{1x}$ (pH 7.4) was mixed with 10 µL of 1M sodium bicarbonate (pH 8.3). The appropriate volume of reactive dye solution at 7.94 nmol/µL was transferred into the reaction tube containing the pH-adjusted protein. Reaction mixture was mixed for 15 min at room temperature before purification on a spin column (gel resin container) in order to separate the labeled protein from unreacted dye.

Lectin concentration and the dye to lectin ratio were estimated by optical density using a tray cell system combined to a Safas Monaco UV mcg spectrophotometer reading the absorbance at 281 nm and 650 nm. PA-IL concentration was estimated to be 13.53 µM with a degree of labeling of 0.20 dyes for tetrameric PA-IL.

$IC_{50}$ Determination with "on Chip" Biological Recognition

Preparation of the Solutions of Incubation:

Lectin PA-IL (0.12 µM final concentration), BSA (2% final concentration) and $CaCl_2$ (1 µg/mL final concentration) was diluted in $PBS_{1x}$ (pH=7.4). In each micro tube was added the inhibitor lactose at the desired final concentration (0; $1.10^{-5}$; $1.10^{-4}$; $5.10^{-4}$; $1.10^{-3}$; $5.10^{-3}$; $1.10^{-2}$; $5.10^{-2}$; 0.1; 1; 5; 10; 50; $10^2$; $5.10^2$; $10^3$; $5.10^3$; $10^4$; $10^5$; $3.10^5$).

Incubation of the Complex Glycoconjugate-Lectin on the Microreactors:

2 µL of each solution were deposited in the corresponding microwells and the slide was incubated at 37° C. in a water vapor saturated chamber for 3 h. The washing steps are: $PBS-Tween_{0.2\%}$ 5 min at 4° C., then briefly in deionized water and dried by centrifugation.

Fluorescence Scanning:

Slide was scanned at 532 nm then at 635 nm with the Microarray scanner, GenePix 4100A software package (Axon Instruments; $\lambda_{ex}$ 532/635 nm and $\lambda_{em}$ 575/670 nm). The fluorescence signal of each conjugate was determined as the average of the mean fluorescence signal of sixty-four spots.

$IC_{50}$ values were determined using "BioDataFit 1.02 program". The model chosen was "Sigmoidal":

$$Y=a+(b-a)/[1+10^{\wedge}(x-c)]$$

with $a=FI_{min}$, $b=FI_{max}$, x=log [PA-IL] and $c=\log(IC_{50})$. $FI_{min/max}$ is the minimum/maximum Alexa-647 fluorescence signal observed for a galactomimetic.

II—Synthesis of Glycoclusters 17a-e and 18 and Determination of their Binding Efficiency to PA-IL:

II-A Synthesis:

We synthesized mannose-centered glycoclusters 17 a-e and 18 and studied the influence of six different linkers in glycomimetic on their recognition to the PA-IL. The linkers were chosen to spam different lengths (from 9 to 14 atoms) and solvation capacities (alkyl, aromatic or ethylene glycol) (FIG. 1).

Figure 2:
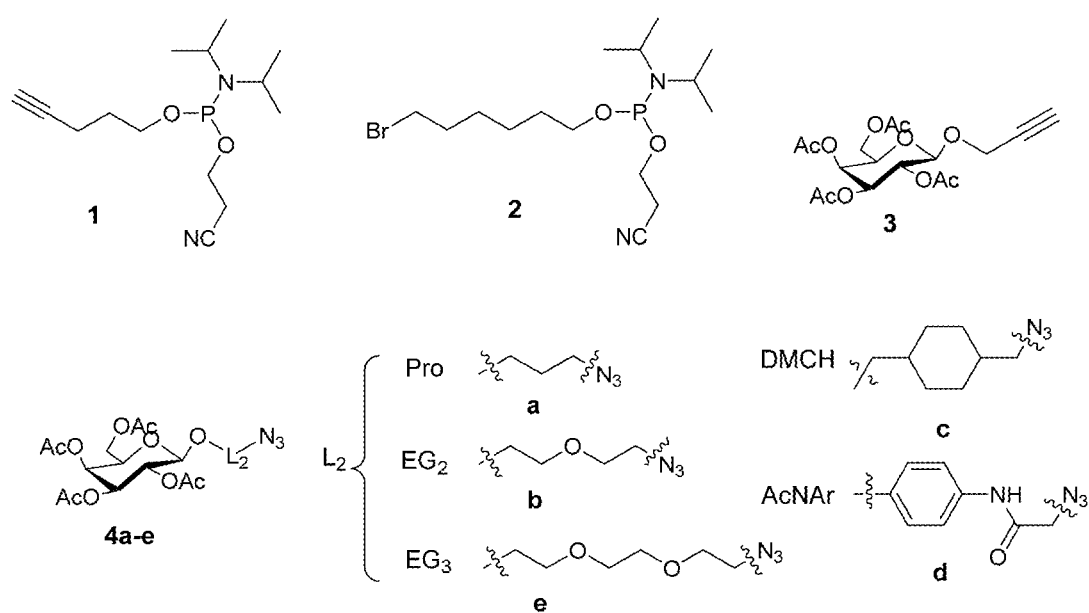
FIG. 2 shows the structure of building blocks for the synthesis of the galactoclusters

To this end, we used two phosphoramidites (i.e. pent-4-ynyl 1 and 6-bromohexyl 2) in combination with propagyl galactose 3 and different galacto azide derivatives 4a-e allowing the construction of the glycoclusters by phosphoramidite chemistry (Beaucage, S. L., and Caruthers, M. H. (1981) *Tetrahedron Lett*. 22, 1859-1862) and copper catalyzed azide alkyne cycloaddition (CuAAC) "click" chemistry (Rostovtsev, V. V. et al., (2002) *Angew. Chem. Int. Ed*. 41, 2596-2599; Tornoe, C. W., Christensen, C., and Meldal, M. (2002) *J. Org. Chem*. 67, 3057-3064) (FIG. 2).

Propargyl galactose 3 and galactose azide derivatives 4a-e and were prepared according to literature protocols. Hasegawa, T. et al., (2007) *Org. Biomol. Chem*. 5 (15), 2404-2412; Joosten, J. A. F. et al., (2004) *J. Med. Chem*. 47, 6499-6508; Szurmai, Z. et al., (1989) *Acta Chimica Hungarica-Models in Chemistry* 126, 259-269; Pourceau, G. et al., (2009) *J. Org. Chem*. 74, 1218-1222; Mereyala, H. B., and Gurrala, S. R. (1998) *Carbohydr. Res*. 307, 351-354).

Figure 3A:
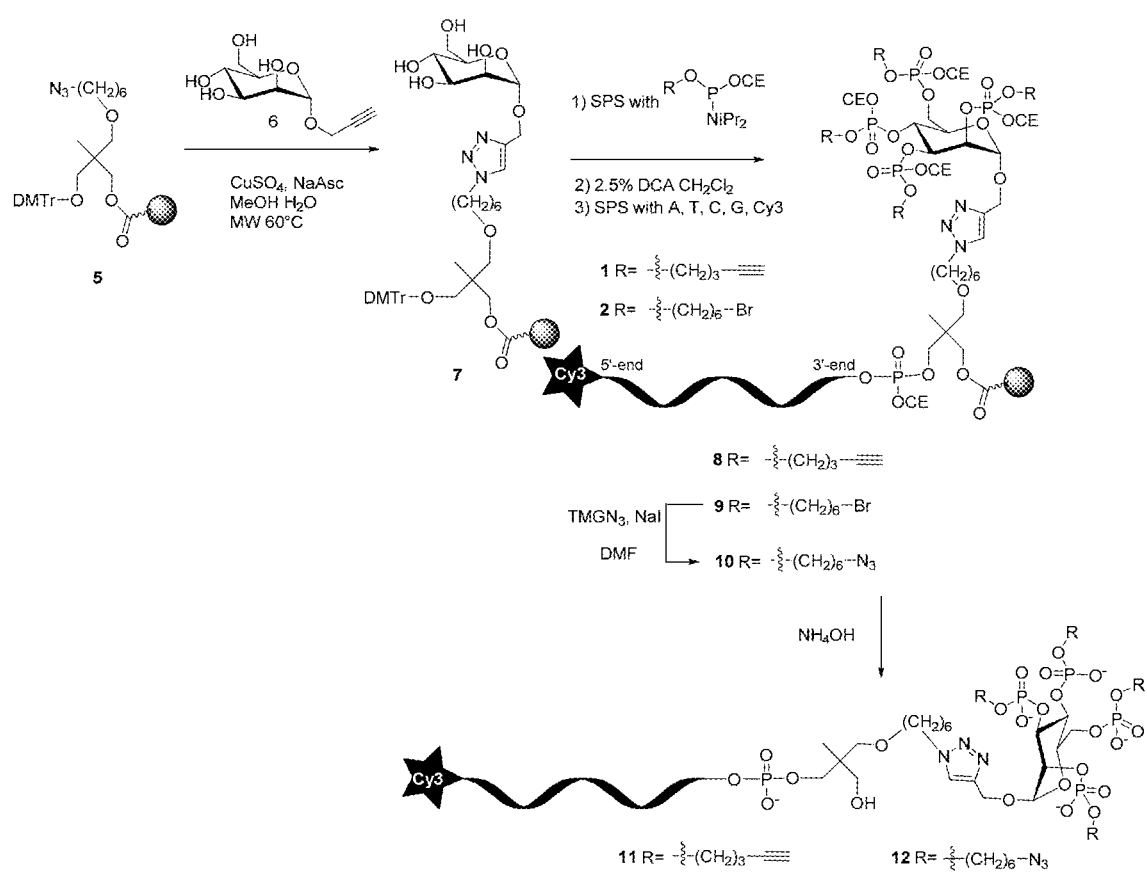
FIGS. 3a and 3b is a scheme showing the synthesis of glycoclusters 17a-e and 18. L2 are explained in caption of FIG. 2
Figure 3B:
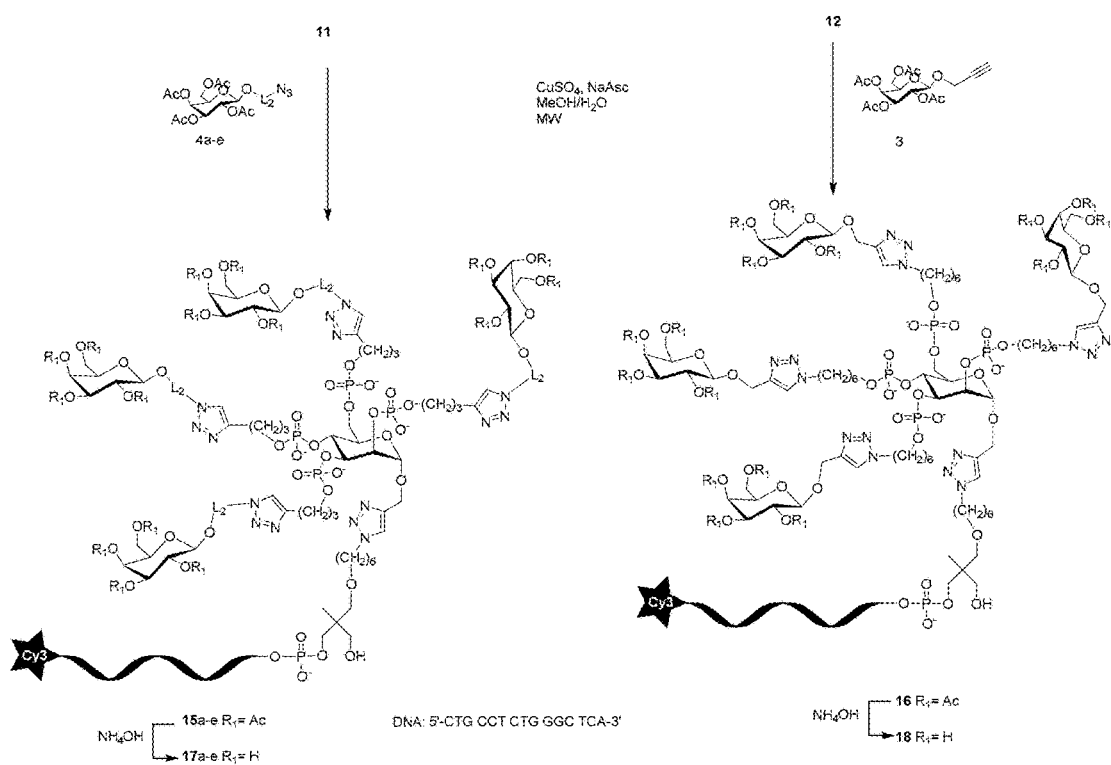

The mannose-centered glycoclusters 17a-e and 18 were prepared according to a recently reported strategy (Pourceau, G. et al., (2010) *Bioconjugate Chem*. 21, 1520-1529). Basically, a mannose propargyl 6 was immobilized on an azide solid support 5 by CuAAC and then pent-4-ynyl 1 or bromohexyl 2 phosphoramidites were introduced on the four hydroxyls by phosphorylation affording the mannose core bearing four pentynylphosphate or four bromohexylphosphate groups (FIG. 3). The oligonucleotide was elongated and labeled with a fluorescent dye (Cy3) affording 8 and 9. For 9, the four bromine atoms were substituted with tetramethylguanidine azide ($TMG N_3$) to give the tetra azide oligonucleotide 10. After an ammonia treatment, the compounds 11 and 12 were conjugated with galactose derivatives 4a-e and 3 respectively by CuAAC in solution, using Cu(0), affording the mannose-centered tetra-galactose oligonucleotide conjugates 15a-e and 16. Pure conjugates were isolated by reverse phase HPLC and a last treatment with ammonia hydrolyzed the acetyl groups of the galactose moieties affording the six expected galactoclusters 17a-e and 18 exhibiting different linkers.

Figure 4:
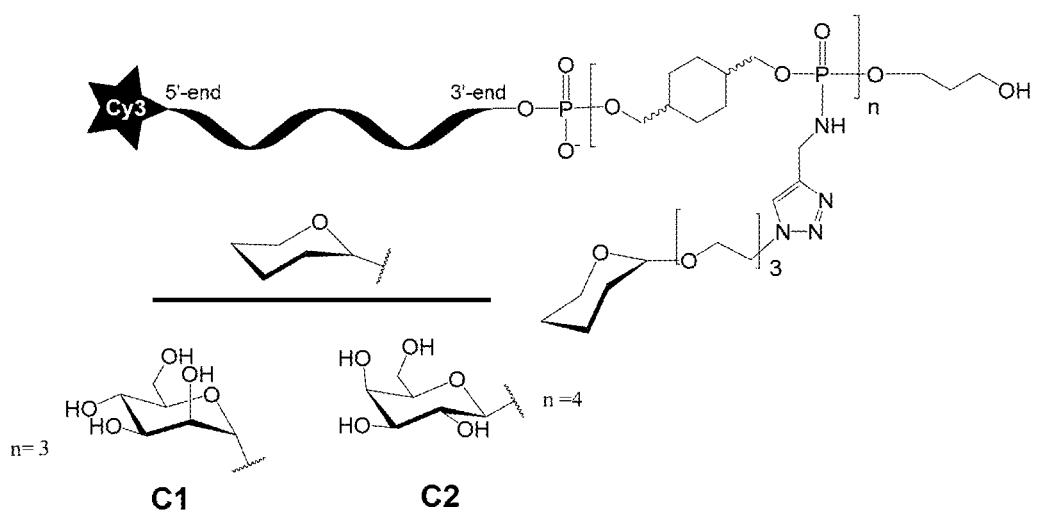
FIG. 4 shows the structure of negative (DMCH-PN-MTzEG$_3$-O-Man)$_3$ C1 and positive (DMCH-PNMTzEG$_3$-O-Gal)$_4$ C2 glycocluster controls
Figure 5:
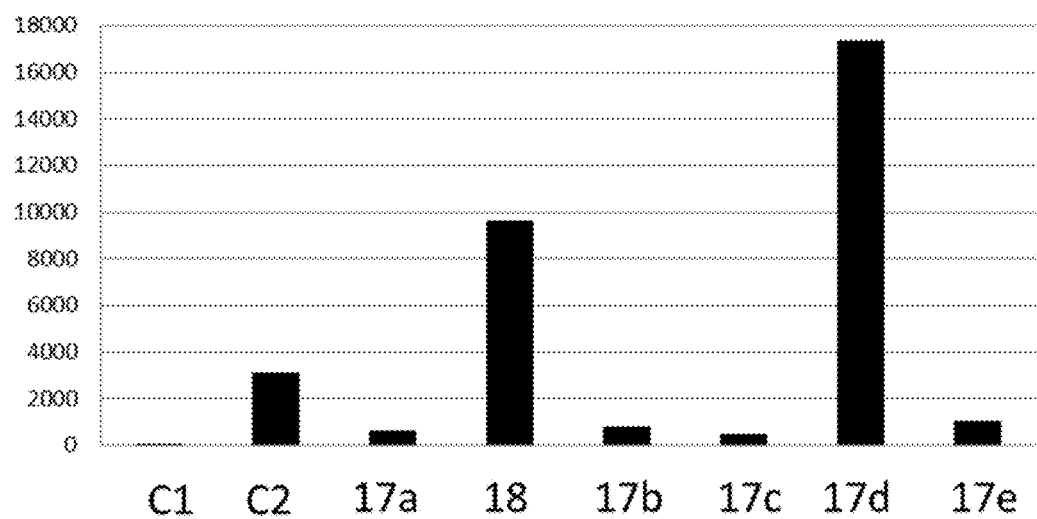
FIG. 5 is a graph showing the fluorescence intensity (arbitrary units u. a.) of glycoclusters C1, C2, 17a-e and 18 bound with Alexa 647-PA-IL on microarray.

II-B Biological Test Protocols:

The binding efficiency of the galactomimetics 17a-e and 18 to PA-IL was determined/measured using a DNA-based glycoarray by direct fluorescence scanning (Chevolot, Y. et al., (2007) *Angew. Chem. Int. Ed*. 46, 2398-2402). A linear trimannosylcluster $(DMCH-PNMTzEG_3-O-Man)_3$ (C1, disclosed in Chevolot et al., 2007) was used as negative control showing the specific binding of PA-IL to galactoclusters and a linear tetragalactosylcluster $(DMCH-PNMTzEG-O-Gal)_4$ (C2, Chevolot, Y. et al., (2011) *Chem. Comm*. 47, 8826-8828) was used for positive control and comparison (FIG. 4). To this purpose, all the glycoclusters were immobilized on a DNA-array by DNA directed Immobilisation (DDI) thanks to their DNA tag. Then, alexa647-PA-IL was added and incubated for 3 hours, after washing the fluorescence intensity was read at 635 nm giving relative information of the binding strength (FIG. 5).

II-C Test Results:

Linear trimannose $(DMCH-PNMTzEG_3-O-Man)_3$ C1 cluster did not bind to PA-IL, showing the selective recognition and the absence of unspecific binding on the microarray. The linear tetragalactose cluster $(DMCH-PNMTzEG-O-Gal)_4$ C2 exhibited fluorescence around 3100 arbitrary unit (a. u.).

The data showed that there is no obvious correlation between the length of the linker between the galactose moiety and the mannose-core on the binding efficiency.

In contrast, it appeared that galactomimetics with aromatic group near the galactose moiety (17d and 18) showed a high binding with a preference for the phenyl (AcNPhe) one (17d) compared to the triazole methylene (TzM) motif (18). The differences of binding between 17a, 17b, 17e and 17c were not significant suggesting that ethylene glycol ($EG_2$ or $EG_3$) or aliphatic (Pro or DMCH) linkers did not further interact with amino acid residues of PA-IL.

III— Synthesis of Glycoclusters 22-31 and Determination of their Binding Efficiency to PA-IL:

We looked at the effect of the AcNPhe-O-Galactose moiety on different scaffold with on the one hand its introduction into linear scaffolds like DMCH scaffold exhibiting two to five residues $(DMCH-PNMTzAcNPhe-O-Gal)_{2-5}$ (compounds 22-25) or desoxythymidine scaffold exhibiting four galactose residues (dT-PNMTzAcNPhe-O-

Figure 8:
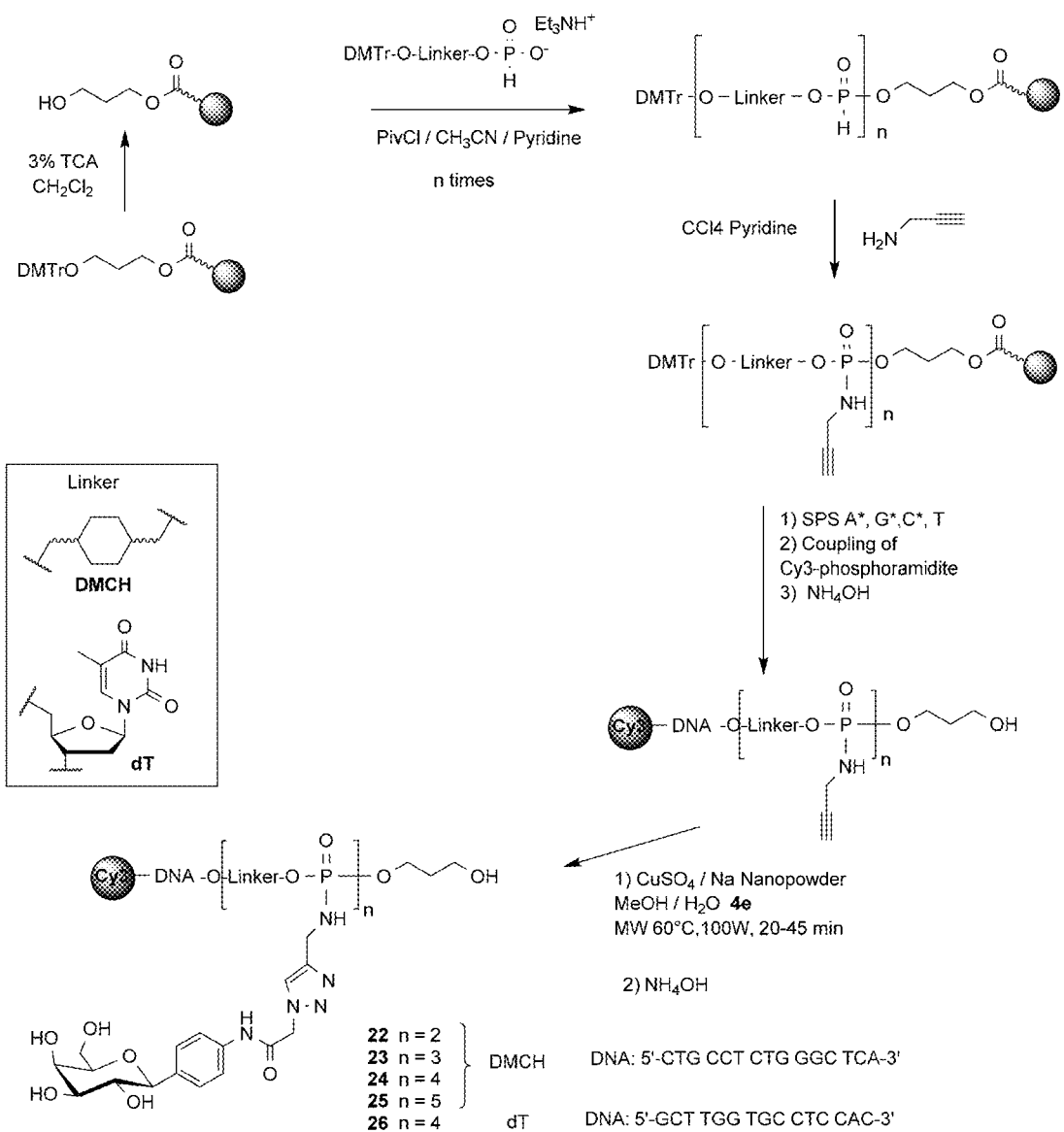
FIG. 8 is a scheme illustrating the synthesis of linear (DMCH-PNMTzAcNPhe-O-Gal)$_{2-5}$ (22-25) and (dT-PN-MTzAcNPhe-O-Gal)$_4$ (26) clusters
Figure 9:
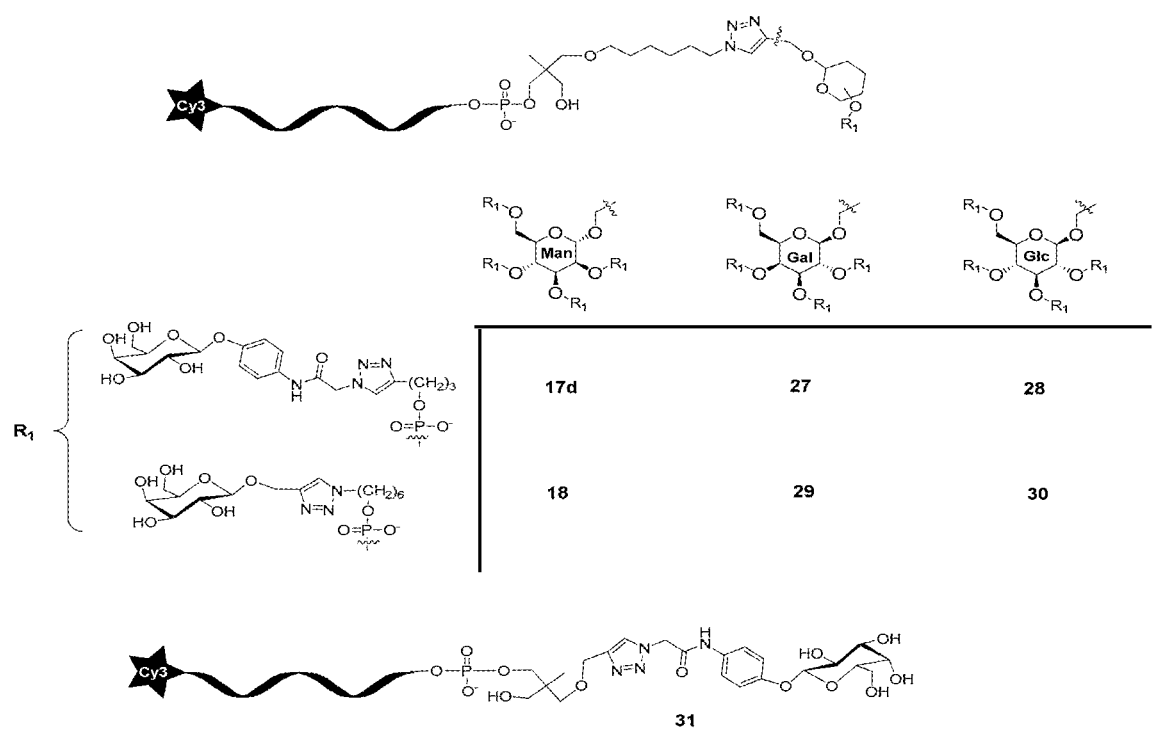
FIG. 9 represents the structure of the six hexose-centered tetragalactoclusters synthesized from a mannose- (17d, 18), galactose-core (27, 29) and glucose-core (28, 30) and a mono-TzAcNPhe-O-Galactose (31) conjugate.

Gal)₄ (26) (FIG. 8) and on the other hand the AcNPhe-O-Galactose moiety was introduced into galactose- (27) and glucose-centered scaffolds (28) (FIG. 9). For comparison, the effect of HexTzM-galactose moiety was also studied with galactoclusters built on galactose- (29) and glucose-centered scaffolds (30) (FIG. 9).

III-A Synthesis:

The linear DMCH galactoclusters were synthesized starting from propanediol solid support on which DMCH H-phosphonate monoester (Chevolot, Y. et al., (2007) *Angew. Chem. Int. Ed.* 46, 2398-2402; Bouillon, C. et al, (2006) *J. Org. Chem.* 71, 4700-4702) were coupled two to five time by H-phosphonate chemistry using pivaloyl chloride as activator (FIG. 8). The resulting H-phosphonate diester linkages were oxidized by carbon tetrachloride in presence of propargyl amine allowing the introduction of alkyne functions. Then, the oligonucleotide was assembled and Cy3 labeled by phosphoramidite chemistry. After deprotection and release from the solid support, by ammonia treatment, the resulting modified oligonucleotides exhibiting two to five alkynes were conjugated with 4d by CuAAC. After HPLC purification the acetyl groups were hydrolyzed by ammonia leading to the oligonucleotides conjugated to linear DMCH galactoclusters (DMCH-PNMTzAcNPhe-O-Gal)$_{2-5}$ (22-25). The linear tetra-galactose on deoxythymidine scaffold (dT-PNMTzAcNPhe-O-Gal)₄ (26) was synthesized similarly using commercially available DMTr-thymidine H-phosphonate introduced four times on the solid support.

The synthesis of galactose-centered (POProTzAcNPhe-O-Gal)₄ (27) and glucose-centered (POProTzAcNPhe-O-Gal)₄ (28), galactose-centered (HexTzM-Gal)₄ (29), and glucose-centered (HexTzM-Gal)₄ (30) proceeded with the same protocol as described above on mannose-scaffold but using propargyl-galactose or propargyl-glucose. Those were first immobilized on azide solid support 5. For comparison purpose, an oligonucleotide conjugate (31) exhibiting only one TzAcNPhe-O-Gal motif was synthesized (FIG. 9). To this end, a Cy3-oligonucleotide was synthesized from a mono-alkyne solid support which was conjugated with 4d by CuAAC (see SI).

Figure 10:
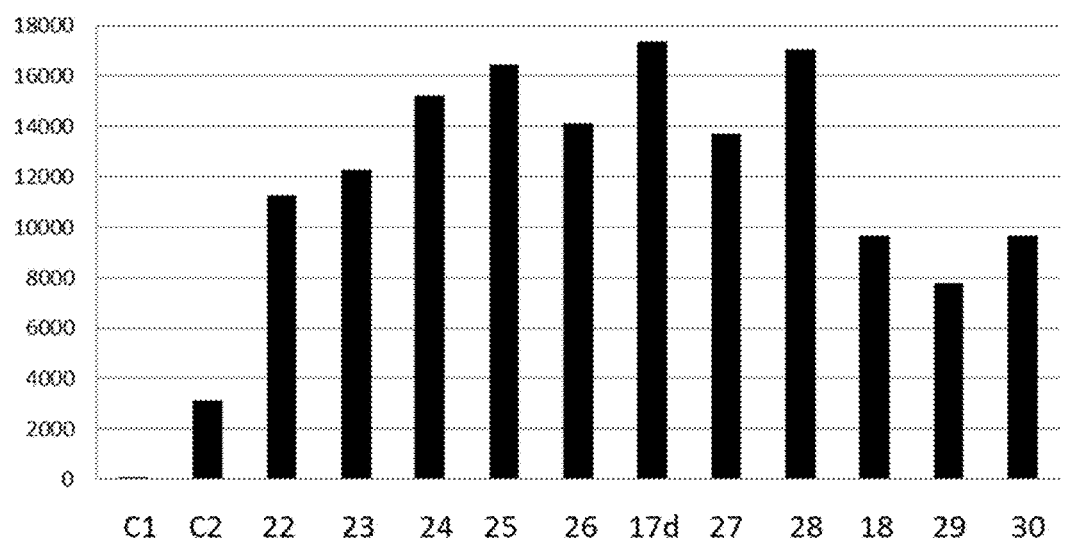
FIG. 10: Fluorescence Arbitrary Unit (a. u.) of linear and hexose-centered glycoclusters (DMCH-PNMTzEG$_3$-O-Man)$_3$ C1, (DMCH-PNMTzEG$_3$O-Gal)$_4$ C2 (DMCH-PN-MTzAcNPhe-O-Gal)$_{2-5}$ (22-25), (dT-PNMTzAcNPhe-O-Gal)$_4$ (26), Man-(POProTzAcNPhe-O-Gal)$_4$ (17d), Gal-(POProTzAcNPhe-O-Gal)$_4$ (27), Glc-(POProTzAcNPhe-O-Gal)$_4$ (28), Man-(HexTzM-O-Gal)$_4$ (18), Gal-(HexTzM-O-Gal)$_4$ (29) and Glc-(HexTzM-O-Gal)$_4$, (30) bonded with alexa647-PA-IL.

III-B Biological Test Protocols:

Test 1:

The binding properties of these galactoclusters to PA-IL were studied using a DDI affording a glycoarray. After their immobilization on the chip, alexa 647-PA-IL was added and after washing the fluorescence intensity of each glycocluster was read (FIG. 10). Alexa 647 fluorescent signal (excitation 635 nm, emission 675 nm) is correlated to PA-IL binding.

Test 2:

Since the dynamic range of fluorescent intensity is rather limited, as already reported, (Moni, L. et al., (2009) *ChemBioChem* 10, 1369-1378; Zhang, J. et al., (2009) *Biosens. Bioelectron.* 24, 2515-2521.) we then determined the IC$_{50}$ value of the glycoclusters using lactose as inhibitor (Table 1) and potency was calculated. In our case the IC$_{50}$ value corresponds to the lactose concentration requires to displace 50% of PA-IL from the glycocluster. Hence, the highest the IC$_{50}$ value the highest the affinity of the glycocluster for PA-IL. So the IC$_{50}$ value was called IC$_{50Lac}$.

III-C Test Results:

Test 1:

The fluorescent signal of the linear DMCH glycoclusters rose with the number of galactose residues showing the benefit of the increase of saccharide motifs on the binding efficiency. The tetracluster with MTzEG₃-O-Gal motifs displayed a fluorescent signal about 5-fold lower than its analog bearing TzAcNPhe-O-Gal motifs confirming the better binding of aromatic-galactose. Both tetrameric linear glycoclusters with DMCH or thymidine scaffold exhibited a higher binding than the DMCH trimeric cluster but with a preference for the DMCH one. Concerning the hexose-centered tetra-galactoclusters, the data confirmed the better binding of galactoclusters exhibiting ProTzAcNPhe-O-Gal motifs versus HexTzM-Gal ones whatever the hexose-core. For both families, glycoclusters built from a mannose- and glucose-core displayed similar fluorescent signal and those built from a galactose-core displayed a lower signal (FIG. 10).

The comparison between linear and hexose-centered glycoclusters bearing four ProTzAcNPhe-O-Gal motifs gives the following increase of fluorescent signal: Gal(POProTzAcNPhe-O-Gal)₄≤(dT-PNMTzAcNPhe-O-Gal)₄< (DMCH-PNMTzAcNPhe-O-Gal)₄<Glc(POProTzAcNPhe-O-Gal)₄≤Man(POProTzAcNPhe-O-Gal)₄. This data showed the better binding of mannose- and glucose-centered glycoclusters among all of the glycoclusters even better than the linear DMCH penta-galactose.

Test 2:

The comparison of the monogalactoses DMCH-PNMTzEG₃-O-Gal (Chevolot, Y. et al., (2007) *Angew. Chem. Int. Ed.* 46, 2398-2402) and DMCH-PNMTzAcNPhe-O-Gal with IC$_{50Lac}$ value of 5 and 16 mM respectively showed a 3.2-fold increase of binding for the aromatic galactose (Entries 1 and 2) which is similar to the observation made by Ceccioni et at by Enzyme Linked Lectin Assay (Cecioni, S. et al., (2012) *Chem. Eur. J.* 18, 6250-6263). For the linear galactoclusters, we observed an increase of IC$_{50Lac}$ value corresponding to a better binding to PA-IL with the increase of number of residues with a threshold effect between 2 and 3 residues (Table 1, entries 4 and 5). The benefit of the PNMTzAcNAr linker versus MTzEG₃ linker was confirmed (DMCH-PNMTzAcNPhe-O-Gal)₄ 24 entry 6: IC$_{50Lac}$=1056 µM vs (DMCH-PNMTzEG₃-O-Gal)₄ C2, entry 3: IC$_{50Lac}$=773 µM). This trend was stressed for the mannose-centered glycoclusters (entry 8: IC$_{50Lac}$=29 µM for G3 Man(POProTzEG₃-O-Gal)₄ versus entry 9: IC$_{50Lac}$=2826 µM for 17d Man(POProTzAcNPhe-O-Gal)₄. The results indicated the superiority of a TzAcNPhe-O-Gal motif with a mannose-centered topology to gain a higher binding to PA-IL with an increase of potency of 177-fold compared with the monoaromatic-galactose and 565-fold compared with the EG₃-O-galactose (Entry 9). These results illustrate that the combination of the nature of the linker and of the spatial arrangement has a strong influence on the affinity.

The data showed that the influence of hexose-core on the binding to PA-IL is different according the nature of the galactose-linkers (Table 2). Concerning the tetragalactoclusters, with a POProTzAcNAr linker, the best binding was observed for the mannose-core 17d following by the glucose- and the galactose-core (Entries 9-11). In contrast, with a HexTzM linker, the best binding was observed for the cluster with a glucose-core followed by the galactose- and mannose-core (Entries 12-14).

TABLE 2

IC$_{50Lac}$ values of the glycoclusters determined by competition with lactose.

| Entry | Glycocluster | IC$_{50Lac}$ μM | Potency vs EG$_3$-O-Gal | Potency vs AcNPhe-O-Gal |
|---|---|---|---|---|
| 1 | DMCH-PNMTz EG$_3$-O-Gal | 5 | 1.0 | 0.3 |
| 2 | MTzAcNPhe-O-Gal 31 | 16 | 3.2 | 1.0 |
| 3 | (DMCH-PNMTzEG$_3$-O-Gal)$_4$ C2 | 773 | 155 | 48 |
| 4 | (DMCH-PNMTzAcNPhe-O-Gal)$_2$ 22 | 185 | 37 | 12 |
| 5 | (DMCH-PNMTzAcNPhe-O-Gal)$_3$ 23 | 866 | 173 | 54 |
| 6 | (DMCH-PNMTzAcNPhe-O-Gal)$_4$ 24 | 1056 | 211 | 66 |
| 7 | (DMCH-PNMTzAcNPhe-O-Gal)$_5$ 25 | 1550 | 310 | 97 |
| 8 | Man(POProTzEG$_3$-O-Gal)$_4$ C3 | 29 | 5.8 | 1.8 |
| 9 | Man(POProTzAcNPhe-O-Gal)$_4$ 17d | 2826 | 565 | 177 |
| 10 | Gal(POProTzAcNPhe-O-Gal)$_4$ 27 | 662 | 132 | 41 |
| 11 | Glc(POProTzAcNPhe-O-Gal)$_4$ 28 | 805 | 161 | 50 |
| 12 | Man(HexTzM-Gal)$_4$ 18 | 107 | 21 | 6.7 |
| 13 | Gal(HexTzM-Gal)$_4$ 29 | 532 | 106 | 33 |
| 14 | Glc(HexTzM-Gal)$_4$ 30 | 775 | 155 | 48 |
| 15 | Man(POEG$_2$MTzEG$_3$-Gal)$_4$ 36 | 24 | 4.8 | 1.5 |
| 16 | Man(POEG$_2$MTzAcNPhe-O-Gal)$_4$ 32 | 4218 | 844 | 264 |
| 17 | Man(POProTzAcNPhe-O-Gal)$_8$ 34 | 6803 | 1361 | 425 |
| 18 | Man[POTHME(MTzAcNPhe-O-Gal)$_2$]$_4$ 35 | 1807 | 361 | 113 |

| cluster | DNA-tag | Galactoclusters | IC$_{50}$ (mM) | K$_d$ (nM) |
|---|---|---|---|---|
| G6 | cZip 1.4 | Man(PSEG$_2$MTzAcNPhe-CH$_2$-Gal)$_4$ | 5.7 | 170 |
| G8 | cZip 1.6 | Man(PSEG$_3$MTzAcNPhe-CH$_2$-Gal)$_4$ | 8.4 | 125 |
| G5 | cZip 1.3 | Man(EG$_2$MTzAcNPhe-CH$_2$-Gal)$_4$ | 8.1 | 99 |
| G7 | cZip 1.2 | Man(EG$_3$MTzAcNPhe-CH$_2$-Gal)$_4$ | 9.1 | 85 |
| G13 | cZip 1.5 | Man(EG$_2$MTzAcNPhe-CH$_2$-SGal)$_4$ | 12.0 | 85 |
| G15 | cZip 1.2 | Man(EG$_3$MTzAcNPhe-CH$_2$-SGal)$_4$ | 13.3 | 76 |
| G4 | cZip 1.1 | Man(PSEG$_3$MTzAcNPh-Gal)$_4$ | 17.7 | 76 |
| G16 | cZip 1.6 | Man(PSEG$_3$MTzAcNPhe-CH$_2$-SGal)$_4$ | 18.1 | 75 |
| G14 | cZip 1.5 | Man(PSEG$_2$MTzAcNPhe-CH$_2$-SGal)$_4$ | 18.5 | 71 |
| G12 | cZip 1.1 | Man(PSEG$_3$MTzAcNPh-SGal)$_4$ | 19.7 | 70 |
| G2 | cZip 1.4 | Man(PSEG$_2$MTzAcNPh-Gal)$_4$ | 36.2 | 63 |
| G10 | cZip 1.5 | Man(PSEG$_2$MTzAcNPh-SGal)$_4$ | 38.2 | 55 |
| G9 | cZip 1.2 | Man(EG$_2$MTzAcNPh-SGal)$_4$ | 45.1 | 51 |
| G11 | cZip 1.6 | Man(EG$_3$MTzAcNPh-SGal)$_4$ | 63.9 | 49 |
| G23 | cZip 1.10 | Man(EG$_3$MTzproNCONapht-OGal)$_4$ | 68.0 | 48 |
| G19 | cZip 1.10 | Man(EG$_3$MTzproNCOBisphe-OGal)$_4$ | 68.9 | 46 |
| G20 | cZip 1.4 | Man(PSEG$_3$MTzproNCOBisphe-OGal)$_4$ | 81.6 | 43 |
| G1 | cZip 1.6 | Man(PSEG$_2$MTzproNCOBisphe-OGal)$_4$ | 103.1 | 39 |
| G18 | cZip 1.1 | Man(EG$_2$MTzAcNPh-Gal)$_4$ | 91.6 | 36 |
| G24 | cZip 1.4 | Man(PSEG$_3$MTzproNCONapht-OGal)$_4$ | 129.4 | 31 |
| G3 | cZip 1.4 | Man(EG$_3$MTzAcNPh-Gal)$_4$ | 122.7 | 28 |
| G22 | cZip 1.6 | Man(PSEG$_2$MTzproNCONapht-OGal)$_4$ | 160.2 | 20 |
| G17 | cZip 1.3 | Man(EG$_2$MTzproNCOBisphe-OGal)$_4$ | 160.3 | 20 |
| G21 | cZip 1.3 | Man(EG$_2$MTzproNCONapht-OGal)$_4$ | 178.3 | 14 |

Figure 11:
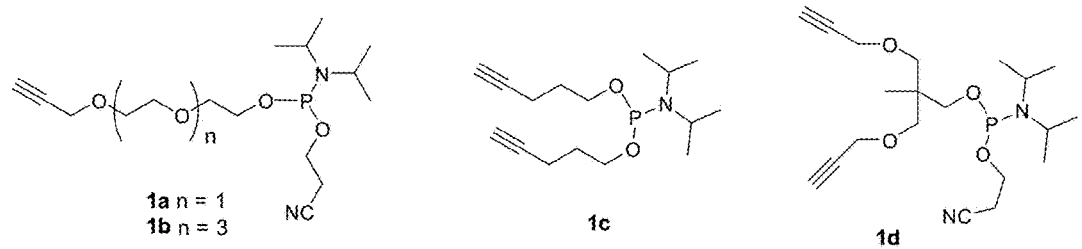
FIG. 11: Structure of propargyl di- or tetra-ethylene glycol 1a, 1b, bis-pent-4-ynyl 1c and 2,2-(bis-propargyloxymethyl) propyl 1d phosphoramidites.
Figure 12A:
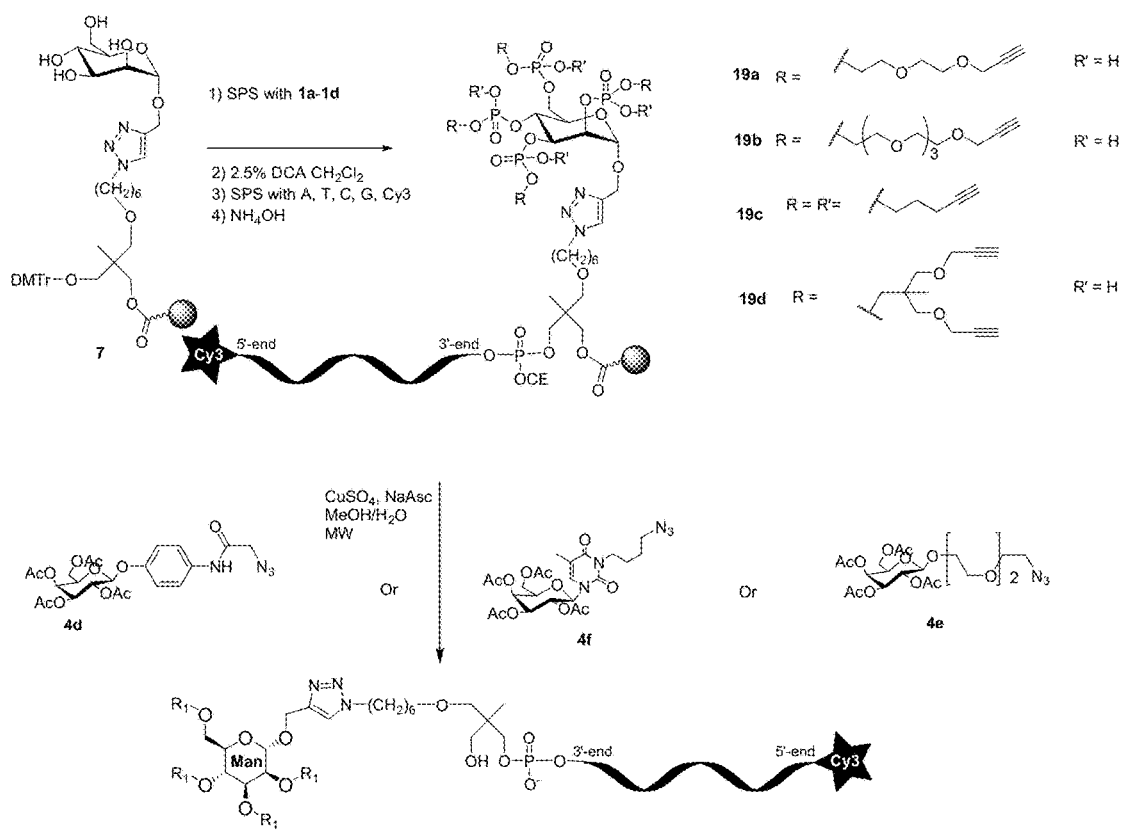
FIG. 12a and FIG. 12b: Synthesis scheme and structures of Man(POEG$_2$MTzEG$_3$-O-Gal)$_4$ (36), Man (POEG$_2$MTzAcNPhe-O-Gal)$_4$ (32), Man (POEG$_4$MTzAcNPhe-O-Gal)$_4$ (33), Man(POProTzAcN-Phe-O-Gal)$_8$ (34), Man[POTHME(MTzAcNPhe-O-Gal)$_2$]$_4$ (35), Man(POProTzBuT-Gal)$_4$ (37), Man(POEG$_2$MTzBuT-Gal)$_4$ (38) and Man[POTHME(MTzBuT-Gal)$_2$]$_4$ (39).
Figure 12B:
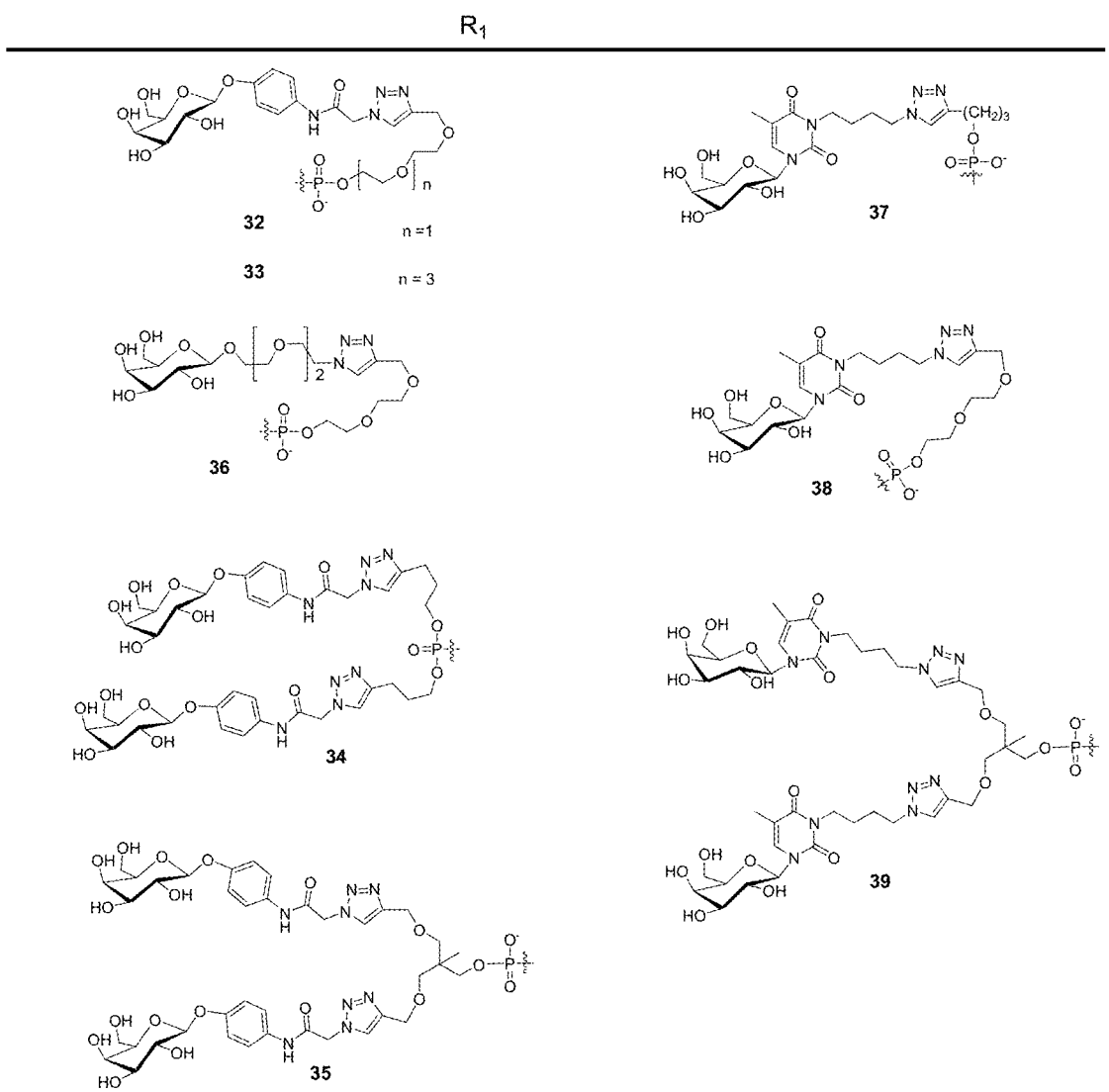

IV—Synthesis of Glycoclusters 32-39 and Determination of their Binding Efficiency to PA-IL:

We prepared compounds comprising a mannose core and the TzAcNPhe-O-Gal motifs with some variations. On the one hand, we increased the length/flexibility between the mannose-core and the triazole using a di- or tetra-ethylene glycol propargyl phosphoramidite 1a-b instead of the pentynyl one and on the other hand, we introduced eight alkynyl groups using either a bis-pentynyl phosphoramidite 1c or a 2,2-(bis-propargyloxymethyl)propyl phosphoramidite 1d (FIG. 11). Thus the new mannose-centered tetragalactoclusters Man(POEG$_2$MTzAcNPhe-O-Gal)$_4$ (32), and Man (POEG$_4$MTzAcNPhe-O-Gal)$_4$ (33) exhibit a 17-atom, and 23-atom linker length respectively instead of 13-atom linker length for Man(POProTzAcNPhe-O-Gal)$_4$ 17d. The mannose-centered octagalactoclusters Man(POProTzAcNPhe-O-Gal)$_8$ (34) and Man[POTHME(MTzAcNPhe-O-Gal)$_2$]$_4$ (35) exhibits two residues on each hydroxyl of the mannose-core (FIG. 12). So we could evaluate the influence of the linker length and the influence of the number of residues on the binding property. For comparison purpose, we also synthesized the analogue Man(POEG$_2$MTzEG$_3$-O-Gal)$_4$ (36) where the AcNPhe-O-Gal motifs were replaced by the EG$_3$-Gal motifs (FIG. 12).

Finally, to gain more insight of an "aromatic effect", we synthesized new glycoclusters exhibiting galactose motifs where the O-phenyl was replaced by thymine (T-Gal) (37, 38, 39). These analogs were designed as they may form hydrogen bounds between the heteroatoms of the thymine and the amino acid of the lectin leading to a possible better affinity.

IV-A Synthesis:

For the synthesis of the new glycoclusters exhibiting AcNPhe-O-Gal motifs, the solid-supported mannose 7 was phosphorylated with either a propargyl di- (1a) or tetra-ethyleneglycol (1b) phosphoramidite, bis-pent-4-ynyl phosphoramidite (1c) or 2,2-(bis-propargyloxymethyl)propyl phosphoramidite (1d). Then after oligonucleotide elongation and labeling, the tetra/octa alkyne constructions (19a-d) were conjugated to 4d affording the expected mannose-centered tetra/octagalactocluster oligonucleotide conjugates Man(POEG$_2$MTzAcNPhe-O-Gal)$_4$ (32), Man (POEG$_4$MTzAcNPhe-O-Gal)$_4$ (33), Man(POProTzAcN- Phe-O-Gal)₈ (34) and Man[POTHME(MTzAcNPhe-O-Gal)₂]₄ (35) respectively (FIG. 12). Likewise the tetraalkyne 19a with propargyldiethylene glycol linkers was also conjugated with 4e affording the Man(POEG₂MTzEG₃-O-Gal)₄ (36).

Figure 13:
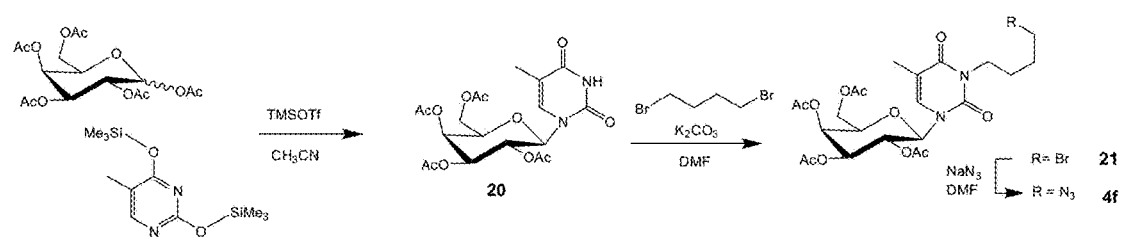
FIG. 13: Synthesis scheme of N$^3$-(4-azido-butyl)-N$^1$-(2', 3',4',6'-tetra-O-acetyl-galactose)-thymine 4f.

Concerning the synthesis of the glycoclusters exhibiting T-Gal motifs, the azide derivative 4f was prepared according to a protocol described in literature for the synthesis of glucose-thymidine (Gillaizeau, I. et al., (2003) *Eur. J. Org. Chem.*, 666-671. To this end 1,2,3,4,6-penta-O-acetyl-galactose was glycosylated with 2,4-bis-O-trimethylsilyl-thymine affording the 2',3',4',6'-tetra-O-acetyl-galactopyranose-$N^1$-thymine 20 (T-Gal) (or 2,3,4,6-tetra-O-acetyl-$N^1$-thymine-β-D-galactopyranoside) (FIG. 13). It was alkylated with 1,4-dibromobutane on the $N^3$ of thymine moiety in presence of potassium carbonate and finally the bromine atom was substituted by sodium azide affording the corresponding azide N-thymine-galactose derivative 4f.

The Gal-T azide derivative 4f was introduced, on the previously prepared, Cy3-oligonucleotide mannose-cores exhibiting four pentynyl (11), four propargyl-diethylene glycyl (19a) or four bis-propargyl-oxymethyl propyl (19d) leading to tetraclusters with with ProTzBuT-Gal or EG₂MTzBuT-Gal respectively and an octagalactocluster with THMEMTzBuTGal motif affording the expected mannose-centered tetra/octagalactocluster oligonucleotide conjugates Man(POProTzBuT-Gal)₄ (37), Man(POEG₂MTzBuT-Gal)₄ (38) and Man[POTHME(MTzBuT-Gal)₂]₄ (39), (FIG. 12).

IV-B Biological Test Protocol:
Test 1:
The binding for PA-IL of the nine resulting glycoclusters was determined by DDI-microarray as described above (see II-B).

Test 2:
For a better understanding of the binding properties, we measured the $IC_{50Lac}$ value of the glycoclusters (results reported in Table 1, Entries 15-18).

Figure 14:
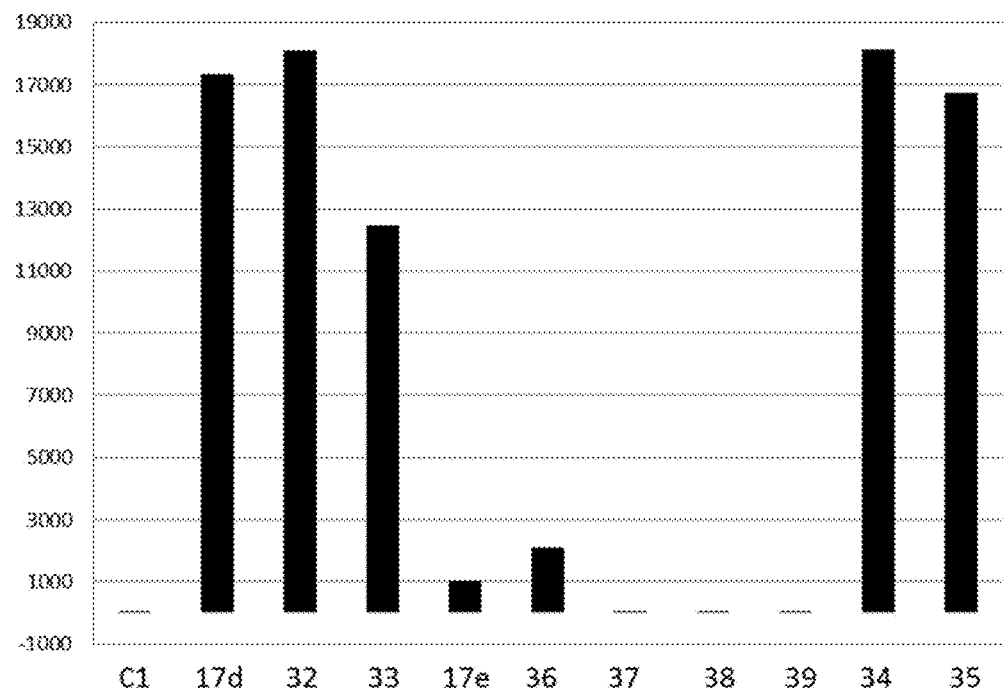
FIG. 14: Fluorescence Arbitrary Unit (a. u.) of linear and hexose-centered glycoclusters bonded with alexa647-PA-IL.

IV-C Test Results:
The results of Test 1 are illustrated in FIG. 14: The increase of the length of the linker from Pro to EG₂M led to an increase of affinity with both TzEG₃-O-Gal and TzAcN-Phe-O-Gal motifs with always a better affinity for the glycocluster with the aromatic motif (TzAcNPhe-O-Gal). In contrast, the increase of length of the linker from EG₂M to EG₄M led to a glycocluster with a lower fluorescent signal suggesting that linkers with too much flexibility and too long are detrimental for the binding to PA-IL.

For the Man-(POProTzAcNAr) clusters the increase of the number of residues from 4 to 8 led to an increase of fluorescent signal Man(POProTzAcNPhe-O-Gal)₄ or 17d vs Man(POProTzAcNPhe-O-Gal)₈ 34. The fluorescent signal of the octacluster was similar to that of the tetracluster with EG₂M linkers. In contrast, the other octacluster Man[POTHME(MTzAcNPhe-O-Gal)₂]₄ 35 displayed a lower fluorescent signal than the two best tetraclusters. Concerning the galactoclusters made from Gal-T, we observed a 635 fluorescent signal about 45 a.u. very similar to the negative control. Increasing of the number of galactoside residues to 8 did not give any improvement of the binding. The reasons for the inhibition of binding to PA-IL for thymine galactoside clusters may be related to steric hindrance considerations since the thymine is directly connected to the C1 of galactopyranose. This finding is similar to the finding of Moni et al, where the binding of PA-IL to galactose clusters was impaired due to the vicinity of the triazole ring. Indeed, in this study, the triazole ring was directly attached to the anomeric carbon of the C-galactoside (Moni, L. et al., (2009) *ChemBioChem* 10, 1369-1378).

The octagalactocluster Man(POProTzAcNPhe-O-Gal)₈ 34 exhibited the highest binding of all the constructions reported so far showing a better cluster effect due to the higher number of galactose motif.

Test 2:
As illustrated in Table 1, Entries 15-18, the potency of each galactocluster was calculated according to mono-EG₃-O-galactose and mono-aromatic galactose. The $IC_{50Lac}$ values confirmed the trends observed by direct fluorescence scanning with a better binding from TzEG₃-O-Gal to TzAcNPhe-O-Gal motifs (entry 15 vs entry 16), a better binding due to the elongation of the linker from Pro to EG₂M (entry 8 vs entry 15 and entry 9 vs entry 16) and the highest binding for the octaglycocluster with ProTzAcN-Phe-O-Gal motifs ($IC_{50Lac}$=6803 entry 17). The second octagalactocluster displayed a lower $IC_{50Lac}$ value of 1807 µM (entry 18) showing that the spatial arrangement has a strong effect on the binding.

Figure 15:
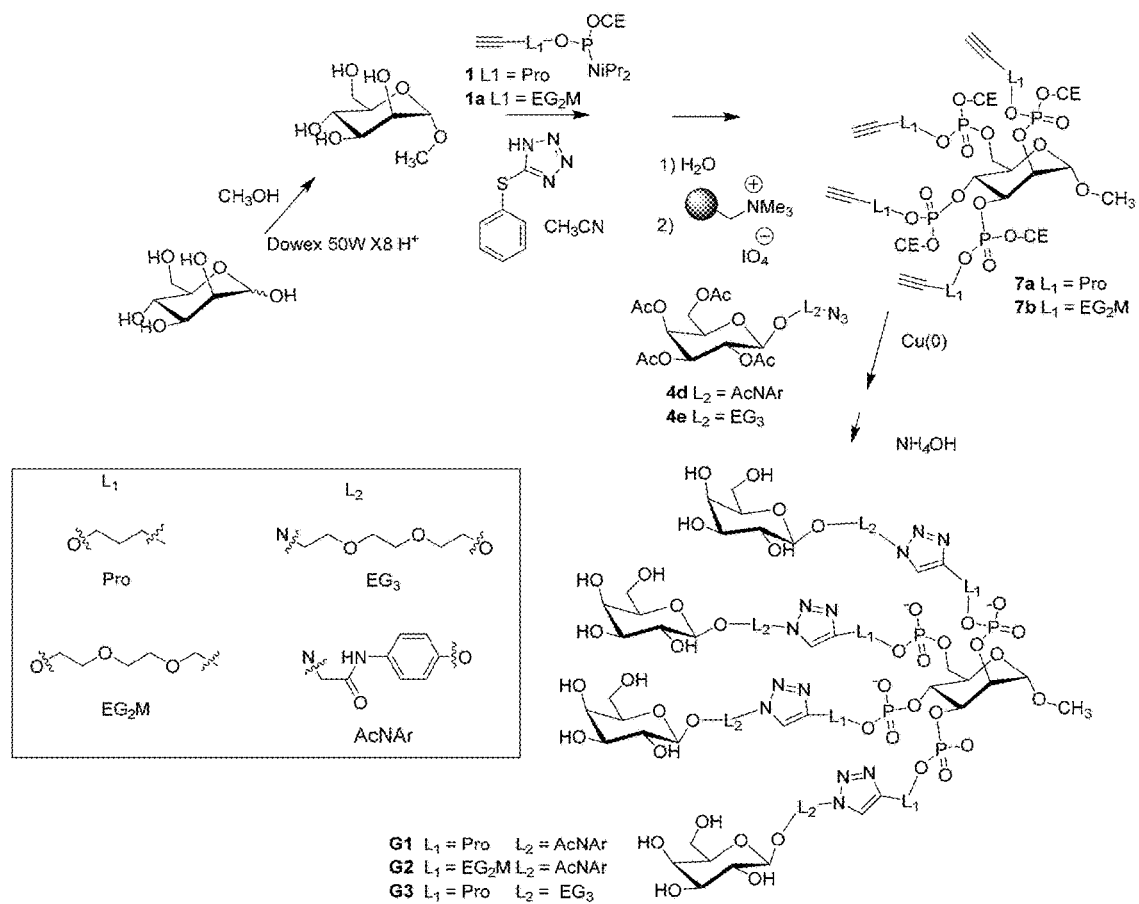
FIG. 15: Synthesis scheme of G1 Man(POProTzAcNPhe-O-Gal)$_4$), G2 (Man(POEG$_2$MTzAcNPhe-O-Gal)$_4$) and G3 (Man(POProTzEG$_3$-O-Gal)$_4$)
Figure 16:
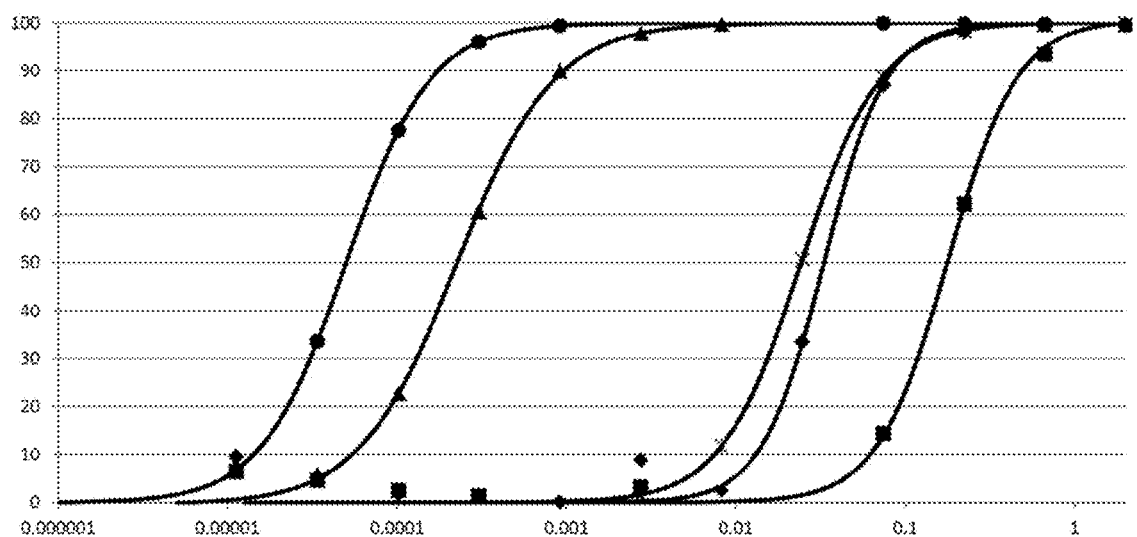
FIG. 16: ELLA curves of the galactomimetics G1 (▲), G2 (●), G3 (×) and monomers Gal-O-Me (■) and Gal-O-Phe-NO$_2$ (♦). % Inhibition (ordinate)—Concentration (abscissa, mM)
Figure 17:
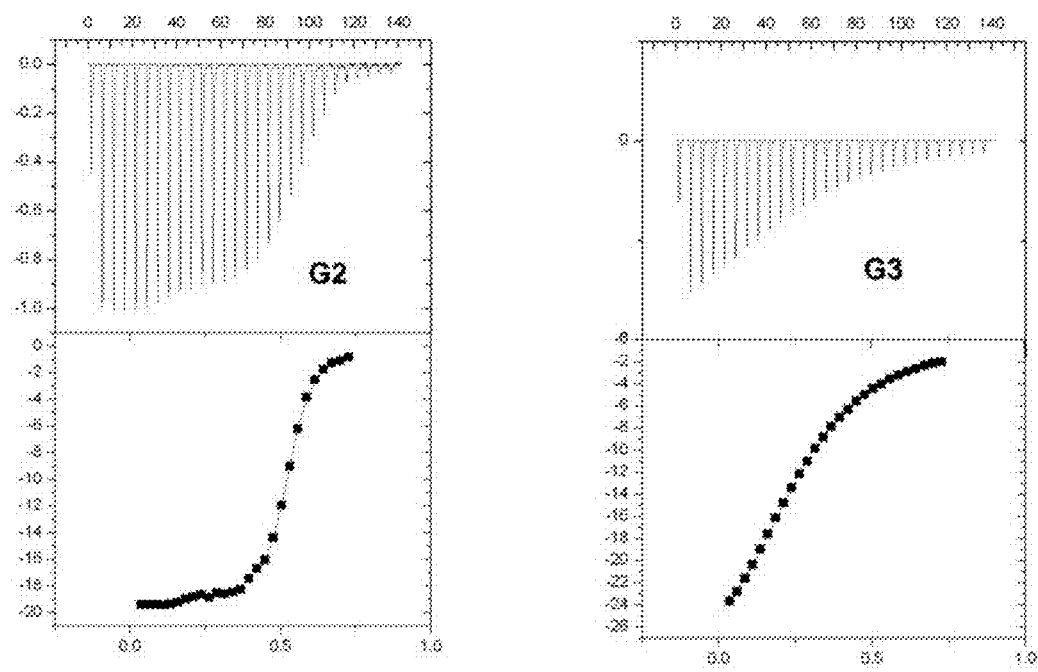
FIGS. 17a and 17b: Microcalorimetry data. The ITC plot (measured by VP-ITC, Microcal) was obtained from the titration of PA-IL with glycomimetics G1-3. The plots in the lower panels show the total heat released as a function of total ligand concentration for the titration shown in the upper panels. The solid lines represent the best least-square fit to experimental data using a one-site model. Kcal/mole of injectant (ordinate)—Concentration (molar ratio).
Figure 17:
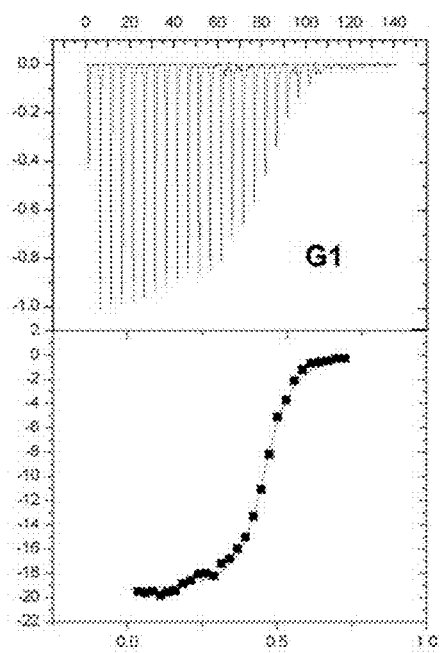

V—Synthesis and Testing of Man(POProTzAcNPhe-O-Gal)₄) G1 and (Man(POEG₂MTzAcNPhe-O-Gal)₄) G2 in Solution:

For biophysical and biological studies, the lead glycoclusters, G1 and G2, as well as the Man(POProTzEG₃Gal)₄ G3 as non-aromatic containing molecule, corresponding to the galactomimetics without the DNA tag, were synthesized in solution at ~100 mg scale (FIG. 15). Their properties against PA-IL were evaluated using hemagglutination inhibitory assay (HIA), Enzyme Linked Lectin Assay (ELLA), Isothermal Calorimetry (ITC), Surface Plasmon resonance (SPR) and DDI glycoarray. For the most potent of them, their inhibition of PA adhesion on epithelial cell line NCI-H292 (ATCC CRL 1848) was also determined.

V-A Synthesis:
Synthesis of glycocluster G1 (Man(POProTzAcNPhe-O-Gal)₄), G2 (Man(POEG₂MTzAcNPhe-O-Gal)₄) and (Man(POProTzEG₃-O-Gal)₄) G3

1-O-methyl-α-D-mannose

A solution of α-D-mannose (2.0 g) in methanol (30 mL) was boiled under reflux for 27 h in the presence of DOWEX-50W X8 resin, $H^+$ form (4.0 g). After filtration and concentration to dryness, the crude product was recrystallized in ethanol to give 1-O-methyl-α-D-mannose (1.58 g, 73%) as a white solid. Analytic data in agreement with literature data (Cadotte, J. E. et al., (1952) *J. Am. Chem. Soc.* 74, 1501-1504).

General Procedure for Phosphorylation:
A solution of 1-O-methyl-α-D-mannose (50 mg, 0.26 mmol, 1 eq) in anhydrous dimethylformamide/acetonitrile (1:1.5, v/v) was stirred for 1 h30 with molecular sieve (3 Å). Then, the alkyne phosphoramidite 46a-b (1.30 mmol, 5 eq) was added and a solution of tetrazole (0.4 M in anhydrous CH₃CN, 6.4 mL, 2.60 mmol, 10 eq). The mixture was stirred at 30° C. for 2 h and the reaction was stopped with H₂O. $A_{26}$ ($IO_4^-$) resin (1.0 g, 2.50 mmol, 9.6 eq) was added and the mixture was stirred for 2 h. After filtration of the resin and addition of dichloromethane (40 mL), the reaction was washed with an aqueous saturated solution of NaHCO₃ (60 mL) and brine (60 mL). The organic layer was dried (Na₂SO₄), filtered and concentrated to afford the desired tetraalkyne mannose derivatives 47a-b.

47a

Obtained as a pale yellow oil (208 mg, 81%). ¹H NMR (300 MHz, D₂O) δ 4.98 (d, J=21.0 Hz, 1H, H-1), 4.87-4.57

(m, 3H, H-2, H-5, H-6), 4.37-4.12 (m, 16H, OCH$_2$CH$_2$CN, POCH$_2$CH$_2$), 3.94-3.89 (m, 1H, H-6), 3.45 (s, 4H, OCH$_3$, H-3), 3.40 (m, 1H, H-4), 2.88-2.78 (m, 8H, CH$_2$CN), 2.39-2.34 (m, 4H, CH$_2$CH$_2$CCH), 2.08-1.90 (m, 8H, POCH$_2$CH$_2$), 1.73-1.64 (m, 4H, CH$_2$CCH). $^{31}$P NMR (162 MHz, CDCl$_3$) δ −1.65-3.01 (m, 1P). $^{13}$C NMR (100 MHz, CDCl$_3$) δ 115.5 (CN) 98.3 (C-1), 81.5 (OCH$_2$CCH), 68.5 (CH$_2$CCH, C-2, C-5, C-6), 65.6 (C-3, C-4), 60.9 (2s, POCH$_2$), 55.7 (OCH$_3$), 27.7 (POCH$_2$CH$_2$), 18.7 (CH$_2$CN), 13.1 (CH$_2$CH$_2$CCH). MS MALDI-TOF$^+$ m/z calcd for C$_{39}$H$_{55}$N$_4$O$_{18}$P$_4$[M+H]$^+$=991.76 found 991.86. HR-ESI-QToF MS (positive mode): m/z calcd for C$_{39}$H$_{55}$N$_4$O$_{18}$P$_4$[M+H]$^+$=991.2465 found 991.2462.

47b

Obtained as a colorless oil (279 mg, 87%). $^1$H NMR (400 MHz, CDCl$_3$) δ 4.93 (d, J=24.2 Hz, 1H, H-1), 4.84-4.79 (m, 1H, H-6), 4.73-4.59 (m, 2H, H-2, H-5), 4.37-4.18 (m, 16H, POCH$_2$CH$_2$CN, POCH$_2$CH$_2$), 4.17-4.12 (m, 8H, OCH$_2$CCH), 3.86-3.80 (m, 1H, H-6), 3.68 (m, 8H, POCH$_2$CH$_2$), 3.63 (s, 17H, OCH$_2$CH$_2$O, H-3), 3.61-3.57 (m, 1H, H-4), 3.38 (s, 3H, OCH$_3$), 2.82-2.74 (m, 8H, CH$_2$CN), 2.46 (m, 4H, OCH$_2$CCH). $^{31}$P NMR (162 MHz, CDCl$_3$) d −1.67-3.11 (m, 1P). $^{13}$C NMR (100 MHz, CDCl$_3$) δ 117.1 (CN) 98.3 (C-1), 79.6 (OCH$_2$CCH), 74.9 (CH$_2$CCH, C-2, C-5, C-6), 70.2-69.7 (2m, POCH$_2$CH$_2$, C-3, C-4), 69.1 (OCH$_2$CH$_2$O), 67.8-62.3 (5m, POCH$_2$), 58.3 (OCH$_2$CCH), 55.7 (OCH$_3$), 19.5 (CH$_2$CN). MALDI-TOF$^+$ m/z calcd for C$_{47}$H$_{71}$N$_4$O$_{26}$P$_4$[M+H]$^+$=1231.96 found 1231.19. HR-ESI-QToF MS (positive mode): m/z calcd for C$_{47}$H$_{71}$N$_4$O$_{26}$P$_4$[M+H]$^+$=1231.3297 found 1231.3307.

General Procedure for 1,3-Dipolar Cycloaddition and Deacetylation of Carbohydrate:

The alkyne-functionalized compounds (47a or 47b) 1.0 eq and the azido-tetraacetylgalactose derivative 48a (Bouillon, C. et al., (2006) *J. Org. Chem.* 71, 4700-4702) or 48b (4 to 4.8 eq) were dissolved in dioxane with triethylammonium acetate buffer (175 μL, 0.1 M, pH 7.7) and nanopowder copper (2 mg). The resulting mixture was stirred overnight at 70° C. Then the reaction was diluted in CH$_2$Cl$_2$ (15 mL), and washed with brine (3×15 mL). The organic layer was dried (Na$_2$SO$_4$), filtered and concentrated to dryness. The resulting product was dissolved in acetone (5 mL) and concentrated ammonia solution (30%) was added (20 mL). The mixture was stirred 1 h at room temperature. After evaporation, the crude product was dissolved in milliQ water, and the solution was passed through a column filled with DOWEX-50W X8 resin, Na$^+$ form. After concentration, the residue was purified by C$_{18}$ flash column chromatography (40 g) (eau/CH$_3$CN/triethylammonium acetate buffer 0.1 M pH 7.7, 97/0/3 to 47/50/3) to afford the desired glycoconjugates.

Man(POProTzAcNPhe-O-Gal)$_4$ G1

Obtained as a pale yellow oil (141 mg, 64%): 47a (100 mg, 0.1 mmol, 1 eq), 48a (211 mg, 0.4 mmol, 4 eq), dioxane (2.0 mL). $^1$H NMR (300 MHz, D$_2$O) δ 7.82-7.72 (4s, 4H, H-triaz), 7.34-7.27 (m, 8H, H-ar), 7.04-6.99 (m, 8H, H-ar), 5.30-5.19 (4s, 8H, C(O)CH$_2$N-triaz), 4.92-4.89 (m, 5H, H-1 gal, H-1 man), 4.86-4.84 (m, 2H, H-2 man, H-3 man), 4.74-4.72 (m, 2H, H-4 man, H-5 man), 3.95-3.93 (m, 10H, H-6 man, OCH$_2$CH2), 3.85-3.68 (m, 24H, H-2 gal, H-3 gal, H-4 gal, H-5 gal, H-6 gal), 3.30 (s, 3H, OCH$_3$), 2.75-2.67 (m, 8H, CH$_2$CH$_2$C-triaz), 1.95-1.81 (m, 8H, CH$_2$CH$_2$CH$_2$) ppm. $^{31}$P NMR (121 MHz, D2O) d 0.86 (s), −0.262 (t) ppm.

$^{13}$C NMR (100 MHz, D$_2$O) d 165.3 (C=O), 153.6 (C$_q$-ar), 147.2 (C$_q$-triaz), 130.8 (C$_q$-ar), 124.1 (CH-triaz), 122.5 (C-ar), 116.4 (C-ar), 100.4 (C-1 gal), 98.3 (C-1 man), 74.78, 72.0, 70.0 (3s, 3C, C-2 gal, C-3 gal, C-4 gal, C-5 gal), 67.9 (OCH$_2$CH$_2$), 64.7, 64.1 (C-2 man, C-3 man, C-4 man, C-5 man, C-6 man), 60.1 (C$_6$ gal), 51.3 (C(O)CH$_2$N-triaz, OCH$_3$), 29.5 (CH$_2$CH$_2$CH$_2$), 28.8 (CH$_2$C-triaz). HPLCt$_R$=11.25 min. MS MALDI-TOF$^-$ m/z calcd for C$_{83}$H$_{113}$N$_{16}$O$_{46}$P$_4$[M−H]$^-$=2194.76 found 2194.84 HR-ESI-QToF MS (positive mode): m/z calcd for C$_{83}$H$_{116}$N$_{16}$O$_{46}$P$_4$[M+2H]$^{11}$=1098.3090 found 1098.3064.

Man(POEG$_2$MTzAcNPhe-O-Gal)$_4$ G2

Obtained as a pale oil (190 mg, 95%): 47b (100 mg, 0.082 mmol, 1 eq), 48a (204 mg, 0.4 mmol, 4.8 eq), dioxane (2.8 mL). $^1$H NMR (600 MHz, D$_2$O) δ 8.19-8.15 (m, 4H, H-triaz), 7.46-7.44 (m, 8H, H-ar), 7.17-7.15 (m, 8H, H-ar), 5.45-5.43 (m, 8H, C(O)CH$_2$N-triaz), 5.05-5.03 (m, 4H, H-1 gal), 4.99 (m, 1H, H-1 man), 4.74 (d, J=2.4 Hz, 8H, OCH$_2$C-triaz), 4.45-4.32 (m, 3H, H-2 man, H-3 man, H-5 man), 4.17-4.10 (m, 6H, ¾ POCH$_2$CH$_2$), 4.06 (d, J=2.4 Hz, 1H, H-4 man), 4.04 (d, J=2.0 Hz, 4H, H-4 gal), 3.89-3.74 (m, 50H, H-2 gal, H-3 gal, H-5 gal, H-6 gal, ¼ POCH$_2$CH$_2$, OCH$_2$CH$_2$), 3.69-3.67 (m, 2H, H-6 man), 3.39 (s, 3H, OCH$_3$) ppm. $^{13}$C NMR (150 MHz, D$_2$O) d 166.1 (C=O), 154.4 (C$_q$-ar), 144.4 (C$_q$-triaz), 131.6 (C$_q$-ar), 126.7 (CH-triaz), 123.4 (C-ar), 117.2 (C-ar), 101.1 (C-1 gal), 98.8 (C-1 man), 75.5, 72.7, 70.7 (3s, 3C, C-2 gal, C-3 gal, C-5 gal), 70.3, 69.7, (2m, 5C, C-2 man, C-3 man, C-4 man, C-5 man, C-6 man), 69.1 (C-4 gal), 68.6 (OCH$_2$CH$_2$), 64.9 (POCH$_2$CH$_2$), 63.2 (OCH$_2$C-triaz), 60.9 (C$_6$ gal), 52.6 (C(O)CH$_2$N-triaz, OCH$_3$). HPLCt$_R$=14.32 min. MS MALDI-TOF$^-$ m/z calcd for C$_{91}$H$_{129}$N$_{16}$O$_{54}$P$_4$ [M−H]$^-$: 2431.95 found 2432.18. HR-ESI-QToF MS (positive mode): m/z calcd for C$_{91}$H$_{132}$N$_{16}$O$_{54}$P$_4$[M+2H]$^{11}$=1218.3513 found 1218.3436.

Man(POProTzEG$_3$-O-Gal)$_4$ G3

Obtained as a pale yellow oil (66 mg, 62%): 47a (50 mg, 0.050 mmol, 1 eq.), 48b (101 mg, 0.200 mmol, 4 eq.), dioxane (1.5 mL). $^1$H NMR (600 MHz, D$_2$O) δ 8.00-7.92 (m, 4H, H-triaz), 5.01 (m, 1H, H-1 man), 4.62-4.64 (m, 8H, CH$_2$N-triaz), 4.48 (dd, J=1.8 Hz, J=7.8 Hz, 3H, H-2 man, H-3 man, H-5 man), 4.45 (d, J=7.8 Hz, 4H, H-1 gal), 4.14-4.12 (m, 4H, ½ GalOCH$_2$), 3.98 (m, 9H, H-6 man, OCH$_2$CH$_2$N-triaz), 3.91-3.88 (m, 5H, H-6 man, H-4 gal), 3.85-3.77 (m, 20H, ½ GalOCH$_2$, POCH$_2$CH$_2$, H-6 gal), 3.76-3.67 (m, 32H, H-2 gal, H-5 gal, OCH$_2$CH$_2$O), 3.61-3.56 (m, 5H, H-3 gal, H-4 man), 3.47 (s, 3H, OCH$_3$), 2.91-2.78 (m, 8H, CH$_2$CH$_2$C-triaz), 1.97 (CH$_2$CH$_2$C-triaz). $^{13}$C NMR (150 MHz, D$_2$O) 103.7 (C-1 gal, C-1 man), 76.0 (POCH$_2$CH$_2$), 75.9, 73.6, 71.6 (3s, 3C, C-2 gal, C-3 gal, C-5 gal), 70.6, 70.5, 70.4, 70.3, 70.2 (C-2 man, C-3 man, C-4 man, C-5 man, C-6 man, OCH$_2$CH$_2$O), 70.0 (OCH$_2$CH$_2$N-triaz), 69.5 (C-4 gal, Gal OCH$_2$), 61.8 (d, C-6 gal)), 51.0 (CH$_2$N-triaz), 44.0 (CH$_2$CH$_2$C-triaz), 30.4 (CH$_2$CH$_2$C-triaz). MS MALDI-TOF$^-$ m/z calcd for C$_{75}$H$_{133}$N$_{12}$O$_{50}$P$_4$ [M−H]$^-$=2126.80 found 2126.54. HR-ESI-QToF MS (positive mode): m/z calcd for C$_{75}$H$_{136}$N$_{12}$O$_{50}$P$_4$[M+2H]$^+$=1064.3709 found 1064.3835.

V-B Biological Tests:

The binding of PA-IL to galactoclusters was probed as the ability of the clusters to inhibit the binding of PA-IL to rabbit erythrocytes (Hemagglutination inhibition assay, HIA) or to surface bound galactosyl modified polyacrylamide either by Surface Plasmon Resonance (SPR), Enzyme Linked Assay (ELLA) Inhibition was measured with competitive assays. In HIA experiments, the minimal inhibitory concentration (MIC) is the minimal concentration of galactocluster that inhibit the hemagglutination of rabbit erythrocytes in presence of the lectin. The lower the MIC the highest is the binding of the galactocluster to the lectin. SPR and ELLA were used to determine the $IC_{50}$ value. The $IC_{50}$ is the concentration of galactocluster that inhibit 50% of the binding of PA-IL to surface bound gal-PAA. The lower the $IC_{50}$ value as determined by SPR ($^{SPR}IC_{50}$) and ELLA ($^{ELLA}IC_{50}$), the higher is the binding of PA-IL to the galactocluster.

1-O-Methyl-β-D-galactoside (GalOMe) and 1-O-p-nitrophenyl-β-D-galactoside (GalOArNO$_2$) were used as reference ligands. These two reference ligands allow separating the impact of the phenyl aglycon on the binding and the glycoside cluster effect. $β_{Me}$ and $β_{Ar}$ are the relative potencies of the galactoclusters with reference to GalOMe and to GalOArNO$_2$ respectively.

Hemagglutination Inhibition Assays (HIA):

Hemagglutination inhibition assays (HIA) were performed in U-shaped 96-well microtitre plates. Rabbit erythrocytes were purchased from Biomérieux and used without further washing. Erythrocytes were diluted to a 8% solution in NaCl (100 mM). PA-IL solutions of 3 µM were prepared in TRIS-HCl 20 mM (TRIS=tris(hydroxymethyl)aminomethane), NaCl 100 mM, and CaCl$_2$ 100 mM. The hemagglutination unit (HU) was first obtained by addition of the 4% erythrocyte solution (50 µL) to aliquots (50 µL) of sequential (twice) lectin dilutions. The mixture was incubated at 25° C. for 30 min. The HU was measured as the minimum lectin concentration required to observe hemagglutination. For the following lectin-inhibition assays, lectin concentrations of 4 HU were used. For PA-IL, this concentration was found to be 3 µM. Subsequent inhibition assays were then carried out by the addition of lectin solution (25 µL, at the required concentration) to sequential dilutions (50 µL) of glycoclusters, monomer molecules, and controls. These solutions were incubated at 37° C. for 30 min, then 8% erythrocyte solution (25 µL) was added, followed by an additional incubation at 37° C. for 1 h. The minimum inhibitory concentration for each molecule was determined for each duplicate.

Determination of Lectin Concentration by Using ELLA:

96-Well microtiter plates (NuncMaxisorb) were coated with α-PAA-Gal(PAA=polyacrylamide) for PA-IL (Lectinity Holding, Inc.): 100 µL of 5 µg·mL$^{-1}$ in carbonate buffer, pH 9.6 for 1 h at 37° C., then blocking at 37° C. for 1 h with 100 µL per well of 3% (w/v) bovine serum albumin (BSA) in phosphate buffer solution (PBS). Lectin solutions (75 µL) were diluted (1:2) starting from 30 µg·mL$^{-1}$. After 1 h incubation at 37° C. and three washes with T-PBS (PBS that contained 0.05% Tween 20), horseradish peroxidase (HRP)-streptavidin conjugate (100 µL; dilution 2:8000; Boehringer-Mannheim) was added and left for 1 h at 37° C. Coloration was developed by using 100 µL per well of 0.05% phosphate/citrate buffer that contained o-phenylenediaminedihydrochloride (0.4 µg·mL$^{-1}$) and urea hydrogen peroxide (0.4 mg·mL$^{-1}$) (OPD kit, Sigma-Aldrich) for 15 min and stopped with sulfuric acid (50 µL, 30%). Absorbance was then read at 490 nm using a microtiter plate reader (BioRad 680). The concentration of biotinylatedlectins was determined by plotting the relative absorbance versus lectin concentration. The concentration that led to the highest response in the linear area was selected as the standard lectin concentration for the subsequent inhibition experiments. The final concentrations were 0.5 µg·mL$^{-1}$ for PA-IL.

Isothermal Titration Microcalorimetry (ITC):

Recombinant lyophilized PA-IL was dissolved in buffer (0.1 M TRIS-HCl, 6 µM CaCl$_2$, pH 7.5) and degassed. Protein concentration (between 50 and 270 µM depending on the ligand affinity) was checked by measurement of optical density by using a theoretical molar extinction coefficient of 28000. Carbohydrate ligands were dissolved directly into the same buffer, degassed, and placed in the injection syringe (concentration: 175 µM). ITC was performed using a VP-ITC MicroCalorimeter from MicroCal Incorporated. PA-IL was placed into the 1.4478 mL sample cell, at 25° C. Titration was performed with 10 µL injections of carbohydrate ligands every 300 s. Data were fitted using the "one-site model" using MicroCal Origin 7 software according to standard procedures. Fitted data yielded the stoichiometry (n), the association constant ($K_a$), and the enthalpy of binding (ΔH). Other thermodynamic parameters (i.e., changes in free energy ΔG and entropy ΔS) were calculated from the equation $ΔG=ΔH-TΔS=-RTlnK_a$ in which T is the absolute temperature and R=8.314 J·mol$^{-1}$·K$^{-1}$. Two or three independent titrations were performed for each ligand tested.

Surface Plasmon Resonance (SPR):

SPR inhibition experiments were performed using a Biacore 3000 instrument at 25° C. Measurements were carried out on two channels with two immobilized sugars: α-L-fucose (channel 1) and α-D-galactose (channel 2). Immobilization of sugars was performed at 25° C. using running buffer (HBS) at 5 mL·min$^{-1}$. Immobilization on each channel (CM5 Chip) was performed independently as follows. First, the channel was activated by injecting a fresh mixture of EDC/NHS (35 µL, 420 s). Then a solution of streptavidin (100 mg·mL$^{-1}$ in 0.1 mM AcONa pH 5 buffer) was injected (50 µL, 600 s). The remaining reactive species were quenched by injecting ethanolamine (1M, 35 µL, 420 s) into the solution. Finally, a solution of the desired biotinylated-polyacrylamide-sugar (lectinity, 200 mg·mL$^{-1}$) was coated onto the surface (50 µL, 600 s) through streptavidin-biotin interaction. This procedure led to 804 RU (resonance units) (fucoside) and 796 RU (galactoside) of immobilized sugars on channels 1 and 2, respectively Inhibition experiments were performed with the galactosylated channel 2 and plots represent subtracted data (channel 2-channel 1). The running buffer for PA-IL experiments was HEPES 10 mm, NaCl 150 mM, CaCl$_2$ 10 mM, Tween P20 0.005%, pH 7.4. Inhibition studies consisted of the injection (150 µL, 10 µL·min$^{-1}$, dissociation 120 s) of incubated (>1 h, RT) mixtures of PAIL (5 mm) and various concentrations of inhibitor (twofold cascade dilutions). For each inhibition assay, PA-IL (5 µM) without inhibitor was injected to observe the full adhesion of the lectin onto the sugar-coated surface (0% inhibition). The CM5 chip was fully regenerated by successive injections of d-galactose (2×30 µL, 100 mm in running buffer). Binding was measured as RU over time after blank subtraction, and data were then evaluated using the BIAevaluation Software version 4.1. For $IC_{50}$ evaluation, the response ($R_{eq}$-fitted) was considered to be the amount of lectin bound to the carbohydrate-coated surface at equilibrium in the presence of a defined concentration of inhibitor. Inhibition curves were obtained by plotting the percentage of inhibition against the inhibitor concentration (on a logarithmic scale) by using Origin 7.0 software (OriginLab Corp.), and $IC_{50}$ values were extracted from sigmoidal fit of the inhibition curve.

Microarray

Fabrication of Microarray

Microstructured borosilicate glass slides (Nexterion Glass D, Schott Germany) were fabricated using standard photolithography and wet etching process detailed elsewhere (Mazurczyk, R. et al., (2008) *Sens. Actuators, B*128, 552-559; Vieillard, J. et al., (2007) *J. Chromatogr. B*845, 218-225; Vieillard, J. et al., (2008) *Microelectron. Eng.* 85, 465-469). Microstructured slides featured 40 square wells (3 mm width, 60±1 µm depth).

The resulting fabricated slides were functionalized according to the protocol reported in Dugas, V., and Chevalier, Y. (2003) *J. Colloid Interface Sci.* 264, 354-361; Dugas, V. et al, (2004) *Sens. Actuators, B*101, 112-121; Phaner-Goutorbe, M. et al., (2011) *Materials Science & Engineering C-Materials for Biological Applications* 31, 384-390. The slides were washed in freshly prepared piranha rinsed in DI water and dried under dry nitrogen at 150° C. for 2 h. After return to room temperature, tert-butyl-11-(dimethylamino)silylundecanoate in dry pentane was allowed to react with glass slide surfaces (RT). After pentane evaporation, the slides were heated at 150° C. overnight and finally washed in THF and water. The tert-butyl ester function was converted into NHS ester. Alternatively, the slides can be funtionalized in gas phase. The washing procedures are similar.

Amino modified oligonucleotides were purchased from Eurogentec. Spotting of 0.3 nL of the various oligonucleotides at 25 µM in PBS 10× (pH 8.5) at the bottom of each reactor (64 spots per well). The substitution reaction was performed overnight at room temperature in a water saturated atmosphere, and then, water was allowed slowly to evaporate. Washing of the slides was performed with SDS (0.1%) at 70° C. for 30 min and deionized water briefly.

All slides were blocked with BSA 4% solution in PBS 1× (pH 7.4, 37° C., 2 h) and washed successively in PBS-Tween 20 (0.05%), PBS 1× (pH 7.4) and DI water before being dried by centrifugation.

Lectin Labeling: Alexa647 Labeling of PA-IL Lectin

PA-IL lectin was labeled with Alexa Fluor® 647 Microscale Protein Labeling Kit (A30009) from Invitrogen. Labeled-lectin concentration and the dye to lectin ratio were estimated by optical density read out with a dual beam spectrometer (Safas) equipped with a microcuvette (Hellma, 5 µl, 1 mm optical path). The absorbance at 281 nm and 650 nm were measured. PA-IL concentration was estimated to be 11.58 µM with a degree of labeling of 0.51 dyes for tetrameric PA-IL.

"In Solution" Biological Recognition

The methodologies for Kd and $IC_{50}$ value determination have been previously reported (Gerland, B. et al., (2012) *Bioconjugate Chem.* 23, 1534-1547; Zhang, J. et al., (2009) *Chem. Comm.*, 6795-6797; Zhang, J. et al., (2009) *Biosens. Bioelectron.* 24, 2515-2521).

$K_d$ Determination:

Mimetic G1 Man(POProTzAcNPhe-O-Gal)$_4$ or 32 Man (POEG$_2$MTzAcNPhe-O-Gal)$_4$ (1 µM final concentration) were diluted in PBS-0.02% Tween$_{20}$-2% BSA solution. CaCl$_2$ (1 µg/mL final concentration) was added. PA-IL at the desired final concentration was then added. 2 µL of each solution (corresponding to the desired PA-IL concentration) were poured in the corresponding microwells. The slide was incubated (3 h, 37° C.) in a water vapor saturated chamber and finally washed in PBS-Tween 20 (0.02%, 5 min, 4° C.) and dried. A Microarray scanner, GenePix 4100A software package (Axon Instruments; $\lambda_{ex}$ 532/635 nm and $\lambda_{em}$ 575/670 nm) was used for fluorescent imaging of both fluorophore (Cy3 and Alexa 647). The average of the mean fluorescence signal was calculated from eight spots. The resulting Langmuir Isotherms were linearised using Scatchard plot to give the $K_d$ values at the ordonnate intercept.

Adhesions Test on Cells

Bacterial and Cell Culture.

Epithelial cell line NCI-H292 (ATCC CRL 1848), originating from a human lung mucoepidermoid carcinoma, was maintained in 25-cm$^2$ tissue culture flasks (Nunc) in RPMI 1640 medium (Gibco) supplemented with 10% fetal calf serum (Boehringer) without antibiotics. This medium is hereafter referred to as maintenance medium. Cells were passaged twice weekly with a split ratio of 1:6. All cell cultures were incubated at 37° C. in a humidified atmosphere containing 5% $CO_2$. The cell count and viability was determined by light microscopy after trypan blue staining. The *Pseudomonas aeruginosa* reference strain PAO1 was grown in Luria-Bertani medium at 37° C. for 16 h. Cells were washed two times in Dulbecco's phosphate buffered saline (DPBS) solution and diluted to obtain a cellular density of approximately $5.10^6$ CFU/mL.

Bacterial Adhesion Assays.

For the adhesion assays, NCI-H292 cells were cultivated to confluent monolayers ($5.10^5$ cells per well) into 24-well microtiter plates containing 1 mL of maintenance medium. Plates were washed two times with 1 mL Dulbecco's phosphate buffered saline (DPBS) (137 mM NaCl, 8 mM Na$_2$PO$_4$, 1.5 mM KH$_2$PO$_4$, 2.6 mM KCl), pre-warmed to 37° C. and nonspecific binding was blocked by incubation for 1 h at 37° C. with 0.5% (wt/vol) bovine serum albumin in DPBS. Before interaction with bacteria, the preparations were rinsed again twice with prewarmed DPBS. 100 µL of bacterial suspension were then added to each well to obtain a MOI of 1 ($5.10^5$ CFU/mL/$5.10^5$ cells). Plates were then incubated 2 h at 37° C. Non-adherent bacteria were removed by rinsing the preparations five times with DPBS. Cells were lysed by incubation for 30 min at 37° C. with a 0.2% (v/v) Triton X-100 solution. Serial dilutions were prepared using DPBS, and 100 µL aliquots were plated in triplicate on LB plates and incubated at 37° C. for 24 h.

For adherence inhibition, only the galactomimetic G1 (Man(POProTzAcNPhe-O-Gal)$_4$) was tested. Galactomimetic G1 was added to wells at a final concentration ranging from 0 to 2 mM.

V-C Results

In the HIA assay, G2 Man(POEG$_2$MTzAcNPhe-O-Gal)$_4$ displayed the lowest MIC of the mimetics and Man(POProTzEG$_3$-O-Gal)$_4$ G3 displayed the highest one. Mimetic G1 Man(POProTzAcNPhe-O-Gal)$_4$ had an intermediate MIC (Table 3). The relative potencies of mimetics G1, G2 and G3 in respect with GalOMe are 128, 513 and 4, respectively. Hence, the increase for Man(POProTzEG$_3$-O-Gal)$_4$ G3 remains limited. In fact, the MIC per galactose residues is the same. In contrast, mimetics G1 and G2 exhibit a strong increase of potency with a marked benefit for G2 bearing the longest linker between the galactose residue and the mannose core. The calculated potencies in respect with GalOArNO$_2$ of 16 and 65 for mimetics G1 and G2 respectively clearly showed the glycocluster effect with an increase per residue of 4 and 16 respectively. Therefore, the potency increases are not only related to the presence of the aromatic ring but also to a multivalent effect.

TABLE 3

Hemagglutination Inhibition Assay (HIA). MIC stands for minimal inhibitory concentration. Potency (β): $β_{Me}$ or $β_{Ar}$ corresponds to the ratio of the MIC of Gal-OMe or Gal-OArNO2 over the MIC of the considered molecule.

| Ligand | Valence | MIC (mM) | $β_{Me}$ | $β_{Ar}$ |
|---|---|---|---|---|
| Gal-OMe | 1 | 16 | 1.0 | 0.13 |
| Gal-ArNO$_2$ | 1 | 2.0 | 8.0 | 1.0 |
| Man(POProTzAcNPhe-O-Gal)G1 | 4 | 0.125 | 128 | 16 |
| Man(POEG$_2$MTzAcNPhe-O-Gal)$_4$G2 | 4 | 0.031 | 516 | 65 |
| Man(POProTzEG$_3$-O-Gal)$_4$G3 | 4 | 4.0 | 4.0 | 0.5 |

In the $^{ELLA}IC_{50}$ and $^{SPR}IC_{50}$, the potency of Man(POProTzEG$_3$-O-Gal)$_4$ is slightly better than for Gal-Ar on the contrary to HIA (Table 4). This suggests that in fact the potencies of the two molecules are in fact similar. Both $^{ELLA}IC_{50}$ and $^{SPR}IC_{50}$ confirmed that G1 Man(POProTzAcNPhe-O-Gal)$_4$ and G2 Man(POEG$_2$MTzAcNPhe-O-Gal)$_4$ had an improved potency compared to the monovalent ligands and to Man(POProTzEG$_3$-O-Gal)$_4$. It was also confirmed that G2 Man(POEG$_2$MTzAcNPhe-O-Gal)$_4$ was the best ligand. However, the extent of these improvements was assay dependent. Indeed, potencies in respect with Gal-ArNO$_2$ for mimeticsl to 3 were 127, 550 and 1.2 for IC$_{50}$ values determined by ELLA and 2.0, 7.4 and 1.7 for IC$_{50}$ values determined by SPR. Hence, in the case of $^{SPR}IC_{50}$, no clear multivalent cluster effect can be evidenced. Such discrepancy in the extent of the glycoside cluster effect has already been reported in the literature (Lundquist, J. J., and Toone, E. J. (2002) Chem. Rev. 102, 555-578).

TABLE 4

IC$_{50}$ values of galactosylated ligands determined by Enzyme linked Lectine Assay (ELLA) and by Surface Plasmon Resonance (SPR) $β_{Me}$ is the ratio of the IC$_{50}$ value of Gal-OMe over the IC$_{50}$ value of the considered molecule. Similarly, $β_{Ar}$ is the ratio of the IC$_{50}$ value of Gal-ArNO$_2$ over the IC$_{50}$ value of the considered molecule.

| | ELLA | | | SPR | | |
|---|---|---|---|---|---|---|
| Ligand | IC$_{50}$ (µM) | $β_{Me}$ | $β_{Ar}$ | IC$_{50}$ (µM) | $β_{Me}$ | $β_{Ar}$ |
| Gal-OMe | 183 | 1.0 | 0.2 | 49 | 1.0 | 0.14 |
| Gal-ArNO$_2$ | 33.0 | 5.5 | 1.0 | 6.7 | 7.3 | 1.0 |
| G1 Man(POProTzAcNPhe-O-Gal)4 | 0.26 | 704 | 127 | 3.3 | 15 | 2.0 |
| G2 Man(POEG$_2$MTzAcNPhe-O-Gal)4 | 0.06 | 3050 | 550 | 0.91 | 54 | 7.4 |
| G3 Man(POProTzEG$_3$-O-Gal)4 | 27.6 | 6.6 | 1.2 | 4.0 | 12 | 1.7 |

Microtiter plates were modified with PAA-galactose. Slides were incubated with increasing concentration of galactosylated ligands. The IC$_{50}$ is the concentration of galactomimetic that can displace 50% of the initial adhesion of PA-IL to the galactose-PAA modified surface. The lowest the IC$_{50}$ as determined the strongest is the binding of the studied molecule to PA-IL. ELLA: This IC$_{50}$ will be referred here after $^{ELLA}IC_{50}$. SPR: This IC$_{50}$ will be referred here after $^{SPR}IC_{50}$.

IC$_{50}$ values of the three mimetics were previously determined using DNA directed immobilization glycoarray using 17d, 32 and C3 in comparison with 31 used as a reference monovalent ligand (Table 6) (Zhang, J. et al., (2009) Biosens. Bioelectron. 24, 2515-2521; Goudot, A. et al., (2013) Biosens. Bioelectron. 40 153-160). In this case, the IC$_{50}$ value corresponds to the concentration of lactose needed to inhibit 50% of PA-IL interaction with surface bound clusters. Thus, the highest the IC$_{50}$ value, the better is the binding. Relative potency of 177, 264 and 1.8, were determined. The present IC$_{50}$ values determined by ELLA are in agreement with those determined by the glycoarray with the same order of magnitude between the different mimetics.

TABLE 6

IC$_{50}$ values for DNA-galactomimetics determined by DDI-glycoarray using lactose as inhibitor.

| Ligand | Valence | microarray IC$_{50}$Lac (µM) | β |
|---|---|---|---|
| 31 | 1 | 16 | 1 |
| 17d | 4 | 2826 | 177 |
| 32 | 4 | 4218 | 264 |
| G3 | 4 | 29 | 1.8 |

Isothermal microcalorimetry measurements of the interaction between PA-IL and the three galactoclusters G1, G2, G3 were undertaken and compared with data obtained previously with the GalOMe (Table 7) (Chabre, Y. M. et al., (2011) Chem. Eur. J. 17, 6545-6562). In the case of G3 Man(POProTzEG$_3$-O-Gal)$_4$, it was measured a Kd value of 11 µM corresponding to a moderate increase of potency in respect with GalOMe of 8.5 fold. The stoechiometry (0.28) suggest that the four galactose residues are linked to PA-IL monomers. Therefore, our results suggested the entropic cost upon the interaction is not compensated by enthalpic consideration leading to a similar Kd for both the multivalent G3 Man(POProTzEG$_3$-O-Gal)$_4$ and the monovalent Gal-Ar. Galactomimetics G1 and G2 exhibited a strong increase of potency of 485- and 599-fold respectively. The stoechiometry of G1 Man(POProTzAcNPhe-O-Gal)$_4$ or G2 Man(POEG$_2$MTzAcNPhe-O-Gal)$_4$ were similar (0.46 and 0.52, respectively), suggesting that two galactose residues were involved simultaneously with PA-IL monomers. The entropic cost for both molecules is about 3 to 4 times lower than the one observed for G3 Man(POProTzEG$_3$-O-Gal)$_4$. Both molecules have similar enthalpic contributions and not so different from the −53 KJmol$^{-1}$ observed by Ceccioni et al with aromatic monovalent ligands (Cecioni, S. et al., (2012) Chem. Eur. J. 18, 6250-6263). However surprisingly, despite the presence of more flexible linker due to the diethylene glycol arm, the entropic cost of G2 Man(POEG$_2$MTzAcNPhe-O-Gal)$_4$ was lower than the one observed with G1 Man(POProTzAcNPhe-O-Gal)$_4$. A reason for this may be due to the hydrophobic nature of the linker for Man(POProTzAcNPhe-O-Gal)$_4$ leading to higher and increased dehydration entropic cost.

In parallel, the Kd of 17d Man(POProTzAcNPhe-O-Gal)$_4$ was measured on microarray using Langmuir isotherm leading to a Kd value of 196 nM similar to the one measured with ITC. However, the measured Kd value of 32 Man(POEG$_2$MTzAcNPhe-O-Gal)$_4$ was 83 in the same range of magnitude than the one measured with ITC.

TABLE 7

Titration microcalorimetry data for the interaction between PA-IL and galactomimetics Gl, G2, G3.

| Glycoclusters | n | Kd (μM) | -ΔH (kJ/mol) | -TΔS (kJ/mol) | -ΔG (kJ/mol) | $\beta_{Me}^{a}$ | $^{a}$Kd (μM) |
|---|---|---|---|---|---|---|---|
| Gal-OMe | 1 | 94$^{a}$ | 42.8 | 19.8 | 23 | 1 | |
| Man(POProTzAcNPhe-O-Gal)$_4$ G1 | 0.46 ± 0.01 | 0.194 ± 0.007 | 81.4 ± 0.1 | 43 | 39 | 485 | 196 |
| Man(POEG$_2$MTzAcNPhe-O-Gal)$_4$ G2 | 0.52 ± 0.01 | 0.157 ± 0.002 | 78 ± 3 | 39 | 39 | 599 | 83 |
| Man(POProTzEG$_3$-O-Gal)$_4$ G3 | 0.28 ± 0.02 | 11 ± 3 | 134 ± 3 | 105 | 28 | 8.5 | nd |

$^{a}$Kd values determined from 17d, 32 and C3.

Figure 18:
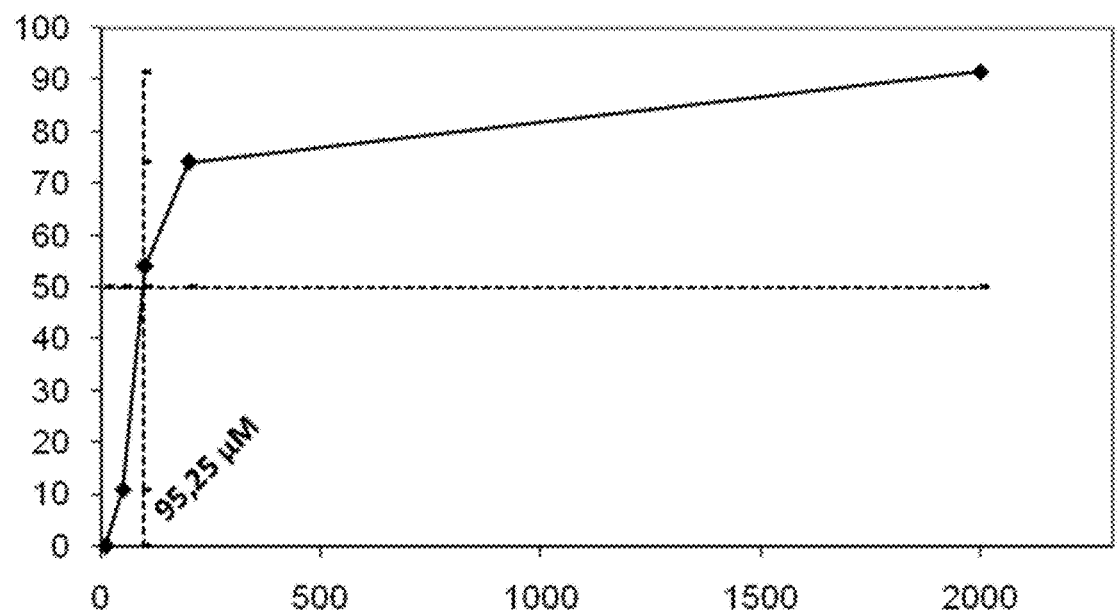
FIG. 18: Bacterial adhesion assays. Percentage of inhibition of *Pseudomonas aeruginosa* (PAO1) adhesion on NCI-H292 cells with variable concentration of galactomimetics G1 (Man(POProTzPhe-O-Gal)$_4$) inhibitor. % Inhibition (ordinate)—Concentration (abscissa, μM)
Figure 19:
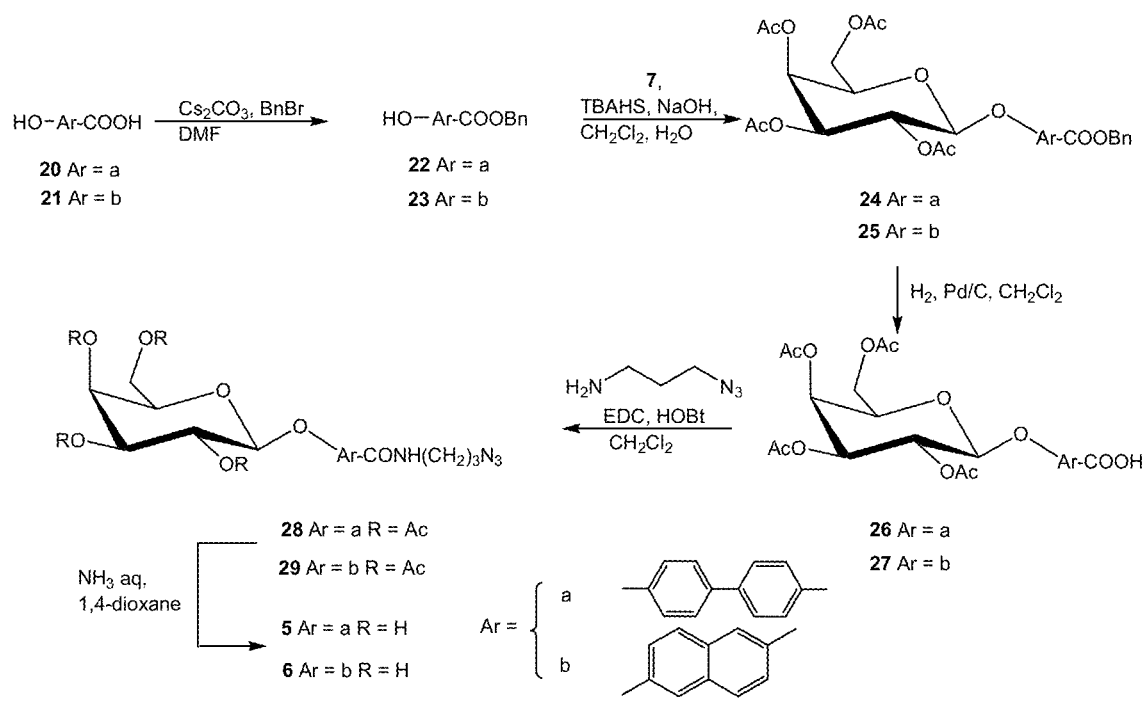
FIG. 19 is a scheme illustrating the synthesis of O-biphenyle, O-naphthyle galactosides 5 and 6.
Figure 20:
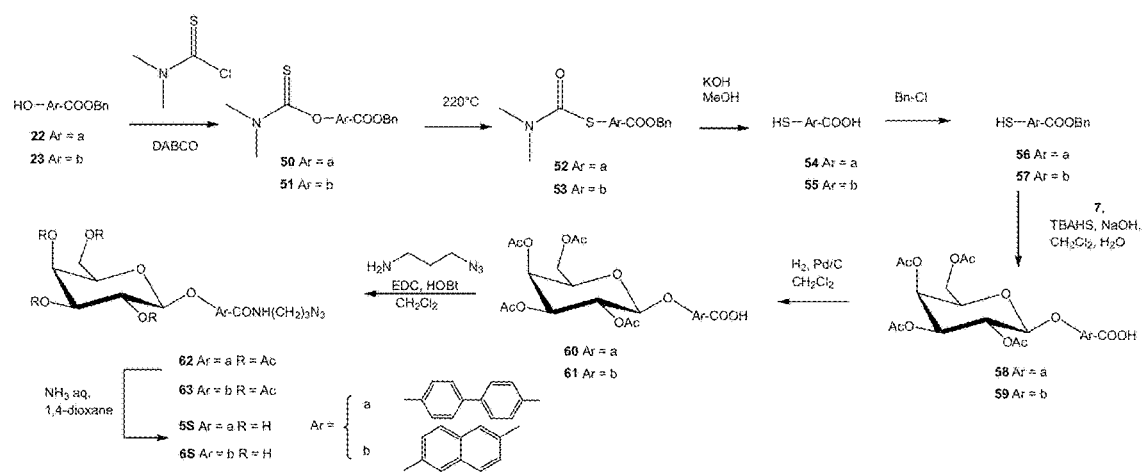
FIG. 20 is a scheme illustrating the synthesis of S-biphenyle, S-naphthyle galactosides 5S and 6S.
Figure 21:
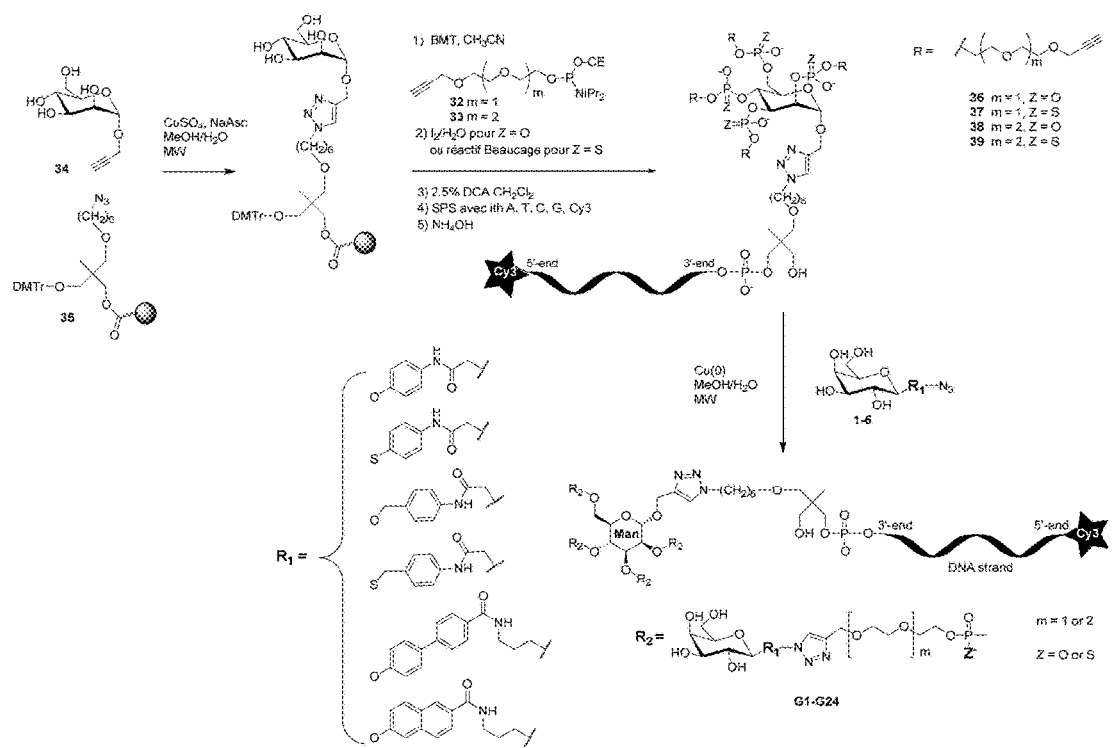
FIG. 21 is a scheme illustrating the synthesis of glycoclusters G1-G24.

On the cellular level, only the galactomimetic G1 (Man(POProTzAcNPhe-O-Gal)$_4$) adhesion inhibitory effect was assessed as it exhibited a strong binding to PA-IL according to physic-chemical characterization experiments. *P. aeruginosa* adherence to NCI-H292 cells was assessed after 2 h incubation with or without the galactomimic inhibitor (FIG. 18).

The number of adherent bacteria decreases gradually with an increase in galactomimetic concentration in the medium. No significant inhibition was observed for concentration below 50 μM. FIG. 18 represents the inhibition percentage of *P. aeruginosa* adherence to NCI-H292 cells as a function of G1 (Man(POProTzPhe-O-Gal)$_4$) concentration in the medium. The adhesion IC$_{50}$ ($^{adh}$IC$_{50}$) was 95.25 μM as determined graphically.

Bacterial adhesion assay shows that G1 Man(POProTzAcNPhe-O-Gal)$_4$ is an inhibitor of bacterial adhesion. The bacterial adhesion assay validates that adhesion of PA to host cells can be inhibited by galactoclusters.

It is well known that only a small amount of lectins are exposed on the bacterial cell (Glick and Garber et al., 1983). Nevertheless, this small amount is sufficient to promote bacterial attachment to host epithelial cells (Plotkowski et al., 1989; Laughlin et al., 2000; Chemani et al., 2009) even if direct implication of PA-IL in this adhesion haven't been demonstrated yet. Several research groups already described inhibition of adhesion of PA to host tissue, decrease of lung colonization or increase in lung clearance in animal models infected by PA and this consecutively to treatments with diverse galactosides targeting PA-IL (Chemani et al., 2009; Gilboa-Garber N, 2011; Gustke et al., 2012). We believe that the galactomimetics directed against PA-IL represent a new class of inhibitor of PA adhesion to host tissue representing a promising future to prevent PA infection.

The affinities of glycocluster G25-G48 toward PA-IL have been evaluated thanks to the glycoarray.

The expected Kd values for compounds G25-G30 are 1 to 50 nM, preferentially 50 to 100 nM and for compounds G31-G48, Kd values are 1 to 50 nM, preferentially 1 to 100 nM.

VI—Conclusions:

PA colonization of host tissue and biofilm formation give to the bacteria a selective advantage against antibiotic therapy. PA-IL is a virulence factor suspected to be involved in PA adhesion Inhibition of PA-IL with multivalent galactosylated molecules is forecasted as a mean to inhibit PA-adhesion. Herein, the affinity of galactose clusters to PA-IL was evaluated using 5 different techniques. Ultimately, the five techniques demonstrated that galactomimetic G1 (Man(POProTzAcNPhe-O-Gal)$_4$) had a strong binding to PA-IL. It was able to inhibit PA adhesion to NCI-H292 with an IC$_{50}$ below 100 μM.

Both techniques (IC$_{50}$ and Kd) gave similar affinities. The best glycoclusters were those with O-naphthyl (G21-G24), O-biphenyl (G17-G20) and O-phenyl (G1 and G3) exhibiting Kd values from 14 to 48 nM. Glycoclusters with S-benzyl (G13-G16) and phosphorothioate EG2 O-phenyl (G2) gave lower affinity with Kd values from 49 to 70 nM, followed with S-benzyl (G13-G16) and phosphorothioate EG3 O-phenyl (G4) with Kd values between 71 and 85 nM. Finally, glycocluster with O-benzyl (G5-G8) displayed the lowest affinities with Kd value from 85 to 170 nM.

The invention has been described with reference to preferred embodiments. However, many variations are possible within the scope of the invention.

The invention claimed is:

1. A molecule of formula (II):

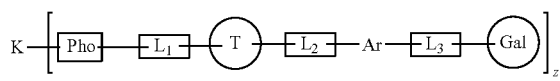

Wherein

K is a carbohydrate selected from the group consisting of mannose, galactose, glucose, arabinose, xylose, ribose and lactose Pho is a phosphorous group selected from the group consisting of:

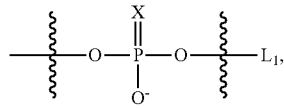

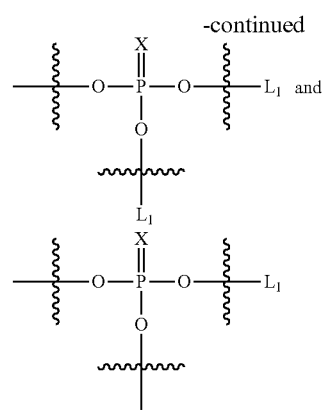

Wherein X is selected from the group consisting of O or S, One or two oxygen atoms of the phosphate group being linked by a covalent link to a L1 linker arm, L1 is a linker arm selected from the group consisting of:
a linear or branched $C_1$-$C_3$ alkyl di radical, a linear, branched or cyclic $C_4$-$C_6$ alkyl di radical, a linear, branched or cyclic $C_7$-$C_{12}$ alkyl di radical possibly comprising one to three ether bridges —O—, a poly(ethylene glycol) di radical comprising 2, 3, 4, 5 or 6 ethylene glycol units,
a polypropyleneglycol di radical comprising 2, 3, 4, 5 or 6 propylene glycol units,
T is a connecting group selected from:
a triazole di-radical

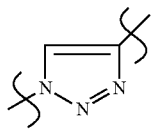

L2 is a linker arm selected from the group consisting of

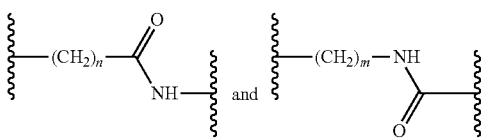

n and m is an integer selected from 1, 2, 3, 4, or 5
Ar is selected from the group consisting of phenyl, naphtalenyl and 1,4-biphenyl

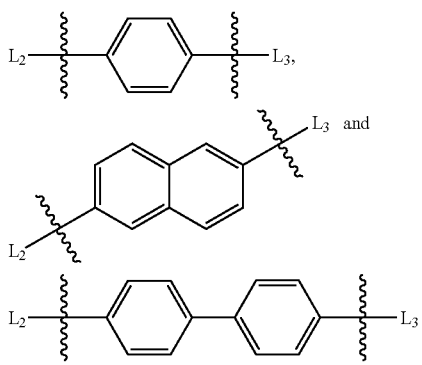

L3 is selected from the group consisting of O, S or —CH2
Gal is the radical β-D-galactopyranosyl:

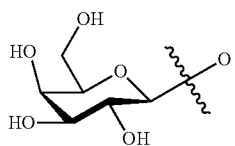

z is an integer selected from 1, 2 3, 4, 5, 6, 7, 8, 9 or 10.

2. The molecule according to claim 1, wherein K represents the mannose under the form D-mannopyranosyl.

3. The molecule according to claim 1, wherein L1 represents a group Pro (1,3-n-propyl), EG2M (diethylene glycol methylene), EG3M (triethylene glycol methylene), EG4M (tetraethylene glycol methylene).

4. The molecule according to claim 1, wherein Ar is a phenyl group.

5. The molecule according to claim 1, wherein z is 3 or 4.

6. The molecule according to claim 1, selected from the group consisting of:
Man(POProTzAcNPh-O-Gal)4
Gal(POProTzAcNPh-O-Gal)4
Glc(POProTzAcNPh-O-Gal)4
Man(POEG2MTzAcNPh-O-Gal)4
Man(POProTzAcNPh-O-Gal)8
Man[POTHME(MTzAcNPh-O-Gal)2]4
Man(PSEG2MTzAcNPh-CH2-O-Gal)4
Man(PSEG3MTzAcNPh-CH2-O-Gal)4
Man(POEG2MTzAcNPh-CH2-O-Gal)4
Man(POEG3MTzAcNPh-CH2-O-Gal)4
Man(POEG2MTzAcNPh-CH2-SGal)4
Man(POEG3MTzAcNPh-CH2-SGal)4
Man(PSEG3MTzAcNPh-O-Gal)4
Man(PSEG3MTzAcNPh-CH2-SGal)4
Man(PSEG2MTzAcNPh-CH2-SGal)4
Man(PSEG3MTzAcNPh-SGal)4
Man(PSEG2MTzAcNPh-O-Gal)4
Man(PSEG2MTzAcNPh-S-Gal)4
Man(POEG2MTzAcNPh-S-Gal)4
Man(POEG3MTzAcNPh-S-Gal)4
Man(POEG3MTzproNCONapht-O-Gal)4
Man(POEG3MTzproNCOBisph-O-Gal)4
Man(PSEG3MTzproNCOBisph-O-Gal)4
Man(PSEG2MTzproNCOBisph-O-Gal)4
Man(POEG2MTz AcNPh-O-Gal)4
Man(PSEG3MTzproNCONapht-O-Gal)4
Man(POEG3MTz AcNPh-O-Gal)4
Man(PSEG2MTzproNCONapht-O-Gal)4
Man(POEG2MTzproNCOBisphe-O-Gal)4
Man(POEG2MTzproNCONapht-O-Gal)4,
wherein Man represents mannose, Gal represents galactose, Glc represents glucose, Ph represents phenyl, Napht represents naphthyl, Bisph represents biphenyl, PO represents phosphodiester, and PS represents phosphorothioate.

7. A pharmaceutical composition comprising at least one compound according to claim 1 or a pharmaceutically acceptable salt thereof, and a pharmaceutically acceptable carrier and/or excipient.

8. The pharmaceutical composition according to claim 7 formulated to be inhaled or instilled in the respiratory tract.

9. The pharmaceutical composition according to claim 7, wherein the molecule of formula (II) comprises an antibacterial agent, and wherein the composition further comprises at least one or more other antibacterial agent(s) or one or more antiviral agent(s) or one or more drug(s) reinforcing the host innate immunity.

10. A method of treating a patient with an infection due to microbial pathogens comprising administering an effective amount of the pharmaceutical composition according to claim 7.

11. A method of treating a patient with an infection from *Pseudomonas aeruginosa* comprising administering an effective amount of the pharmaceutical composition according to claim 10.

12. A method of capturing *Pseudomonas aeruginosa* in a substance containing *Pseudomonas aeruginosa*, the method comprising adding to the substance an effective amount of a composition comprising at least one compound according to claim 1.

13. The molecule according to claim 2, wherein L1 represents a group Pro (1,3-n-propyl), EG2M (diethylene glycol methylene), EG3M (triethylene glycol methylene), EG4M (tetraethylene glycol methylene).

14. The molecule according to claim 2, wherein Ar is a phenyl group.

15. The molecule according to claim 2, wherein z is 3 or 4.

16. The molecule according to claim 2, selected from the group consisting of:
Man(POProTzAcNPh-O-Gal)$_4$
Gal(POProTzAcNPh-O-Gal)$_4$
Glc(POProTzAcNPh-O-Gal)$_4$
Man(POEG$_2$MTzAcNPh-O-Gal)$_4$
Man(POProTzAcNPh-O-Gal)$_8$
Man[POTHME(MTzAcNPh-O-Gal)$_2$]$_4$
Man(PSEG2MTzAcNPh-CH2-O-Gal)$_4$
Man(PSEG3MTzAcNPh-CH2-O-Gal)$_4$
Man(POEG2MTzAcNPh-CH2-O-Gal)$_4$
Man(POEG3MTzAcNPh-CH2-O-Gal)$_4$
Man(POEG2MTzAcNPh-CH2-S-Gal)$_4$
Man(POEG3MTzAcNPh-CH2-S-Gal)$_4$
Man(PSEG3MTzAcNPh-O-Gal)$_4$
Man(PSEG3MTzAcNPh-CH2-S-Gal)$_4$
Man(PSEG2MTzAcNPh-CH2-S-Gal)$_4$
Man(PSEG3MTzAcNPh-S-Gal)$_4$
Man(PSEG2MTzAcNPh-O-Gal)$_4$
Man(PSEG2MTzAcNPh-SGal)$_4$
Man(POG2MTzAcNPh-SGal)$_4$
Man(POEG3MTzAcNPh-SGal)$_4$
Man(POEG3MTzproNCONapht-OGal)$_4$
Man(POEG3MTzproNCOBisph-OGal)$_4$
Man(PSEG3MTzproNCOBisph-OGal)$_4$
Man(PSEG2MTzproNCOBisph-OGal)$_4$
Man(POEG2MTz AcNPh-O-Gal)$_4$
Man(PSEG3MTzproNCONapht-O-Gal)$_4$
Man(POEG3MTz AcNPh-O-Gal)$_4$
Man(PSEG2MTzproNCONapht-O-Gal)$_4$
Man(POEG2MTzproNCOBisph-O-Gal)$_4$
Man(POEG2MTzproNCONapht-O-Gal)$_4$
wherein Man represents mannose, Gal represents galactose, Glc represents glucose.

17. The molecule according to claim 3, wherein Ar is a phenyl group.

18. The molecule according to claim 3, wherein z is 3 or 4.

19. The molecule according to claim 4, wherein z is 3 or 4.

* * * * *